United States Patent
Koike et al.

(10) Patent No.: US 9,598,398 B2
(45) Date of Patent: Mar. 21, 2017

(54) HETEROCYCLIC COMPOUND

(71) Applicant: TAKEDA PHARMACEUTICAL COMPANY LIMITED, Osaka (JP)

(72) Inventors: Tatsuki Koike, Kanagawa (JP); Masato Yoshikawa, Kanagawa (JP); Haruhi Ando, Kanagawa (JP); William John Farnaby, Cambridge (GB); Shuhei Ikeda, Kanagawa (JP); Yuichi Kajita, Kanagawa (JP); Toshiya Nishi, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 14/781,963

(22) PCT Filed: Apr. 3, 2014

(86) PCT No.: PCT/JP2014/059892
§ 371 (c)(1),
(2) Date: Oct. 2, 2015

(87) PCT Pub. No.: WO2014/163161
PCT Pub. Date: Oct. 9, 2014

(65) Prior Publication Data
US 2016/0024049 A1      Jan. 28, 2016

(30) Foreign Application Priority Data

Apr. 4, 2013   (JP) ................. 2013-079023

(51) Int. Cl.
| | | |
|---|---|---|
| *C07D 401/14* | (2006.01) | |
| *C07D 403/14* | (2006.01) | |
| *A61K 31/497* | (2006.01) | |
| *A61K 31/4545* | (2006.01) | |
| *A61K 31/444* | (2006.01) | |
| *C07D 401/10* | (2006.01) | |
| *C07D 403/12* | (2006.01) | |
| *C07D 405/14* | (2006.01) | |
| *C07D 413/14* | (2006.01) | |
| *C07D 401/12* | (2006.01) | |
| *C07D 239/26* | (2006.01) | |
| *C07D 417/14* | (2006.01) | |
| *C07D 213/34* | (2006.01) | |
| *C07D 213/56* | (2006.01) | |
| *C07D 213/42* | (2006.01) | |

(52) U.S. Cl.
CPC ......... *C07D 401/10* (2013.01); *C07D 213/34* (2013.01); *C07D 213/42* (2013.01); *C07D 213/56* (2013.01); *C07D 239/26* (2013.01); *C07D 401/12* (2013.01); *C07D 401/14* (2013.01); *C07D 403/12* (2013.01); *C07D 403/14* (2013.01); *C07D 405/14* (2013.01); *C07D 413/14* (2013.01); *C07D 417/14* (2013.01)

(58) Field of Classification Search
None
See application file for complete search history.

(56) References Cited

U.S. PATENT DOCUMENTS

| | | |
|---|---|---|
| 2006/0183745 A1 | 8/2006 | Bo et al. |
| 2011/0306588 A1 | 12/2011 | Allen et al. |
| 2013/0090341 A1 | 4/2013 | Koike et al. |
| 2013/0253186 A1 | 9/2013 | Allen et al. |
| 2014/0088118 A1 | 3/2014 | Koike et al. |
| 2014/0088146 A1 | 3/2014 | Koike et al. |
| 2014/0228373 A1 | 8/2014 | Koike et al. |
| 2014/0323463 A1 | 10/2014 | Matsuya et al. |
| 2015/0315209 A1 | 11/2015 | Koike et al. |

FOREIGN PATENT DOCUMENTS

| | | |
|---|---|---|
| WO | 2006/089311 | 8/2006 |
| WO | 2010/110400 | 9/2010 |
| WO | 2011/143495 | 11/2011 |
| WO | 2013/054822 | 4/2013 |
| WO | 2013/108754 | 7/2013 |
| WO | 2014/092100 | 6/2014 |

OTHER PUBLICATIONS

Hörig et al., J. Translational Med. 2:44 (2004).*
International Search Report issued May 13, 2014 in International Application No. PCT/JP2014/059892.
STN Search Results for CAS Registry Nos. 1381392-24-0; 1359583-40-6; 1359583-35-9; 1358097-05-8; 1340977-50-5; 1340815-95-3; 1340804-53-6; 896060-69-8; 450389-18-1; and 450389-16-9.
Supplementary European Search Report issued Sep. 23, 2016 in European patent application No. 14 77 8814.

* cited by examiner

Primary Examiner — Michael Barker
(74) Attorney, Agent, or Firm — Wenderoth, Lind & Ponack, L.L.P.

(57) ABSTRACT

The present invention relates to a compound represented by the formula (I), which is useful as an agent for the prophylaxis or treatment of epilepsy, neurodegenerative disease and the like. In the formula (I), each symbol is as defined in the specification.

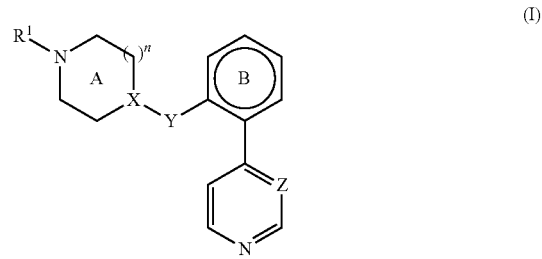

14 Claims, No Drawings

SEQUENCE LISTING

<160> NUMBER OF SEQ ID NOS: 2

<210> SEQ ID NO 1
<211> LENGTH: 26
<212> TYPE: DNA
<213> ORGANISM: Artificial
<220> FEATURE:
<223> OTHER INFORMATION: PCR primer

<400> SEQUENCE: 1
gccccggagc catgagcccc gggctg     26

<210> SEQ ID NO 2
<211> LENGTH: 26
<212> TYPE: DNA
<213> ORGANISM: Artificial
<220> FEATURE:
<223> OTHER INFORMATION: PCR primer

<400> SEQUENCE: 2
gtcctgcctg gaggcccct cagcag     26

HETEROCYCLIC COMPOUND

TECHNICAL FIELD

The present invention relates to a heterocyclic compound having a cholesterol 24-hydroxylase (in the present specification, sometimes to be abbreviated as "CH24H") inhibitory action, a pharmaceutical composition comprising same, and the like.

BACKGROUND OF THE INVENTION

Alzheimer's disease is a progressive neurodegenerative disease characterized by the deposition of amyloid β protein (Aβ), accumulation of phosphorylated tau in a nerve cell (neurofibrillary tangle), and nerve cell death. In recent years, the number of patients with Alzheimer's disease is increasing because of aging, but an effective treatment method has not been developed as yet. The therapeutic drugs for Alzheimer's disease which are currently used in the medical practice are mainly acetylcholinesterase (AchE) inhibitors. While AchE inhibitors is confirmed to provide a certain level of usefulness, since they are used with the aim of supplementing decreased acetylcholine, the treatment with AchE inhibitor is merely a symptomatic therapy. Thus, the prompt development of a basic remedy and prophylactic drug has been strongly desired.

It has been clarified that the presence of allele E4 of apolipoprotein E (ApoE) controlling the cholesterol metabolism is a strong risk factor of Alzheimer's disease [non-patent document 1: Science, vol. 261, 921-923, 1993]. After this finding, the correlation between plural gene polymorphisms playing a role in the expression of protein controlling the cholesterol metabolism and the onset frequency of Alzheimer's disease has been shown, suggesting the correlation between the cholesterol metabolism and Alzheimer's disease [non-patent document 2: Neurobiol. Aging, vol. 24, 421-426, 2003, non-patent document 3: Mol. Psychiatry, vol. 8, 635-638, 2003]. Moreover, it has been reported that Cyp46 (same as "cholesterol 24-hydroxylase (CH24H)"), which is cholesterol oxidase specifically expressed in the brain, is a risk factor of Alzheimer's disease [non-patent document 4: Neurosci. Lett., vol. 328, pages 9-12, 2002]. Furthermore, it has also been reported that Cyp46 (CH24H) is expressed in periphery of deposited amyloid in Alzheimer's disease patients [non-patent document 5: J. Biol. Chem., vol. 279, pages 34674-34681, 2004], 24S-hydroxycholesterol (24-HC), which is a metabolite thereof, increases in the brain spinal cord fluid (CSF) of Alzheimer's disease patients [non-patent document 6: Neurosci. Lett., vol. 324, pages 83-85, 2002, non-patent document 7: Neurosci. Lett., vol. 397, pages 83-87, 2006], 24-HC induces cell death of SH-SY5Y cell, which is a human neuroblast line [non-patent document 8: Brain Res., vol. 818, pages 171-175, 1999], and rats in which 24-HC was injected into the lateral cerebral ventricle showed impaired short-term memory, which is commonly observed in Alzheimer's disease, suggesting that hippocampal neurons were damaged by 24-HC [non-patent document 9: Neuroscience, vol. 164, pages 398-403, 2009]. These findings suggest that Cyp46 (CH24H) is deeply involved in the pathology of Alzheimer's disease. Therefore, a compound that inhibits the Cyp46 (CH24H) activity (i.e., Cyp46 (CH24H) inhibitor) suppresses neuronal cell death, increase in Aβ, intracerebral inflammation and the like observed in Alzheimer's disease, by decreasing intracerebral 24-HC, and is promising as a therapeutic or prophylactic drug showing not only an improvement of symptoms but also a suppression of progression. Moreover, it has been reported that an AchE inhibitor clinically used as a therapeutic drug for Alzheimer's disease shows an improvement effect on memory disorders induced by Aβ in mouse [non-patent document 10: British Journal of Pharmacology, vol. 149, pages 998-1012, 2006]. Thus, a Cyp46 (CH24H) inhibitor showing an improvement effect for memory disorders in Aβ overexpression animal model (APP transgenic mouse, APP/PS1 double transgenic mouse, etc.) is promising as a therapeutic drug for Alzheimer's disease.

As a concept of the preclinical stage of Alzheimer's disease, a mild cognitive impairment has been proposed, and about half of those having this disorder is said to progress into the Alzheimer's disease in the future. In recent years, it has been reported that 24-HC increases not only in patients with Alzheimer's disease but also in CSF of patients with mild cognitive impairment [non-patent document 7: Neurosci. Lett., vol. 397, pages 83-87, 2006]. This finding suggests that Cyp46 (CH24H) is involved in the pathology of mild cognitive impairment, and therefore, a Cyp46 (CH24H) inhibitor is promising as a new therapeutic drug for Alzheimer's disease or a prophylactic drug for the progression into the Alzheimer's disease.

In recent years, moreover, it has been reported that 24-HC in the blood increases before expression of the symptom in an autoimmune encephalomyelitis model, which is an animal model of multiple sclerosis which is one of the demyelination diseases in the central nervous system [non-patent document 11: J. Neurosci. Res., vol. 85, pages 1499-1505, 2007]. Multiple sclerosis is often developed in younger people of about 30 years old, and scarcely developed in the elderly of 60 years or older. It has also been reported that 24-HC in the blood increases in multiple sclerosis patients aged from 21 to 50 [non-patent document 12: Neurosci. Lett., vol. 331, pages 163-166, 2002]. These findings suggest that Cyp46 (CH24H) is involved in the pathology of multiple sclerosis, and therefore, a Cyp46 (CH24H) inhibitor is promising as a new therapeutic or prophylactic drug for multiple sclerosis.

Traumatic brain injury (also referred to as TBI in the present specification) is a condition having an extremely harmful influence on the personal health, for which no effective cure has been established. In the repair process following tissue damage by TBI, reconstruction of neuronal cell membrane and distribution of intracerebral cholesterol along with the growth of glial cell are suggested to be activated [non-patent document 13: Proc. Natl. Acad. Sci. USA, vol. 102, pages 8333-8338, 2005]. In a rat TBI model, an enhanced expression of Cyp46 (CH24H) after trauma has been reported [non-patent document 14: J. Neurotrauma, vol. 25, pages 1087-1098, 2008]. Moreover, it has also been reported that 24-HC is injurious to neuronal cells [non-patent document 8: Brain Res., vol. 818, pages 171-175, 1999]. Therefore, a Cyp46 (CH24H) inhibitor is promising as a new therapeutic or prophylactic drug for TBI.

As a pathological significance of 24-HC in neurodegenerative diseases, an inflammatory gene expression-enhancing action in neuronal cells has been reported [non-patent document 15: NeuroReport, vol. 16, pages 909-913, 2005]. In addition, it is suggested that an intracerebral inflammation reaction accompanied by activation of glial cell is a pathological change characteristic of neurodegenerative diseases [non-patent document 16: Glia, vol. 50, pages 427-434, 2005]. In recent years, an effectiveness of therapy by suppression of intracerebral inflammation has also been reported for neurodegenerative diseases such as Huntington's disease, Parkinson's disease and amyotrophic lateral sclerosis and the like [non-patent document 17: Mol. Neurodegeneration, vol. 4, pages 47-59, 2009]. Therefore, suppression of intracerebral inflammation via decreasing 24-HC by the inhibition of Cyp46 (CH24H) is promising as a new therapeutic or prophylactic drug for neurodegenerative diseases such as Huntington's disease, Parkinson's disease, cerebral infarction, glaucoma, amyotrophic lateral sclerosis and the like.

Glaucoma is the main cause of blindness, and is considered to be a serious social problem. However, there is no effective cure of a normal intraocular pressure type-visual field constriction, which is the major symptom of the disease. In recent years, it has been reported that gene polymorphisms of Cyp46 (CH24H) associated with high value of 24-HC in blood is related to the risk of the onset of glaucoma [non-patent document 18: Invest. Ophthalmol. Vis. Sci., vol. 50, pages 5712-5717, 2009]. Thus, a Cyp46 (CH24H) inhibitor is promising as a therapeutic or prophylactic drug for glaucoma.

Spasm is a disorder that convulsively occurs with abnormal electrical excitation of neuronal cell in the brain. Spasm is one of the characteristic clinical findings of Alzheimer's disease [Non-Patent Document 19: Epilepsia, vol. 47, pages 867-872, 2006], and the relationship between epilepsy and onset of Alzheimer's disease has been indicated [Non-Patent Document 20: Epilepsia, vol. 52, Supplement 1, pages 39-46, 2011]. It has been reported that spasm occurs with high frequency in APP/PS1 double transgenic mouse which is one of the Alzheimer's disease models due to Aβ overexpression [non-patent document 21: J. Neurosci., vol. 29, pages 3453-3462, 2012]. Furthermore, since hippocampus astrocytes induce the expression of Cyp46 (CH24H) in a kainic acid lesion rat model, which is one of the epilepsy models, the relationship between this enzyme and pathology of epilepsy has been indicated [Non-Patent Document 22: J. Neurol., vol. 65, pages 652-663, 2006]. It has been reported that a therapeutic drug for spasm, carbamazepine, shows an improving effect on short-term memory in Y-maze test in an epileptic spasm mouse model [Non-Patent Document 23: J. Neurol. Neurosurg. Psychiatry, vol. 48, pages 459-468, 1985]. Therefore, a CH24H inhibitor, which shows an improving effect on short-term memory in a model animal showing a spasm symptom, is promising as a novel therapeutic drug or prophylaxis drug for spasm, epilepsy, and the like.

Since schizophrenia shows a variety of psychological symptoms such as hallucination, delusion, excitation, manic-depressive state and the like, therapeutic drugs therefor have been developed with various approaches. In recent years, it has been pointed out that changes in the cholesterol metabolism are involved in the abnormality of neural activity seen in schizophrenia [non-patent document 24: J. Psychiatry Neurosci., vol. 36, pages 47-55, 2011]. Since cytotoxic factors such as oxidative stress also contribute to the pathology of schizophrenia, neuronal cell toxicity of 24-HC may aggravate the symptoms [non-patent document 25: Psychoneuroendocrinology, vol. 28, pages 83-96, 2003]. Therefore, a Cyp46 (CH24H) inhibitor that inhibits metabolizing cholesterol to 24-HC in the brain is promising as a therapeutic or prophylactic drug for schizophrenia.

Patent Document 1 discloses the compound represented by the following formula:

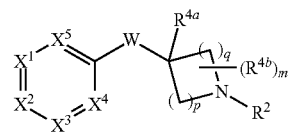

wherein $X^1$ is N or $CR^6$;
$X^2$ is N or $CR^6$;
$X^3$ is N or $CR^6$;
$X^4$ is N or $CR^6$;
$X^5$ is N or $CR^6$;
one or two of $X^1$, $X^2$, $X^3$, $X^4$ and $X^5$ is/are N;
W is —O—, —NH— or the like;
m is 0, 1, 2, 3 or 4;
p and q are each independently 0, 1, 2, 3, 4, 5 or 6, and $2 \leq p+q \leq 6$;
$R^1$ is halogen or the like;
$R^2$ is —C(=O)$R^5$ or -$L^2$;
$R^{4a}$ is H, $C_{1-4}$ alkyl or the like;
$R^{4b}$ are each independently F, Cl, Br, CN, OH or the like;
$R^5$ is H, $C_{1-8}$ alkyl or $C_{0-8}$ alkyl-$L^3$;
Each $R^6$ is independently $R^1$, H, halogen, CN, OH or the like; $L^2$ and $L^3$ are each independently a carbon-linked or nitrogen-linked saturated, partially-saturated or unsaturated 3, 4, 5, 6- or 7-membered monocycle optionally substituted by 0, 1, 2 or 3 of $R^7$, or the like; and
$R^7$ is independently F, Cl, Br, $C_{1-6}$ alkyl or the like, as a PDE10 inhibitor, which is an agent for the treatment of neurodegenerative disease such as Alzheimer's disease, schizophrenia and the like.

In addition, the following compounds are registered in Chemical Abstracts.

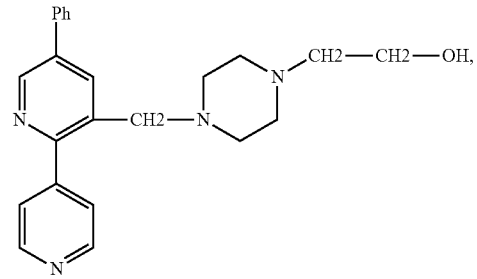

CAS registry number 1381392-24-0,

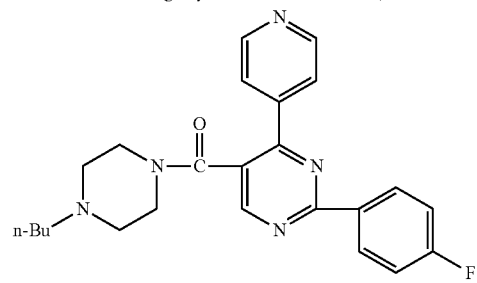

CAS registry number 1359583-40-6

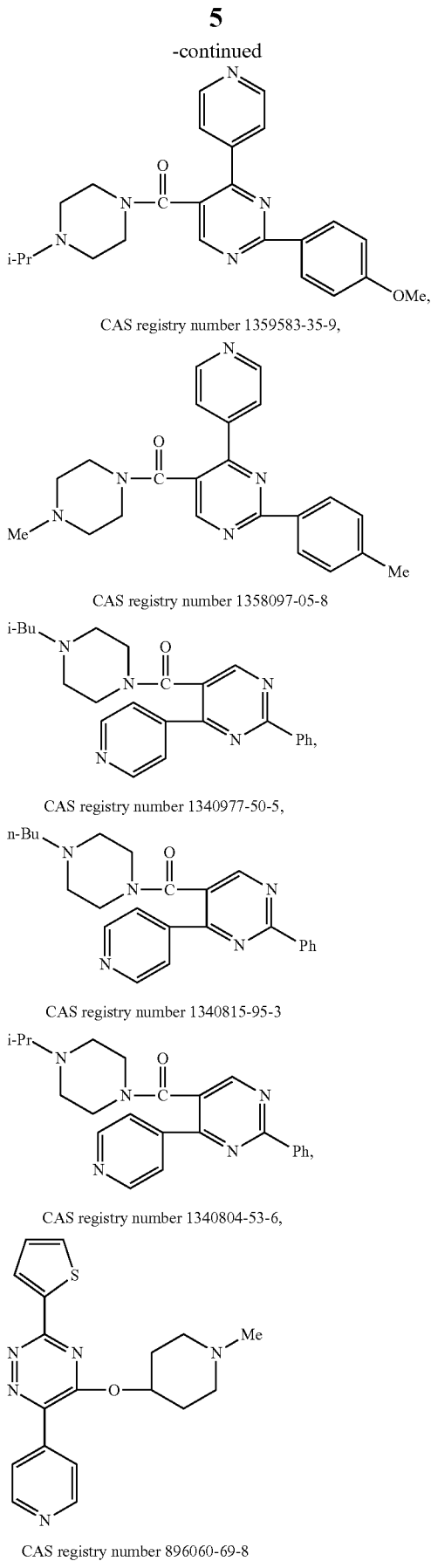

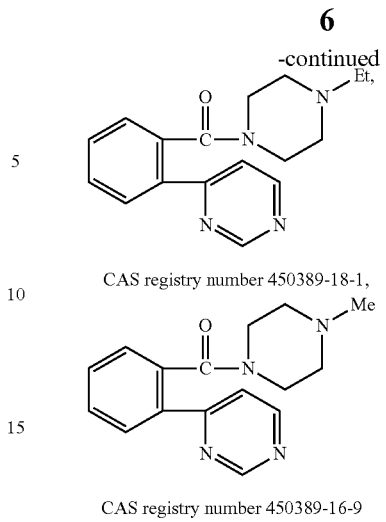

CAS registry number 450389-18-1,

CAS registry number 450389-16-9

DOCUMENT LIST

Patent Document

Patent Document 1: WO 2011/143495

Non-Patent Document

Non-Patent Document 1: Science, vol. 261, pages 921-923, 1993
Non-Patent Document 2: Neurobiology of Aging (Neurobiol. Aging), vol. 24, pages 421-426, 2003
Non-Patent Document 3: Molecular Psychiatry (Mol. Psychiatry), vol. 8, pages 635-638, 2003
Non-Patent Document 4: Neuroscience Letters (Neurosci. Lett.), vol. 328, pages 9-12, 2002
Non-Patent Document 5: Journal of the Biological Chemistry (J. Biol. Chem.), vol. 279, pages 34674-34681, 2004
Non-Patent Document 6: Neuroscience Letters (Neurosci. Lett.), vol. 324, pages 83-85, 2002
Non-Patent Document 7: Neuroscience Letters (Neurosci. Lett.), vol. 397, pages 83-87, 2006
Non-Patent Document 8: Brain Research (Brain Res.), vol. 818, pages 171-175, 1999
Non-Patent Document 9: Neuroscience, vol. 164, pages 398-403, 2009
Non-Patent Document 10: British Journal of Pharmacology, vol. 149, pages 998-1012, 2006
Non-Patent Document 11: Journal of Neuroscience Research (J. Neurosci, Res.), vol. 85, pages 1499-1505, 2007
Non-Patent Document 12: Neuroscience Letters (Neurosci. Lett.), vol. 331, pages 163-166, 2002
Non-Patent Document 13: Proceedings of the National Academy of Sciences USA (Proc. Natl. Acad. Sci. USA), vol. 102, pages 8333-8338, 2005
Non-Patent Document 14: Journal of Neurotrauma (J. Neurotrauma), vol. 25, pages 1087-1098, 2008
Non-Patent Document 15: NeuroReport, vol. 16, pages 909-913, 2005
Non-Patent Document 16: Glia, vol. 50, pages 427-434, 2005
Non-Patent Document 17: Molecular Neurodegeneration (Mol. Neurodegeneration), vol. 4, pages 47-59, 2009
Non-Patent Document 18: Investigative Ophthalmology & Visual Science (Invest. Opthalmol. Vis. Sci.), vol. 50, pages 5712-5717, 2009

Non-Patent Document 19: Epilepsia, vol. 47, pages 867-872, 2006

Non-Patent Document 20: Epilepsia, vol. 52, Supplement 1, pages 39-46, 2011

Non-Patent Document 21: Journal of Neuroscience (J. Neurosci.), vol. 29, pages 3453-3462, 2012

Non-Patent Document 22: Journal of Neurology (J. Neurol.), vol. 65, pages 652-663, 2006

Non-Patent Document 23: Journal of Neurology Neurosurgery Psychiatry (J. Neurol® Neurosurg. Psychiatry), vol. 48, pages 459-468, 1985

Non-Patent Document 24: Journal of Psychiatry Neuroscience (J. Psychiatry Neurosci.), vol. 36, pages 47-55, 2011

Non-Patent Document 25: Psychoneuroendocrinology, vol. 28, pages 83-96, 2003

SUMMARY OF THE INVENTION

Problems to be Solved by the Invention

An object of the present invention is to provide a compound having a superior CH24H inhibitory action, which is useful as an agent for the prophylaxis or treatment of epilepsy, neurodegenerative disease (e.g., Alzheimer's disease, mild cognitive disorder, Huntington's disease, Parkinson's disease, multiple sclerosis, amyotrophic lateral sclerosis, traumatic brain injury, cerebral infarction, glaucoma and the like), schizophrenia and the like.

Means of Solving the Problems

The present inventors have conducted intensive studies in an attempt to solve the above-mentioned problem and found that compound (I) represented by the following formula has a superior CH24H inhibitory action, which resulted in the completion of the present invention.

Accordingly, the present invention provides the following.

[1] A compound represented by the formula (I):

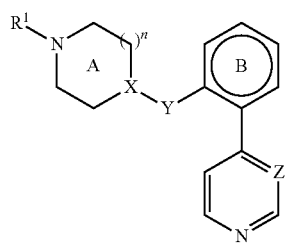

wherein
X is a carbon atom or a nitrogen atom;
Y is —O—, —S—, —NH—, —CH$_2$—, —CO—, —SO— or —SO$_2$—;
Z is CR$^4$ or N;
R$^1$ is an optionally substituted C$_{1-6}$ alkyl group, —CO—R$^2$, or —SO$_2$—R$^3$;
R$^2$ is an optionally substituted C$_{1-6}$ alkyl group, an optionally substituted C$_{1-6}$ alkoxy group, an optionally substituted C$_{6-14}$ aryl group, or an optionally substituted C$_{3-6}$ cycloalkyl group;
R$^3$ is a substituent;
R$^4$ is a hydrogen atom or a substituent;
n is 0 or 1;
Ring A is a 5- or 6-membered nitrogen-containing heterocycle optionally further substituted by 1 to 3 substituents selected from a halogen atom, an acyl group, an optionally substituted C$_{1-6}$ alkyl group, an optionally substituted hydroxy group, an optionally substituted sulfanyl group, an optionally substituted amino group and an oxo group; and
Ring B is a 6-membered aromatic ring optionally further substituted by 1 to 3 substituents selected from a halogen atom, a cyano group, an acyl group, an optionally substituted C$_{1-6}$ alkyl group, an optionally substituted hydroxy group, an optionally substituted sulfanyl group, and an optionally substituted amino group,
provided that (4-ethylpiperazin-1-yl)(2-(pyrimidin-4-yl)phenyl)methanone, and (4-methylpiperazin-1-yl)(2-(pyrimidin-4-yl)phenyl)methanone are excluded,
or a salt thereof (hereinafter to be referred to as compound (I).

[A] The compound or salt of the above-mentioned [1], wherein R$^1$ is a substituted C$_{1-2}$ alkyl group, an optionally substituted C$_{3-6}$ alkyl group, —CO—R$^2$, or —SO$_2$—R$^3$.

[B] The compound or salt of the above-mentioned [1], wherein
X is a carbon atom or a nitrogen atom;
Y is —O—, —CH$_2$—, —CO— or —SO$_2$—;
Z is CH or N;
R$^1$ is an optionally substituted C$_{1-6}$ alkyl group, —CO—R$^2$, or —SO$_2$—R$^3$;
R$^2$ is an optionally substituted C$_{1-6}$ alkyl group, an optionally substituted C$_{1-6}$ alkoxy group, an optionally substituted C$_{6-14}$ aryl group, or an optionally substituted C$_{3-8}$ cycloalkyl group;
R$^3$ is a substituent;
n is 0 or 1;
Ring A is a 5- or 6-membered nitrogen-containing heterocycle optionally further substituted by 1 to 3 substituents selected from a halogen atom and an oxo group; and
Ring B is a 6-membered aromatic ring optionally further substituted by 1 to 3 substituents selected from a halogen atom, a cyano group and an optionally substituted C$_{1-6}$ alkyl group,
provided that (4-ethylpiperazin-1-yl)(2-(pyrimidin-4-yl)phenyl)methanone, and (4-methylpiperazin-1-yl) (2-(pyrimidin-4-yl)phenyl)methanone are excluded.

[C] The compound or salt of the above-mentioned [1], wherein
X is a carbon atom or a nitrogen atom;
Y is —O—, —CH$_2$—, —CO— or —SO$_2$—;
Z is CH or N;
R$^1$ is a substituted C$_{1-2}$ alkyl group, an optionally substituted C$_{3-6}$ alkyl group, —CO—R$^2$, or —SO$_2$—R$^3$;
R$^2$ is an optionally substituted C$_{1-6}$ alkyl group, an optionally substituted C$_{1-6}$ alkoxy group, an optionally substituted C$_{6-14}$ aryl group, or an optionally substituted C$_{3-8}$ cycloalkyl group;
R$^3$ is a substituent;
n is 0 or 1;
Ring A is a 5- or 6-membered nitrogen-containing heterocycle optionally further substituted by 1 to 3 substituents selected from a halogen atom and an oxo group; and
Ring B is a 6-membered aromatic ring optionally further substituted by 1 to 3 substituents selected from a halogen atom, a cyano group and an optionally substituted C$_{1-6}$ alkyl group.

[D] The compound or salt of the above-mentioned [1], wherein
X is a carbon atom or a nitrogen atom;
Y is —O—, —CH$_2$—, —CO— or —SO$_2$—;
Z is CH or N;

$R^1$ is
(1) a $C_{1-6}$ alkyl group optionally substituted by 1 to 3 substituents selected from
  (i) a $C_{6-14}$ aryl group optionally substituted by 1 to 3 substituents selected from
    (a) a $C_{1-6}$ alkoxy group,
    (b) a cyano group, and
    (c) a halogen atom,
  (ii) a heterocyclic group optionally substituted by 1 to 3 $C_{1-6}$ alkyl groups,
  (iii) a $C_{3-8}$ cycloalkyl group,
  (iv) a mono- or di-$C_{1-6}$ alkyl-carbamoyl group, and
  (v) a heterocyclylcarbonyl group,
(2) —CO—$R^2$ wherein $R^2$ is
  (i) a $C_{1-6}$ alkyl group optionally substituted by 1 to 3 substituents selected from
    (a) a $C_{5-14}$ aryl group optionally substituted by 1 to 3 $C_{1-6}$ alkoxy groups, and
    (b) a $C_{3-8}$ cycloalkyl group,
  (ii) a $C_{1-6}$ alkoxy group,
  (iii) a $C_{6-14}$ aryl group, or
  (iv) a $C_{3-8}$ cycloalkyl group, or
(3) —$SO_2$—$R^3$ wherein $R^3$ is
  (i) a $C_{1-6}$ alkyl group optionally substituted by 1 to 3 halogen atoms,
  (ii) a $C_{3-8}$ cycloalkyl group,
  (iii) a $C_{6-14}$ aryl group optionally substituted by 1 to 3 substituents selected from
    (a) a $C_{1-6}$ alkoxy group, and
    (b) a halogen atom,
  (iv) a heterocyclic group optionally substituted by 1 to 3 $C_{1-6}$ alkyl groups, or
  (v) a mono- or di-$C_{1-6}$ alkyl-amino group;
n is 0 or 1;
Ring A is a 5- or 6-membered nitrogen-containing heterocycle optionally further substituted by 1 to 3 substituents selected from
  (1) a halogen atom, and
  (2) an oxo group; and
Ring B is a 6-membered aromatic ring optionally further substituted by 1 to 3 substituents selected from
  (1) a halogen atom,
  (2) a cyano group, and
  (3) a $C_{1-6}$ alkyl group optionally substituted by 1 to 3 halogen atoms,
provided that (4-ethylpiperazin-1-yl)(2-(pyrimidin-4-yl)phenyl)methanone, and (4-methylpiperazin-1-yl) (2-(pyrimidin-4-yl)phenyl)methanone are excluded.

[2] The compound or salt of the above-mentioned [1], wherein
X is a carbon atom or a nitrogen atom;
Y is —O—, —$CH_2$—, —CO— or —$SO_2$—;
Z is CH or N;
$R^1$ is
(1) a $C_{1-6}$ alkyl group optionally substituted by 1 to 3 substituents selected from
  (i) a $C_{6-14}$ aryl group optionally substituted by 1 to 3 substituents selected from
    (a) a $C_{1-6}$ alkoxy group,
    (b) a cyano group, and
    (c) a halogen atom,
  (ii) a pyridyl group, an imidazolyl group, an oxazolyl group, a pyrazolyl group, a tetrahydrofuryl group, an isoxazolyl group, a pyrimidinyl group, a pyrazinyl group and a thiazolyl group, each optionally substituted by 1 to 3 $C_{1-6}$ alkyl groups,
  (iii) a $C_{3-8}$ cycloalkyl group,
  (iv) a mono- or di-$C_{1-6}$ alkyl-carbamoyl group, and
  (v) a pyrrolidinylcarbonyl group, a morpholinylcarbonyl group and an azetidinylcarbonyl group,
(2) —CO—$R^2$ wherein $R^2$ is
  (i) a $C_{1-6}$ alkyl group optionally substituted by 1 to 3 substituents selected from
    (a) a $C_{6-14}$ aryl group optionally substituted by 1 to 3 $C_{1-6}$ alkoxy groups, and
    (b) a $C_{3-8}$ cycloalkyl group,
  (ii) a $C_{1-6}$ alkoxy group,
  (iii) a $C_{6-14}$ aryl group, or
  (iv) a $C_{3-8}$ cycloalkyl group, or
(3) —$SO_2$—$R^3$ wherein $R^3$ is
  (i) a $C_{1-6}$ alkyl group optionally substituted by 1 to 3 halogen atoms,
  (ii) a $C_{3-8}$ cycloalkyl group,
  (iii) a $C_{6-14}$ aryl group optionally substituted by 1 to 3 substituents selected from
    (a) a $C_{1-6}$ alkoxy group, and
    (b) a halogen atom,
  (iv) a pyrazolyl group, a morpholinyl group or a pyridyl group, each optionally substituted by 1 to 3 $C_{1-6}$ alkyl groups, or
  (v) a mono- or di-$C_{1-6}$ alkyl-amino group;
n is 0 or 1;
Ring A is a pyrrolidine ring, a piperidine ring or a piperazine ring, each optionally further substituted by 1 to 3 substituents selected from
  (1) a halogen atom, and
  (2) an oxo group; and
Ring B is a benzene ring, a pyridine ring, a pyrimidine ring or a pyrazine ring, each optionally further substituted by 1 to 3 substituents selected from
  (1) a halogen atom,
  (2) a cyano group, and
  (3) a $C_{1-6}$ alkyl group optionally substituted by 1 to 3 halogen atoms,
provided that (4-ethylpiperazin-1-yl)(2-(pyrimidin-4-yl)phenyl)methanone, and (4-methylpiperazin-1-yl) (2-(pyrimidin-4-yl)phenyl)methanone are excluded.

[E] The compound or salt of the above-mentioned [1], wherein
X is a carbon atom or a nitrogen atom;
Y is —O—, —$CH_2$—, —CO— or —$SO_2$—;
Z is CH or N;
$R^1$ is
(1) a $C_{1-6}$ alkyl group optionally substituted by 1 to 3 substituents selected from
  (i) a phenyl group optionally substituted by 1 to 3 substituents selected from
    (a) a $C_{1-5}$ alkoxy group,
    (b) a cyano group, and
    (c) a halogen atom,
  (ii) a pyridyl group, an imidazolyl group, an oxazolyl group, a pyrazolyl group, a tetrahydrofuryl group, an isoxazolyl group, a pyrimidinyl group, a pyrazinyl group and a thiazolyl group, each optionally substituted by 1 to 3 $C_{1-6}$ alkyl groups,
  (iii) a cyclopropyl group,
  (iv) a mono- or di-$C_{1-6}$ alkyl-carbamoyl group, and
  (v) a pyrrolidinylcarbonyl group, a morpholinylcarbonyl group and an azetidinylcarbonyl group,
(2) —CO—$R^2$ wherein $R^2$ is
  (i) a $C_{1-6}$ alkyl group optionally substituted by 1 to 3 substituents selected from (a) a phenyl group optionally substituted by 1 to 3 $C_{1-6}$ alkoxy groups, and
(b) a cyclopropyl group,
(ii) a $C_{1-6}$ alkoxy group,
(iii) a phenyl group, or
(iv) a cyclopropyl group, or
(3) —$SO_2$—$R^3$ wherein $R^3$ is
(i) a $C_{1-6}$ alkyl group optionally substituted by 1 to 3 halogen atoms,
(ii) a cyclopropyl group,
(iii) a phenyl group optionally substituted by 1 to 3 substituents selected from
(a) a $C_{1-6}$ alkoxy group, and
(b) a halogen atom,
(iv) a pyrazolyl group, a morpholinyl group or a pyridyl group, each optionally substituted by 1 to 3 $C_{1-6}$ alkyl groups, or
(v) a mono- or di-$C_{1-6}$ alkyl-amino group;
n is 0 or 1;
Ring A is a pyrrolidine ring, a piperidine ring or a piperazine ring, each optionally further substituted by 1 to 3 substituents selected from
(1) a halogen atom, and
(2) an oxo group; and
Ring B is a benzene ring, a pyridine ring, a pyrimidine ring or a pyrazine ring, each optionally further substituted by 1 to 3 substituents selected from
(1) a halogen atom,
(2) a cyano group, and
(3) a $C_{1-6}$ alkyl group optionally substituted by 1 to 3 halogen atoms,
provided that (4-ethylpiperazin-1-yl)(2-(pyrimidin-4-yl)phenyl)methanone, and (4-methylpiperazin-1-yl)(2-(pyrimidin-4-yl)phenyl)methanone are excluded.

[3] The compound or salt of the above-mentioned [1], wherein
X is a carbon atom or a nitrogen atom;
Y is —O—, —$CH_2$—, —CO— or —$SO_2$—;
Z is CH or N;
$R^1$ is
(1) a $C_{1-6}$ alkyl group substituted by 1 to 3 substituents selected from
(i) a phenyl group optionally substituted by 1 to 3 substituents selected from
(a) a $C_{1-6}$ alkoxy group,
(b) a cyano group, and
(c) a halogen atom,
(ii) a pyridyl group, an imidazolyl group, an oxazolyl group, a pyrazolyl group, a tetrahydrofuryl group, an isoxazolyl group, a pyrimidinyl group, a pyrazinyl group and a thiazolyl group, each optionally substituted by 1 to 3 $C_{1-6}$ alkyl groups,
(iii) a cyclopropyl group,
(iv) a mono- or di-$C_{1-6}$ alkyl-carbamoyl group, and
(v) a pyrrolidinylcarbonyl group, a morpholinylcarbonyl group and an azetidinylcarbonyl group,
(2) —CO—$R^2$ wherein $R^2$ is
(i) a $C_{1-6}$ alkyl group optionally substituted by 1 to 3 substituents selected from
(a) a phenyl group optionally substituted by 1 to 3 $C_{1-6}$ alkoxy groups, and
(b) a cyclopropyl group,
(ii) a $C_{1-6}$ alkoxy group,
(iii) a phenyl group, or
(iv) a cyclopropyl group, or
(3) —$SO_2$—$R^3$ wherein $R^3$ is
(i) a $C_{1-6}$ alkyl group optionally substituted by 1 to 3 halogen atoms,
(ii) a cyclopropyl group,
(iii) a phenyl group optionally substituted by 1 to 3 substituents selected from
(a) a $C_{1-6}$ alkoxy group, and
(b) a halogen atom,
(iv) a pyrazolyl group, a morpholinyl group or a pyridyl group, each optionally substituted by 1 to 3 $C_{1-6}$ alkyl groups, or
(v) a mono- or di-$C_{1-6}$ alkyl-amino group;
n is 0 or 1;
Ring A is a pyrrolidine ring, a piperidine ring or a piperazine ring, each optionally further substituted by 1 to 3 substituents selected from
(1) a halogen atom, and
(2) an oxo group; and
Ring B is a benzene ring, a pyridine ring, a pyrimidine ring or a pyrazine ring, each optionally further substituted by 1 to 3 substituents selected from
(1) a halogen atom,
(2) a cyano group, and
(3) a $C_{1-6}$ alkyl group optionally substituted by 1 to 3 halogen atoms.

[F] The compound or salt of the above-mentioned [1], wherein
X is a carbon atom;
Y is —O—;
Z is CH;
$R^1$ is
(1) a $C_{1-6}$ alkyl group optionally substituted by 1 to 3 substituents selected from
(i) a phenyl group,
(ii) a pyrazolyl group and a thiazolyl group, each optionally substituted by 1 to 3 $C_{1-6}$ alkyl groups, and
(iii) a mono- or di-$C_{1-6}$ alkyl-carbamoyl group, or
(2) —$SO_2$—$R^3$ wherein $R^3$ is a phenyl group optionally substituted by 1 to 3 $C_{1-6}$ alkoxy groups;
n is 0 or 1;
Ring A is a pyrrolidine ring or a piperidine ring, each optionally further substituted by 1 to 3 halogen atoms; and
Ring B is a benzene ring, a pyridine ring or a pyrazine ring.

[4] The compound or salt of the above-mentioned [1], wherein
X is a carbon atom;
Y is —O—;
Z is CH;
$R^1$ is
(1) a $C_{1-6}$ alkyl group optionally substituted by 1 to 3 substituents selected from
(i) a pyrazolyl group and a thiazolyl group, each optionally substituted by 1 to 3 $C_{1-5}$ alkyl groups, and
(ii) a mono- or di-$C_{1-6}$ alkyl-carbamoyl group, or
(2) —$SO_2$—$R^3$ wherein $R^3$ is a phenyl group optionally substituted by 1 to 3 $C_{1-6}$ alkoxy groups;
n is 0 or 1;
Ring A is a pyrrolidine ring or a piperidine ring, each optionally further substituted by 1 to 3 halogen atoms; and
Ring B is a pyridine ring or a pyrazine ring.

[G] 3-((1-((1-methyl-1H-pyrazol-4-yl)methyl)piperidin-4-yl)oxy)-2,4'-bipyridine or a salt thereof, 2-(3,3-difluoro-4-((3-(pyridin-4-yl)pyrazin-2-yl)oxy)piperidin-1-yl)-N,N-dimethylacetamide or a salt thereof, or 3-((1-((4-methoxyphenyl)sulfonyl)pyrrolidin-3-yl)oxy)-2,4'-bipyridine or a salt thereof.

[5] 3-((1-((1-Methyl-1H-pyrazol-4-yl)methyl)piperidin-4-yl)oxy)-2,4'-bipyridine or a salt thereof.

[6] 2-(3,3-Difluoro-4-((3-(pyridin-4-yl)pyrazin-2-yl)oxy)piperidin-1-yl)-N,N-dimethylacetamide or a salt thereof.

[7] 3-((1-((4-Methoxyphenyl)sulfonyl)pyrrolidin-3-yl)oxy)-2,4'-bipyridine or a salt thereof.

[8] A medicament comprising the compound or salt of any of the above-mentioned [1] to [7] and [A] to [G].

[9] The medicament of the above-mentioned [8], which is a cholesterol 24 hydroxylase inhibitor.

[10] The medicament of the above-mentioned [8], which is an agent for the prophylaxis or treatment of epilepsy or neurodegenerative disease.

[11] The medicament of the above-mentioned [10], wherein the neurodegenerative disease is Alzheimer's disease, mild cognitive disorder, Huntington's disease, Parkinson's disease or multiple sclerosis.

[12] The compound or salt of any of the above-mentioned [1] to [7] and [A] to [G] for use in the prophylaxis or treatment of epilepsy or neurodegenerative disease.

[13] The compound or salt of the above-mentioned [12], wherein the neurodegenerative disease is Alzheimer's disease, mild cognitive disorder, Huntington's disease, Parkinson's disease or multiple sclerosis.

[14] A method of inhibiting cholesterol 24-hydroxylase in a mammal, which comprises administering an effective amount of the compound or salt of any of the above-mentioned [1] to [7] and [A] to [G] to the mammal.

[15] A method for the prophylaxis or treatment of epilepsy or neurodegenerative disease in a mammal, which comprises administering an effective amount of the compound or salt of any of the above-mentioned [1] to [7] and [A] to [G] to the mammal.

[16] The method of the above-mentioned [15], wherein the neurodegenerative disease is Alzheimer's disease, mild cognitive disorder, Huntington's disease, Parkinson's disease or multiple sclerosis.

[17] Use of the compound or salt of any of the above-mentioned [1] to [7] and [A] to [G] for the production of an agent for the prophylaxis or treatment of epilepsy or neurodegenerative disease.

[18] The use of the above-mentioned [17], wherein the neurodegenerative disease is Alzheimer's disease, mild cognitive disorder, Huntington's disease, Parkinson's disease or multiple sclerosis.

Effect of the Invention

Compound (I) has a superior CH24H inhibitory action, which is useful as an agent for the prophylaxis or treatment of epilepsy, neurodegenerative disease (e.g., Alzheimer's disease, mild cognitive disorder, Huntington's disease, Parkinson's disease, multiple sclerosis, amyotrophic lateral sclerosis, traumatic brain injury, cerebral infarction, glaucoma and the like), schizophrenia and the like.

DETAILED DESCRIPTION OF THE INVENTION

In the present specification, the "halogen atom" means a fluorine atom, a chlorine atom, a bromine atom or an iodine atom.

In the present specification, the "$C_{1-6}$ alkyl (group)" means, for example, methyl, ethyl, propyl, isopropyl, butyl, isobutyl, sec-butyl, tert-butyl, pentyl, isopentyl, neo-pentyl, 1-ethylpropyl, hexyl, isohexyl, 1,1-dimethylbutyl, 2,2-dimethylbutyl, 3,3-dimethylbutyl, 2-ethylbutyl or the like.

In the present specification, the "$C_{1-5}$ alkyl (group)" means, for example, methyl, ethyl, propyl, isopropyl, butyl, isobutyl, sec-butyl, tert-butyl, pentyl, isopentyl, neo-pentyl, 1-ethylpropyl or the like.

In the present specification, the "$C_{1-2}$ alkyl (group)" means, for example, methyl or ethyl.

In the present specification, the "$C_{3-6}$ alkyl (group)" means, for example, propyl, isopropyl, butyl, isobutyl, sec-butyl, tert-butyl, pentyl, isopentyl, neo-pentyl, 1-ethylpropyl, hexyl, isohexyl, 1,1-dimethylbutyl, 2,2-dimethylbutyl, 3,3-dimethylbutyl, 2-ethylbutyl or the like.

In the present specification, the "$C_{2-6}$ alkenyl (group)" means, for example, vinyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl or the like.

In the present specification, the "$C_{2-6}$ alkynyl (group)" means, for example, ethynyl, 1-propynyl, 2-propynyl, 1-butynyl, 2-butynyl, 3-butynyl, 1-pentynyl, 2-pentynyl, 3-pentynyl, 4-pentynyl, 1,1-dimethylprop-2-yn-1-yl, 1-hexynyl, 2-hexynyl, 3-hexynyl, 4-hexynyl, 5-hexynyl or the like.

In the present specification, the "$C_{1-6}$ alkoxy (group)" means, for example, methoxy, ethoxy, propoxy, isopropoxy, butoxy, isobutoxy, sec-butoxy, tert-butoxy, pentyloxy, isopentyloxy, hexyloxy or the like.

In the present specification, the "$C_{2-6}$ alkenyloxy (group)" means, for example, vinyloxy, 1-propenyloxy, 2-propenyloxy, 2-methyl-1-propenyloxy, 1-butenyloxy, 2-butenyloxy, 3-butenyloxy, 3-methyl-2-butenyloxy, 1-pentenyloxy, 2-pentenyloxy, 3-pentenyloxy, 4-pentenyloxy, 4-methyl-3-pentenyloxy, 1-hexenyloxy, 3-hexenyloxy, 5-hexenyloxy or the like.

In the present specification, the "$C_{2-6}$ alkynyloxy (group)" means, for example, ethynyloxy, 1-propynyloxy, 2-propynyloxy, 1-butynyloxy, 2-butynyloxy, 3-butynyloxy, 1-pentynyloxy, 2-pentynyloxy, 3-pentynyloxy, 4-pentynyloxy, dimethylprop-2-yn-1-yloxy, 1-hexynyloxy, 2-hexynyloxy, 3-hexynyloxy, 4-hexynyloxy, 5-hexynyloxy or the like.

In the present specification, the "$C_{1-6}$ alkylenedioxy (group)" means, for example, methylenedioxy, ethylenedioxy or the like.

In the present specification, the "$C_{1-6}$ alkoxy-carbonyl (group)" means, for example, methoxycarbonyl, ethoxycarbonyl, propoxycarbonyl, isopropoxycarbonyl, butoxycarbonyl, isobutoxycarbonyl, tert-butoxycarbonyl or the like.

In the present specification, the "$C_{1-6}$ alkyl-carbonyl (group)" means, for example, acetyl, propanoyl, butanoyl, 2-methylpropanoyl or the like.

In the present specification, the "mono-$C_{1-6}$ alkylamino (group)" means, for example, methylamino, ethylamino, propylamino, isopropylamino, butylamino, isobutylamino, tert-butylamino or the like.

In the present specification, the "di-$C_{1-6}$ alkylamino (group)" means, for example, dimethylamino, diethylamino, dipropylamino, diisopropylamino, dibutylamino, diisobutylamino, ditert-butylamino or the like.

In the present specification, the "$C_{3-8}$ cycloalkyl (group)" means, for example, cyclopropyl, cyclobutyl, cyclopentyl, cyclohexyl, cycloheptyl, cyclooctyl or the like.

In the present specification, the "$C_{3-6}$ cycloalkyl (group)" means, for example, cyclopropyl, cyclobutyl, cyclopentyl, cyclohexyl or the like.

In the present specification, the "$C_{3-8}$ cycloalkyloxy (group)" means, for example, cyclopropyloxy, cyclobutyloxy, cyclopentyloxy, cyclohexyloxy, cycloheptyloxy, cyclooctyloxy or the like.

In the present specification, the "$C_{3-6}$ cycloalkyloxy (group)" means, for example, cyclopropyloxy, cyclobutyloxy, cyclopentyloxy, cyclohexyloxy or the like.

In the present specification, the "$C_{3-8}$ cycloalkenyl (group)" means, for example, cyclopropenyl (e.g., 2-cyclopropen-1-yl), cyclobutenyl (e.g., 2-cyclobuten-1-yl), cyclopentenyl (e.g., 2-cyclopenten-1-yl, 3-cyclopenten-1-yl), cyclohexenyl (e.g., 2-cyclohexen-1-yl, 3-cyclohexen-1-yl), cycloheptenyl (e.g., 1-cyclopenten-1-yl, 2-cyclohepten-1-yl, 2-cyclohepten-1-yl), cyclooctenyl (e.g., 1-cyclohepten-1-yl, 2-cyclohepten-1-yl, 3-cyclohepten-1-yl) or the like.

In the present specification, the "$C_{3-8}$ cycloalkenyloxy (group)" means, for example, cyclopropenyloxy (e.g., 2-cyclopropen-1-yloxy), cyclobutenyloxy (e.g., 2-cyclobuten-1-yloxy), cyclopentenyloxy (e.g., 2-cyclopenten-1-yloxy, 3-cyclopenten-1-yloxy), cyclohexenyloxy (e.g., 2-cyclohexen-1-yloxy, 3-cyclohexen-1-yloxy) or the like.

In the present specification, the "$C_{4-5}$ cycloalkadienyl group" means, for example, 1,3-cyclobutadien-1-yl, 1,3-cyclopentadien-1-yl, 1,4-cyclopentadien-1-yl, 2,4-cyclopentadien-1-yl, 1,3-cyclohexadien-1-yl, 1,4-cyclohexadien-1-yl, 1,5-cyclohexadien-1-yl, 2,4-cyclohexadien-1-yl, 2,5-cyclohexadien-1-yl or the like.

In the present specification, the "$C_{6-14}$ aryloxy (group)" means, for example, phenoxy, 1-naphthyloxy, 2-naphthyloxy or the like.

In the present specification, the "$C_{7-14}$ aralkyloxy (group)" means, for example, benzyloxy, phenethyloxy or the like.

Each symbol of the formula (I) is explained below.

In the formula (I), X is a carbon atom or a nitrogen atom. X is preferably a carbon atom.

In the formula (I), Y is —O—, —S—, —NH—, —CH$_2$—, —CO—, —SO— or —SO$_2$—.

Y is preferably —O—, —CH$_2$—, —CO— or —SO$_2$—, more preferably —O—.

In the formula (I), Z is CR$^4$ or N.

In the formula (I), R$^4$ is a hydrogen atom or a substituent.

Examples of the "substituent" represented by R$^4$ include an "optionally substituted hydrocarbon group", an "optionally substituted heterocyclic group", an "optionally substituted hydroxy group", an "optionally substituted amino group", an "optionally substituted sulfanyl group", an "acyl group", a "halogen atom", a "cyano group", a "nitro group" and the like.

Examples of the "hydrocarbon group" of the "optionally substituted hydrocarbon group" include a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{4-10}$ cycloalkadienyl group, a $C_{6-14}$ aryl group, a $C_{7-14}$ aralkyl group, a $C_{8-13}$ arylalkenyl group and the like.

Examples of the $C_{1-10}$ alkyl group include methyl, ethyl, propyl, isopropyl, butyl, isobutyl, sec-butyl, tert-butyl, pentyl, isopentyl, neo-pentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like. Among them, a $C_{1-6}$ alkyl group is preferable.

Examples of the $C_{2-10}$ alkenyl group include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like. Among them, a $C_{2-6}$ alkenyl group is preferable.

Examples of the $C_{2-10}$ alkynyl group include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like. Among them, a $C_{2-6}$ alkynyl group is preferable.

Examples of the $C_{3-10}$ cycloalkyl group include cyclopropyl, cyclobutyl, cyclopentyl, cyclohexyl, cycloheptyl, cyclooctyl and the like. Among them, a $C_{3-6}$ cycloalkyl group is preferable.

Examples of the $C_{3-10}$ cycloalkenyl group include 2-cyclopenten-1-yl, 3-cyclopenten-1-yl, 2-cyclohexen-1-yl, 3-cyclohexen-1-yl and the like. Among them, a $C_{3-6}$ cycloalkenyl group is preferable.

Examples of the $C_{4-10}$ cycloalkadienyl group include 2,4-cyclopentadien-1-yl, 2,4-cyclohexadien-1-yl, 2,5-cyclohexadien-1-yl and the like. Among them, $C_{4-6}$ cycloalkadienyl group is preferable.

The above-mentioned $C_{3-10}$ cycloalkyl group, $C_{3-10}$ cycloalkenyl group and $C_{4-10}$ cycloalkadienyl group are each optionally fused with a benzene ring to form a fused ring group, and examples of the fused ring group include indanyl, dihydronaphthyl, tetrahydronaphthyl, fluorenyl and the like.

The above-mentioned $C_{3-10}$ cycloalkyl group, $C_{3-10}$ cycloalkenyl group and $C_{4-10}$ cycloalkadienyl group may be a $C_{7-10}$ bridged hydrocarbon group. Examples of the $C_{7-10}$ bridged hydrocarbon group include bicyclo[2.2.1]heptyl (norbornyl), bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like.

The above-mentioned $C_{3-10}$ cycloalkyl group, $C_{3-10}$ cycloalkenyl group and $C_{4-10}$ cycloalkadienyl group each optionally form a spiro ring group with a $C_{3-10}$ cycloalkane, a $C_{3-10}$ cycloalkene or a $C_{4-10}$ cycloalkadiene. Examples of the $C_{3-10}$ cycloalkane, $C_{3-10}$ cycloalkene and $C_{4-10}$ cycloalkadiene include rings corresponding to the above-mentioned $C_{3-10}$ cycloalkyl group, $C_{3-10}$ cycloalkenyl group and $C_{4-10}$ cycloalkadienyl group. Examples of the Spiro ring group include spiro[4.5]decan-8-yl and the like.

Examples of the $C_{6-14}$ aryl group include phenyl, naphthyl, anthryl, phenanthryl, acenaphthylenyl, biphenylyl and the like. Among them, a $C_{6-12}$ aryl group is preferable.

Examples of the $C_{7-14}$ aralkyl group include benzyl, phenethyl, naphthyl methyl, biphenylylmethyl and the like.

Examples of the $C_{8-13}$ arylalkenyl group include styryl and the like.

The $C_{1-10}$ alkyl group, $C_{2-10}$ alkenyl group and $C_{2-10}$ alkynyl group, which are exemplified as the above-mentioned "hydrocarbon group", optionally have 1 to 7 (preferably 1 to 3) substituents at substitutable position(s).

Examples of the substituent include substituents selected from the following Substituent Group A. When the number of the substituents is plural, the respective substituents may be the same or different.

Substituent Group A:

(1) a halogen atom;

(2) a cyano group;

(3) a nitro group;

(4) a hydroxy group;

(5) a $C_{3-8}$ cycloalkyl group optionally substituted by 1 to 3 substituents selected from
  (a) a halogen atom,
  (b) a cyano group,
  (c) a $C_{1-6}$ alkyl group optionally substituted by 1 to 3 halogen atoms, and
  (d) a $C_{1-6}$ alkoxy group optionally substituted by 1 to 3 halogen atoms;

(6) a $C_{6-14}$ aryl group optionally substituted by 1 to 3 substituents selected from (a) a halogen atom,
(b) a cyano group,
(c) a $C_{1-6}$ alkyl group optionally substituted by 1 to 3 halogen atoms, and
(d) a $C_{1-5}$ alkoxy group optionally substituted by 1 to 3 halogen atoms;
(7) a $C_{1-6}$ alkoxy group optionally substituted by 1 to 3 substituents selected from
(a) a halogen atom,
(b) a cyano group,
(c) a $C_{3-8}$ cycloalkyl group optionally having 1 to 3 halogen atoms,
(d) a $C_{3-8}$ cycloalkenyl group optionally having 1 to 3 halogen atoms,
(e) a $C_{6-14}$ aryl group optionally having 1 to 3 halogen atoms, and
(f) a 5- or 6-membered monocyclic aromatic heterocyclic group;
(8) a $C_{2-5}$ alkenyloxy group (e.g., vinyloxy, propenyloxy, butenyloxy, pentenyloxy, hexenyloxy) optionally having 1 to 3 halogen atoms;
(9) a $C_{3-5}$ alkynyloxy group (e.g., ethynyloxy, propynyloxy, butynyloxy, pentynyloxy, hexynyloxy) optionally having 1 to 3 halogen atoms;
(10) a $C_{3-8}$ cycloalkyloxy group (e.g., cyclopropyloxy, cyclobutyloxy, cyclopentyloxy, cyclohexyloxy) optionally having 1 to 3 halogen atoms;
(11) a $C_{3-8}$ cycloalkenyloxy group (e.g., cyclopropenyloxy, cyclobutenyloxy, cyclopentenyloxy, cyclohexenyloxy) optionally having 1 to 3 halogen atoms;
(12) a $C_{6-14}$ aryloxy group optionally having 1 to 3 halogen atoms;
(13) a $C_{7-14}$ aralkyloxy group optionally having 1 to 3 halogen atoms;
(14) a carbamoyl group optionally mono- or di-substituted by substituent(s) selected from
(a) a $C_{1-6}$ alkyl group,
(b) a $C_{3-6}$ cycloalkyl group,
(c) a $C_{6-14}$ aryl group,
(d) a $C_{1-6}$ alkoxy group,
(e) a 5- or 6-membered monocyclic aromatic heterocyclic group,
(f) an 8- to 12-membered fused aromatic heterocyclic group,
(g) a 3- to 8-membered monocyclic non-aromatic heterocyclic group, and
(h) an 8- to 12-membered fused non-aromatic heterocyclic group;
(15) a sulfamoyl group optionally mono- or di-substituted by substituent(s) selected from
(a) a $C_{1-6}$ alkyl group,
(b) a $C_{3-6}$ cycloalkyl group,
(c) a $C_{6-14}$ aryl group,
(d) a $C_{1-6}$ alkoxy group,
(e) a 5- or 6-membered monocyclic aromatic heterocyclic group,
(f) an 8- to 12-membered fused aromatic heterocyclic group,
(g) a 3- to 8-membered monocyclic non-aromatic heterocyclic group, and
(h) an 8- to 12-membered fused non-aromatic heterocyclic group;
(16) a formyl group;
(17) a $C_{1-6}$ alkyl-carbonyl group;
(18) a $C_{2-6}$ alkenyl-carbonyl group (e.g., acryloyl, butenoyl, pentenoyl, hexenoyl, heptenoyl);
(19) a $C_{2-6}$ alkynyl-carbonyl group (e.g., propioloyl, propynylcarbonyl, butynylcarbonyl, pentynylcarbonyl, hexynylcarbonyl);
(20) a $C_{3-8}$ cycloalkyl-carbonyl group (e.g., cyclopropylcarbonyl, cyclobutylcarbonyl, cyclopentylcarbonyl, cyclohexylcarbonyl);
(21) a $C_{3-8}$ cycloalkenyl-carbonyl group (e.g., cyclopropenylcarbonyl, cyclobutenylcarbonyl, cyclopentenylcarbonyl, cyclohexenylcarbonyl);
(22) a $C_{6-14}$ aryl-carbonyl group (e.g., benzoyl, 1-naphthylcarbonyl, 2-naphthylcarbonyl);
(23) a $C_{3-8}$ cycloalkyl-$C_{1-6}$ alkyl-carbonyl group (e.g., cyclopropylacetyl, 3-cyclopropylpropionyl, cyclobutylacetyl, cyclopentylacetyl, cyclohexylacetyl, cyclohexylpropionyl);
(24) a $C_{3-8}$ cycloalkenyl-$C_{1-6}$ alkyl-carbonyl group (e.g., cyclopentenylacetyl, cyclohexenylacetyl, 3-cyclohexenylpropionyl, 3-cyclohexenylpropionyl);
(25) a $C_{7-14}$ aralkyl-carbonyl group (e.g., phenylacetyl, 3-phenylpropionyl);
(26) a 5- or 6-membered monocyclic aromatic heterocyclyl-carbonyl group (e.g., furylcarbonyl, thienylcarbonyl, pyrrolylcarbonyl, oxazolylcarbonyl, isoxazolylcarbonyl, thiazolylcarbonyl, isothiazolylcarbonyl, imidazolylcarbonyl, pyridylcarbonyl, pyrazolylcarbonyl);
(27) an 8- to 12-membered fused aromatic heterocyclylcarbonyl group (e.g., benzofuranylcarbonyl, isobenzofuranylcarbonyl, benzothienylcarbonyl, isobenzothienylcarbonyl, indolylcarbonyl, isoindolylcarbonyl, indazolylcarbonyl, benzimidazolylcarbonyl, benzoxazolylcarbonyl);
(28) a 3- to 8-membered monocyclic non-aromatic heterocyclylcarbonyl group (e.g., oxiranylcarbonyl, azetidinylcarbonyl, oxetanylcarbonyl, thietanylcarbonyl, pyrrolidinylcarbonyl, tetrahydrofurylcarbonyl, thiolanylcarbonyl, piperidylcarbonyl);
(29) an 8- to 12-membered fused non-aromatic heterocyclylcarbonyl group (e.g., dihydrobenzofuranylcarbonyl);
(30) an amino group optionally mono- or di-substituted by substituent(s) selected from
(a) a $C_{1-6}$ alkyl group optionally having 1 to 3 halogen atoms,
(b) a $C_{1-6}$ alkyl-carbonyl group optionally having 1 to 3 halogen atoms,
(c) a $C_{3-8}$ cycloalkyl-carbonyl group,
(d) a $C_{6-14}$ aryl-carbonyl group optionally having 1 to 3 halogen atoms,
(e) a 5- or 6-membered monocyclic aromatic heterocyclylcarbonyl group,
(f) an 8- to 12-membered fused aromatic heterocyclylcarbonyl group,
(g) a 3- to 8-membered monocyclic non-aromatic heterocyclylcarbonyl group, and
(h) an 8- to 12-membered fused non-aromatic heterocyclylcarbonyl group;
(31) a sulfanyl group;
(32) a $C_{1-6}$ alkylsulfanyl group (e.g., methylsulfanyl, ethylsulfanyl);
(33) a $C_{2-6}$ alkenylsulfanyl group (e.g., vinylsulfanyl, propenylsulfanyl);
(34) a $C_{2-6}$ alkynylsulfanyl group (e.g., ethynylsulfanyl, propynylsulfanyl);
(35) a $C_{3-8}$ cycloalkylsulfanyl group (e.g., cyclopropylsulfanyl, cyclobutylsulfanyl);
(36) a $C_{3-8}$ cycloalkenylsulfanyl group (e.g., cyclopropenylsulfanyl, cyclobutenylsulfanyl);
(37) a $C_{6-14}$ arylsulfanyl group (e.g., phenylsulfanyl);

(38) a $C_{3-8}$ cycloalkyl-$C_{1-6}$ alkylsulfanyl group (e.g., cyclopropylmethylsulfanyl);
(39) a $C_{3-8}$ cycloalkenyl-$C_{1-6}$ alkylsulfanyl group (e.g., cyclopentenylmethylsulfanyl);
(40) a $C_{1-6}$ alkylsulfinyl group (e.g., methylsulfinyl, ethylsulfinyl);
(41) a $C_{2-6}$ alkenylsulfinyl group (e.g., vinylsulfinyl, propenylsulfinyl);
(42) a $C_{2-6}$ alkynylsulfinyl group (e.g., ethynylsulfinyl, propynylsulfinyl);
(43) a $C_{3-8}$ cycloalkylsulfinyl group (e.g., cyclopropylsulfinyl, cyclobutylsulfinyl);
(44) a $C_{3-8}$ cycloalkenylsulfinyl group (e.g., cyclopropenylsulfinyl, cyclobutenylsulfinyl);
(45) a $C_{6-14}$ arylsulfinyl group (e.g., phenylsulfinyl);
(46) a $C_{3-8}$ cycloalkyl-$C_{1-6}$ alkylsulfinyl group (e.g., cyclopropylmethylsulfinyl);
(47) a $C_{3-8}$ cycloalkenyl-$C_{1-6}$ alkylsulfinyl group (e.g., cyclopentenylmethylsulfinyl);
(48) a $C_{1-6}$ alkylsulfonyl group (e.g., methylsulfonyl, ethylsulfonyl);
(49) a $C_{2-8}$ alkenylsulfonyl group (e.g., vinylsulfonyl, propenylsulfonyl);
(50) a $C_{2-6}$ alkynylsulfonyl group (e.g., ethynylsulfonyl, propynylsulfonyl);
(51) a $C_{3-8}$ cycloalkylsulfonyl group (e.g., cyclopropylsulfonyl, cyclobutylsulfonyl);
(52) a $C_{3-8}$ cycloalkenylsulfonyl group (e.g., cyclopropenylsulfonyl, cyclobutenylsulfonyl);
(53) a $C_{6-14}$ arylsulfonyl group (e.g., phenylsulfonyl);
(54) a $C_{3-8}$ cycloalkyl-$C_{1-6}$ alkylsulfonyl group (e.g., cyclopropylmethylsulfonyl);
(55) a $C_{3-8}$ cycloalkenyl-$C_{1-6}$ alkylsulfonyl group (e.g., cyclopentenylmethylsulfonyl);
(56) a $C_{6-14}$ aryl-$C_{1-6}$ alkylsulfonyl group (e.g., benzylsulfonyl);
(57) a 5- or 6-membered monocyclic aromatic heterocyclylsulfonyl group (e.g., furylsulfonyl, thienylsulfonyl, pyridylsulfonyl);
(58) an 8- to 12-membered fused aromatic heterocyclylsulfonyl group (e.g., benzofuranylsulfonyl, isobenzofuranylsulfonyl);
(59) a 3- to 8-membered monocyclic non-aromatic heterocyclylsulfonyl group (e.g., oxiranylsulfonyl, azetidinylsulfonyl);
(60) an 8- to 12-membered fused non-aromatic heterocyclylsulfonyl group (e.g., dihydrobenzofuranylsulfonyl);
(61) a 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl) optionally substituted by 1 to 3 substituents selected from
  (a) a halogen atom,
  (b) a $C_{1-6}$ alkyl group optionally substituted by 1 to 3 halogen atoms, and
  (c) a $C_{1-6}$ alkoxy group optionally substituted by 1 to 3 halogen atoms;
(62) an 8- to 12-membered fused aromatic heterocyclic group (e.g., benzofuranyl, isobenzofuranyl, benzothienyl, isobenzothienyl, indolyl, isoindolyl, indazolyl, benzimidazolyl, benzoxazolyl) optionally substituted by 1 to 3 substituents selected from
  (a) a halogen atom,
  (b) a $C_{1-6}$ alkyl group optionally substituted by 1 to 3 halogen atoms, and
  (c) a $C_{1-6}$ alkoxy group optionally substituted by 1 to 3 halogen atoms;
(63) a 3- to 8-membered monocyclic non-aromatic heterocyclic group (e.g., oxiranyl, azetidinyl, oxetanyl, thietanyl, pyrrolidinyl, tetrahydrofuryl, thiolanyl, piperidyl, piperazinyl, dihydrooxadiazolyl, thiazolinyl) optionally substituted by 1 to 3 substituents selected from
  (a) a halogen atom,
  (b) a $C_{1-6}$ alkyl group optionally substituted by 1 to 3 halogen atoms,
  (c) a $C_{1-6}$ alkoxy group optionally substituted by 1 to 3 halogen atoms, and
  (d) an oxo group;
(64) an 8- to 12-membered fused non-aromatic heterocyclic group (e.g., dihydrobenzofuranyl) optionally substituted by 1 to 3 substituents selected from
  (a) a halogen atom,
  (b) a $C_{1-6}$ alkyl group optionally substituted by 1 to 3 halogen atoms,
  (c) a $C_{1-6}$ alkoxy group optionally substituted by 1 to 3 halogen atoms, and
  (d) an oxo group;
(65) a 5- or 6-membered monocyclic aromatic heterocyclyloxy group (e.g., furyloxy, thienyloxy, pyrrolyloxy, oxazolyloxy, isoxazolyloxy, thiazolyloxy, isothiazolyloxy, imidazolyloxy, pyridyloxy, pyrazolyloxy);
(66) an 8- to 12-membered fused aromatic heterocyclyloxy group (e.g., benzofuranyloxy, isobenzofuranyloxy, benzothienyloxy, isobenzothienyloxy, indolyloxy, isoindolyloxy, indazolyloxy, benzimidazolyloxy, benzoxazolyloxy);
(67) a 3- to 8-membered monocyclic non-aromatic heterocyclyloxy group (e.g., oxiranyloxy, azetidinyloxy, oxetanyloxy, thietanyloxy, pyrrolidinyloxy, tetrahydrofuryloxy, thiolanyloxy, piperidyloxy);
(68) an 8- to 12-membered fused non-aromatic heterocyclyloxy group (e.g., dihydrobenzofuranyloxy);
(69) a carboxy group;
(70) a $C_{1-6}$ alkoxy-carbonyl group;
(71) a $C_{2-6}$ alkenyloxy-carbonyl group (e.g., vinyloxycarbonyl, propenyloxycarbonyl, butenyloxycarbonyl, pentenyloxycarbonyl, hexenyloxycarbonyl);
(72) a $C_{2-6}$ alkynyloxy-carbonyl group (e.g., ethynyloxycarbonyl, propynyloxycarbonyl, butynyloxycarbonyl, pentynyloxycarbonyl, hexynyloxycarbonyl);
(73) a $C_{3-8}$ cycloalkyloxy-carbonyl group (e.g., cyclopropyloxycarbonyl, cyclobutyloxycarbonyl, cyclopentyloxycarbonyl, cyclohexyloxycarbonyl);
(74) a $C_{3-8}$ cycloalkenyloxy-carbonyl group (e.g., cyclopropenyloxycarbonyl, cyclobutenyloxycarbonyl, cyclopentenyloxycarbonyl, cyclohexenyloxycarbonyl);
(75) a $C_{6-14}$ aryloxy-carbonyl group (e.g., phenoxycarbonyl, 1-naphthyloxycarbonyl, 2-naphthyloxycarbonyl);
(76) a $C_{3-8}$ cycloalkyl-$C_{1-6}$ alkoxy-carbonyl group (e.g., cyclopropylmethyloxycarbonyl, cyclopropylethyloxycarbonyl, cyclobutyimethyloxycarbonyl, cyclopentylmethyloxycarbonyl, cyclohexylmethyloxycarbonyl, cyclohexylethyloxycarbonyl);
(77) a $C_{3-8}$ cycloalkenyl-$C_{1-6}$ alkoxy-carbonyl group (e.g., cyclopentenylmethyloxycarbonyl, cyclohexenylmethyloxycarbonyl, cyclohexenylethyloxycarbonyl, cyclohexenylpropyloxycarbonyl);
(78) a $C_{7-14}$ aralkyloxy-carbonyl group (e.g., benzyloxycarbonyl, phenethyloxycarbonyl);
(79) a mono-$C_{1-6}$ alkylthio-carbamoyl group (e.g., methylthiocarbamoyl, ethylthiocarbamoyl, propylthiocarbamoyl);
(80) a di-$C_{1-6}$ alkylthio-carbamoyl group (e.g., dimethylthiocarbamoyl, diethylthiocarbamoyl, dipropylthiocarbamoyl);

(81) a $C_{1-6}$ alkyl-carbonyloxy group (e.g., acetyloxy, propanoyloxy, butanoyloxy, 2-methylpropanoyloxy);
(82) an imino group optionally substituted by a hydroxy group; and
(83) a $C_{1-6}$ alkylenedioxy group (e.g., methylenedioxy, ethylenedioxy).

The $C_{3-10}$ cycloalkyl group, $C_{3-10}$ cycloalkenyl group, $C_{4-10}$ cycloalkadienyl group, $C_{6-14}$ aryl group, $C_{7-14}$ aralkyl group and $C_{8-13}$ arylalkenyl group, which are exemplified as the above-mentioned "hydrocarbon group", optionally have 1 to 3 substituents at substitutable position(s).

Examples of the substituent include substituents selected from the following Substituent Group B.
Substituent Group B:
(1) Substituent Group A;
(2) a $C_{1-6}$ alkyl group optionally substituted by 1 to 3 substituents selected from
　(a) a halogen atom,
　(b) a cyano group,
　(c) a hydroxy group,
　(d) a $C_{3-8}$ cycloalkyl group optionally substituted by 1 to 3 substituents selected from
　　(i) a halogen atom,
　　(ii) a cyano group, and
　　(iii) a $C_{1-6}$ alkyl group optionally substituted by 1 to 3 halogen atoms;
　(e) a $C_{6-14}$ aryl group optionally substituted by 1 to 3 substituents selected from
　　(i) a halogen atom,
　　(ii) a cyano group, and
　　(iii) a $C_{1-6}$ alkyl group optionally substituted by 1 to 3 halogen atoms,
　(f) a $C_{1-6}$ alkoxy group optionally substituted by 1 to 3 halogen atoms,
　(g) an amino group optionally mono- or di-substituted by $C_{1-6}$ alkyl group(s),
　(h) a 5- or 6-membered monocyclic aromatic heterocyclic group,
　(i) an 8- to 12-membered fused aromatic heterocyclic group,
　(j) a 3- to 8-membered monocyclic non-aromatic heterocyclic group,
　(k) an 8- to 12-membered fused non-aromatic heterocyclic group,
　(l) a carboxy group, and
　(m) a $C_{1-6}$ alkoxy-carbonyl group optionally substituted by 1 to 3 halogen atoms;
(3) a $C_{2-6}$ alkenyl group optionally substituted by 1 to 3 substituents selected from
　(a) a halogen atom,
　(b) a hydroxy group,
　(c) a $C_{1-6}$ alkoxy group,
　(d) an amino group optionally mono- or di-substituted by $C_{1-6}$ alkyl group(s),
　(e) a carboxy group, and
　(f) a $C_{1-6}$ alkoxy-carbonyl group; and
(4) a $C_{7-14}$ aralkyl group optionally substituted by 1 to 3 substituents selected from
　(a) a halogen atom,
　(b) a hydroxy group,
　(c) a $C_{1-6}$ alkoxy group, and
　(d) a $C_{1-6}$ alkyl group optionally substituted by 1 to 3 halogen atoms;
and the like. When the number of the substituents is two or more, the respective substituents may be the same or different.

Examples of the "heterocyclic group" of the above-mentioned "optionally substituted heterocyclic group" include an aromatic heterocyclic group and a non-aromatic heterocyclic group.

Examples of the aromatic heterocyclic group include a 4- to 7-membered (preferably 5- or 6-membered) monocyclic aromatic heterocyclic group containing, as a ring-constituting atom besides carbon atoms, 1 to 4 hetero atoms selected from an oxygen atom, a sulfur atom and a nitrogen atom, and a fused aromatic heterocyclic group. Examples of the fused aromatic heterocyclic group include a group derived from a fused ring wherein a ring corresponding to the 4- to 7-membered monocyclic aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are fused, and the like.

Preferable examples of the aromatic heterocyclic group include
monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like;
fused aromatic heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), thienopyridinyl (e.g., thieno[2,3-b]pyridin-3-yl), imidazopyrazinyl (e.g., 1H-imidazo[4,5-b]pyrazin-2-yl), pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl), pyridopyridinyl (e.g., pyrido[2,3-b]pyridin-3-yl), thienopyridyl (e.g., thieno[2,3-b]pyridin-3-yl) and the like;
and the like.

Examples of the non-aromatic heterocyclic group include a 4- to 7-membered (preferably 5- or 6-membered) monocyclic non-aromatic heterocyclic group containing, as a ring-constituting atom besides carbon atoms, 1 to 4 hetero atoms selected from an oxygen atom, a sulfur atom and a nitrogen atom, and a fused non-aromatic heterocyclic group.

Examples of the fused non-aromatic heterocyclic group include a group derived from a fused ring wherein a ring corresponding to the 4- to 7-membered monocyclic non-aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are fused, a group wherein the above-mentioned group is partially-saturated, and the like.

Preferable examples of the non-aromatic heterocyclic group include
monocyclic non-aromatic heterocyclic groups such as azetidinyl (e.g., 1-azetidinyl, 2-azetidinyl, 3-azetidinyl), pyrrolidinyl (e.g., 1-pyrrolidinyl, 2-pyrrolidinyl), piperidyl (e.g., piperidino, 2-piperidyl, 3-piperidyl, 4-piperidyl), morpholinyl (e.g., morpholino), thiomorpholinyl (e.g., thiomorpholino), piperazinyl (e.g., 1-piperazinyl, 2-piperazinyl, 3-piperazinyl), hexamethyleniminyl (e.g., hexamethylenimin-1-yl), oxazolidinyl (e.g., oxazolidin-2-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), tetrahydrofuryl (e.g., tetrahydrofuran-3-yl, tetrahydrofuran-2-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl) and the like; fused non-aromatic heterocyclic groups such as dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrahydro-1-benzofuran-3-yl), chromenyl (e.g., 4H-chromen-2-yl, 2H-chromen-3-yl), dihydrochromenyl (e.g., 3,4-dihydro-2H-chromen-2-yl), dihydroquinolyl (e.g., 1,2-dihydroquinolin-4-yl), tetrahydroquinolyl (e.g., 1,2,3,4-tetrahydroquinolin-4-yl), dihydroisoquinolyl (e.g., 1,2-dihydroisoquinolin-4-yl), tetrahydroisoquinolyl (e.g., 1,2,3,4-tetrahydroisoquinolin-4-yl), dihydrophthalazinyl (e.g., 1,4-dihydrophthalazin-4-yl) and the like;
and the like.

The above-mentioned "monocyclic non-aromatic heterocyclic group" and "fused non-aromatic heterocyclic group" may be bridged, and examples thereof include 3-oxa-6-azabicyclo[3.1.1]heptyl, 8-oxa-3-azabicyclo[3.2.1]octyl, 2-oxa-5-azabicyclo[2.2.1]heptyl, 3-oxa-8-azabicyclo[3.2.1]octyl, 6-oxa-3-azabicyclo[3.1.1]heptyl and the like.

The "heterocyclic group" of the above-mentioned "optionally substituted heterocyclic group" optionally has 1 to 3 substituents at substitutable position(s). Examples of the substituent include those similar to the above-mentioned Substituent Group B. When the heterocyclic group is a "non-aromatic heterocyclic group", the substituent further includes an oxo group. When the number of the substituents is two or more, the respective substituents may be the same or different.

Examples of the above-mentioned "optionally substituted hydroxy group" include a hydroxy group optionally substituted by a substituent selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a $C_{1-6}$ alkyl-carbonyl group, a heterocyclic group and the like, each optionally substituted.

Examples of the $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include those exemplified as the "hydrocarbon group" of the above-mentioned "optionally substituted hydrocarbon group".

Examples of the heterocyclic group include an "aromatic heterocyclic group" and a "non-aromatic heterocyclic group", which are exemplified as the "heterocyclic group" of the above-mentioned "optionally substituted heterocyclic group".

The above-mentioned $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group, $C_{1-6}$ alkyl-carbonyl group and heterocyclic group optionally have 1 to 3 substituents at substitutable position(s). When the number of the substituents is two or more, the respective substituents may be the same or different.

Examples of the substituent for the $C_{1-10}$ alkyl group, $C_{2-10}$ alkenyl group and $C_{1-6}$ alkyl-carbonyl group include those similar to the above-mentioned Substituent Group A.

Examples of the substituent for the $C_{3-10}$ cycloalkyl group, $C_{3-10}$ cycloalkenyl group, $C_{6-14}$ aryl group, $C_{7-14}$ aralkyl group and $C_{8-13}$ arylalkenyl group include those similar to the above-mentioned Substituent Group B. Examples of the substituent for the heterocyclic group include those similar to the substituent that the "heterocyclic group" of the above-mentioned "optionally substituted heterocyclic group" optionally has.

Examples of the "optionally substituted sulfanyl group" include a sulfanyl group optionally substituted by a substituent selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a $C_{1-6}$ alkyl-carbonyl group, a heterocyclic group and the like, each optionally substituted.

Examples of the substituent include those exemplified as the substituents of the above-mentioned "optionally substituted hydroxy group".

Examples of the above-mentioned "optionally substituted amino group" include an amino group optionally mono- or di-substituted by substituent(s) selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group and a heterocyclic group, each optionally substituted; an acyl group and the like.

Examples of the $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include those exemplified as the "hydrocarbon group" of the above-mentioned "optionally substituted hydrocarbon group".

Examples of the heterocyclic group include an "aromatic heterocyclic group" and a "non-aromatic heterocyclic group", which are exemplified as the "heterocyclic group" of the above-mentioned "optionally substituted heterocyclic group". Among them, a 5- to 7-membered monocyclic aromatic heterocyclic group is preferable.

The $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group and heterocyclic group optionally have 1 to 3 substituents at substitutable position(s). When the number of the substituents is two or more, the respective substituents may be the same or different.

Examples of the substituent for the $C_{1-10}$ alkyl group and $C_{2-10}$ alkenyl group include those similar to the above-mentioned Substituent Group A.

Examples of the substituent for the $C_{3-10}$ cycloalkyl group, $C_{3-10}$ cycloalkenyl group, $C_{6-14}$ aryl group, $C_{7-14}$ aralkyl group and $C_{8-13}$ arylalkenyl group include those similar to the above-mentioned Substituent Group B. Examples of the substituent for the heterocyclic group include those similar to the substituent that the "heterocyclic group" of the above-mentioned "optionally substituted heterocyclic group" optionally has.

Examples of the "acyl group" exemplified as the substituent for the "optionally substituted amino group" include those similar to the "acyl group" below, which is exemplified as the below-mentioned "substituent" represented by $R^4$.

Examples of the "acyl group" exemplified as the "substituent" represented by $R^4$ include a group represented by the formula: —$COR^A$, —CO—$OR^A$, —$SO_3R^A$, —$S(O)_2R^A$, —$SOR^A$, —CS—$NR^{A'}R^{B'}$ or —$S(O)_2NR^{A'}R^{B'}$ wherein $R^A$ is a hydrogen atom, an optionally substituted hydrocarbon group or an optionally substituted heterocyclic group, $R^{A'}$ and $R^{B'}$ are the same or different and each is a hydrogen atom, an optionally substituted hydrocarbon group or an optionally substituted heterocyclic group, or $R^{A'}$ and $R^{B'}$ in combination optionally form, together with the adjacent nitrogen atom, an optionally substituted nitrogen-containing heterocycle, and the like.

Examples of the "optionally substituted hydrocarbon group" and "optionally substituted heterocyclic group" represented by $R^A$, $R^{A'}$ or $R^{B'}$ include those similar to the "optionally substituted hydrocarbon group" and "optionally substituted heterocyclic group", which are exemplified as the "substituent" represented by $R^4$.

Examples of the "nitrogen-containing heterocycle" of the "optionally substituted nitrogen-containing heterocycle" formed by $R^{A'}$ and $R^{B'}$ in combination together with the adjacent nitrogen atom include a 5- to 7-membered nitrogen-containing heterocycle containing, as a ring-constituting atom besides carbon atoms, at least one nitrogen atom and optionally further containing one or two hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine and the like.

The nitrogen-containing heterocycle optionally has 1 to 5 (preferably 1 or 2) substituents at substitutable position(s). Examples of the substituent include those similar to the substituent that the "heterocyclic group" of the "optionally substituted heterocyclic group", which is exemplified as the "substituent" represented by $R^4$, optionally has. When the number of the substituents is two or more, the respective substituents may be the same or different.

Preferable examples of the "acyl group" include
(1) a formyl group;
(2) a carboxy group;
(3) a $C_{1-6}$ alkyl-carbonyl group (e.g., acetyl) optionally substituted by 1 to 3 halogen atoms;
(4) a $C_{1-6}$ alkoxy-carbonyl group (e.g., methoxycarbonyl, ethoxycarbonyl, propoxycarbonyl, tert-butoxycarbonyl) optionally substituted by 1 to 3 halogen atoms;
(5) a $C_{3-10}$ cycloalkyl-carbonyl group (e.g., cyclopropylcarbonyl, cyclopentylcarbonyl, cyclohexylcarbonyl);
(6) a $C_{6-14}$ aryl-carbonyl group (e.g., benzoyl, 1-naphthoyl, 2-naphthoyl) optionally substituted by 1 to 3 halogen atoms;
(7) a carbamoyl group optionally mono- or di-substituted by substituent(s) selected from
    (a) a $C_{1-6}$ alkyl group optionally substituted by 1 to 3 substituents selected from a halogen atom, a $C_{1-6}$ alkoxy group, a $C_{1-6}$ alkoxy-carbonyl group and a carboxy group, and
    (b) an amino group optionally mono- or di-substituted by $C_{1-6}$ alkoxy-carbonyl group(s);
(8) a $C_{1-6}$ alkylsulfonyl group (e.g., methylsulfonyl, ethylsulfonyl, isopropylsulfonyl) optionally substituted by 1 to 3 halogen atoms;
(9) a $C_{6-14}$ arylsulfonyl group (e.g., benzenesulfonyl);
(10) a sulfamoyl group;
(11) a thiocarbamoyl group;
(12) an aromatic heterocyclylcarbonyl group (e.g., furylcarbonyl, thienylcarbonyl) optionally substituted by 1 to 3 substituents selected from a $C_{1-6}$ alkyl group optionally substituted by 1 to 3 halogen atoms;
(13) a non-aromatic heterocyclylcarbonyl group (e.g., tetrahydrofurylcarbonyl, pyrrolidinocarbonyl) optionally substituted by 1 to 3 substituents selected from a $C_{1-6}$ alkyl group optionally substituted by 1 to 3 halogen atoms;
and the like.

$R^4$ is preferably H.

Z is preferably CH or N, more preferably CH.

In the formula (I), $R^1$ is an optionally substituted $C_{1-6}$ alkyl group, —CO—$R^2$, or —$SO_2$—$R^3$.

The "$C_{1-6}$ alkyl group" of the "optionally substituted $C_{1-6}$ alkyl group" represented by $R^1$ optionally has 1 to 3 substituents at substitutable position(s). Examples of the substituent include those similar to the above-mentioned Substituent Group A. When the number of the substituents is plural, the respective substituents may be the same or different.

In another embodiment, In the formula (I), $R^1$ is a substituted $C_{1-2}$ alkyl group, an optionally substituted $C_{3-6}$ alkyl group, —CO—$R^2$, or —$SO_2$—$R^3$.

The "substituted $C_{1-2}$ alkyl group" represented by $R^1$ has 1 to 2 (preferably 1) substituents at substitutable position(s). Examples of the substituent include substituents selected from the above-mentioned Substituent Group A. When the number of the substituents is plural, the respective substituents may be the same or different.

The "$C_{3-6}$ alkyl group" of the "optionally substituted $C_{3-6}$ alkyl group" represented by $R^1$ optionally has 1 to 5 (preferably 1 to 3) substituents at substitutable position(s). Examples of the substituent include substituents selected from the above-mentioned Substituent Group A. When the number of the substituents is plural, the respective substituents may be the same or different.

In the formula (I), $R^2$ is an optionally substituted $C_{1-6}$ alkyl group, an optionally substituted $C_{1-6}$ alkoxy group, an optionally substituted $C_{6-14}$ aryl group, or an optionally substituted $C_{3-8}$ cycloalkyl group.

The "$C_{1-6}$ alkyl group" of the "optionally substituted $C_{1-6}$ alkyl group" represented by $R^2$ optionally has 1 to 5 (preferably 1 to 3) substituents at substitutable position(s). Examples of the substituent include substituents selected from the above-mentioned Substituent Group A. When the number of the substituents is plural, the respective substituents may be the same or different.

The "$C_{1-6}$ alkoxy group" of the "optionally substituted $C_{1-6}$ alkoxy group" represented by $R^2$ optionally has 1 to 5

(preferably 1 to 3) substituents at substitutable position(s). Examples of the substituent include substituents selected from the above-mentioned Substituent Group A. When the number of the substituents is plural, the respective substituents may be the same or different.

The "$C_{6-14}$ aryl group" of the "optionally substituted $C_{6-14}$ aryl group" represented by $R^2$ optionally has 1 to 5 (preferably 1 to 3) substituents at substitutable position(s). Examples of the substituent include substituents selected from the above-mentioned Substituent Group B. When the number of the substituents is plural, the respective substituents may be the same or different.

The "$C_{3-8}$ cycloalkyl group" of the "optionally substituted $C_{3-8}$ cycloalkyl group" represented by $R^2$ optionally has 1 to 5 (preferably 1 to 3) substituents at substitutable position(s). Examples of the substituent include substituents selected from the above-mentioned Substituent Group B and an oxo group. When the number of the substituents is plural, the respective substituents may be the same or different.

In the formula (I), $R^3$ is a substituent.

Examples of the "substituent" represented by $R^3$ include those similar to the "substituent" represented by $R^4$ $R^1$ is preferably (1) a $C_{1-6}$ alkyl group (e.g., methyl, ethyl) optionally substituted by 1 to 3 substituents (preferably substituted by 1 to 3 substituents) selected from
  (i) a $C_{6-14}$ aryl group (e.g., phenyl) optionally substituted by 1 to 3 substituents selected from
    (a) a $C_{1-6}$ alkoxy group (e.g., methoxy),
    (b) a cyano group, and
    (c) a halogen atom (e.g., a fluorine atom),
  (ii) a heterocyclic group (e.g., pyridyl, imidazolyl, oxazolyl, pyrazolyl, tetrahydrofuryl, isoxazolyl, pyrimidinyl, pyrazinyl, thiazolyl) optionally substituted by 1 to 3 $C_{1-6}$ alkyl groups (e.g., methyl),
  (iii) a $C_{3-8}$ cycloalkyl group (e.g., cyclopropyl),
  (iv) a mono- or di-$C_{1-6}$ alkyl-carbamoyl group (e.g., dimethylcarbamoyl, diethylcarbamoyl), and
  (v) a heterocyclylcarbonyl group (e.g., pyrrolidinylcarbonyl, morpholinylcarbonyl, azetidinylcarbonyl),
(2) —CO—$R^2$ wherein $R^2$ is
  (i) a $C_{1-6}$ alkyl group (e.g., methyl) optionally substituted by 1 to 3 substituents selected from
    (a) a $C_{8-14}$ aryl group (e.g., phenyl) optionally substituted by 1 to 3 $C_{1-8}$ alkoxy groups (e.g., methoxy), and
    (b) a $C_{3-8}$ cycloalkyl group (e.g., cyclopropyl),
  (ii) a $C_{1-8}$ alkoxy group (e.g., tert-butoxy),
  (iii) a $C_{8-14}$ aryl group (e.g., phenyl), or
  (iv) a $C_{3-8}$ cycloalkyl group (e.g., cyclopropyl), or
(3) —SO$_2$—$R^3$ wherein $R^3$ is
  (i) a $C_{1-8}$ alkyl group (e.g., methyl, ethyl, isopropyl) optionally substituted by 1 to 3 halogen atoms (e.g., a fluorine atom),
  (ii) a $C_{3-8}$ cycloalkyl group (e.g., cyclopropyl),
  (iii) a $C_{8-14}$ aryl group (e.g., phenyl) optionally substituted by 1 to 3 substituents selected from
    (a) a $C_{1-8}$ alkoxy group (e.g., methoxy), and
    (b) a halogen atom (e.g., a fluorine atom),
  (iv) a heterocyclic group (e.g., pyrazolyl, morpholinyl, pyridyl) optionally substituted by 1 to 3 $C_{1-8}$ alkyl groups (e.g., methyl), or
  (v) a mono- or di-$C_{1-6}$ alkyl-amino group (e.g., dimethylamino).

$R^1$ is more preferably (1) a $C_{1-8}$ alkyl group (e.g., methyl) optionally substituted by 1 to 3 substituents (preferably substituted by 1 to 3 substituents) selected from
  (i) a $C_{8-14}$ aryl group (e.g., phenyl) optionally substituted by 1 to 3 substituents selected from
    (a) a $C_{1-8}$ alkoxy group (e.g., methoxy), and
    (b) a halogen atom (e.g., a fluorine atom),
  (ii) a heterocyclic group (preferably an aromatic heterocyclic group (e.g., pyridyl, imidazolyl, pyrazolyl, thiazolyl)) optionally substituted by 1 to 3 $C_{1-6}$ alkyl groups (e.g., methyl),
  (iii) a mono- or di-$C_{1-6}$ alkyl-carbamoyl group (e.g., dimethylcarbamoyl, diethylcarbamoyl), and
  (iv) a heterocyclylcarbonyl group (e.g., morpholinylcarbonyl),
(2) —CO—$R^2$ wherein $R^2$ is
  (i) a $C_{1-6}$ alkyl group (e.g., methyl) optionally substituted by 1 to 3 substituents selected from a $C_{6-14}$ aryl group (e.g., phenyl) optionally substituted by 1 to 3 $C_{1-6}$ alkoxy groups (e.g., methoxy), or
  (ii) a $C_{3-8}$ cycloalkyl group (e.g., cyclopropyl), or
(3) —SO$_2$—$R^3$ wherein $R^3$ is
  (i) a $C_{1-6}$ alkyl group (e.g., ethyl),
  (ii) a $C_{6-14}$ aryl group (e.g., phenyl) optionally substituted by 1 to 3 substituents selected from
    (a) a $C_{1-6}$ alkoxy group (e.g., methoxy), and
    (b) a halogen atom (e.g., a fluorine atom), or
  (iii) a heterocyclic group (e.g., pyrazolyl, morpholinyl) optionally substituted by 1 to 3 $C_{1-6}$ alkyl groups (e.g., methyl).

$R^1$ is further more preferably (1) a $C_{1-6}$ alkyl group (e.g., methyl) optionally substituted by 1 to 3 substituents (preferably substituted by 1 to 3 substituents) selected from
  (i) a $C_{6-14}$ aryl group (e.g., phenyl).
  (ii) a heterocyclic group (preferably an aromatic heterocyclic group (e.g., pyrazolyl, thiazolyl)) optionally substituted by 1 to 3 $C_{1-6}$ alkyl groups (e.g., methyl), and
  (iii) a mono- or di-$C_{1-6}$ alkyl-carbamoyl group (e.g., dimethylcarbamoyl), or
(2) —SO$_2$—$R^3$ wherein $R^3$ is a $C_{6-14}$ aryl group (e.g., phenyl) optionally substituted by 1 to 3 $C_{1-6}$ alkoxy groups (e.g., methoxy).

In another embodiment, $R^1$ is further more preferably (1) a $C_{1-6}$ alkyl group (e.g., methyl) optionally substituted by 1 to 3 substituents (preferably substituted by 1 to 3 substituents) selected from
  (i) a heterocyclic group (e.g., pyrazolyl, thiazolyl) optionally substituted by 1 to 3 $C_{1-6}$ alkyl groups (e.g., methyl), and
  (ii) a mono- or di-$C_{1-6}$ alkyl-carbamoyl group (e.g., dimethylcarbamoyl), or
(2) —SO$_2$—$R^3$ wherein $R^3$ is a heterocyclic group (e.g., pyrazolyl) optionally substituted by 1 to 3 $C_{1-6}$ alkyl groups (e.g., methyl).

$R^1$ is particularly preferably (1) a $C_{1-6}$ alkyl group (e.g., methyl) optionally substituted by 1 to 3 substituents (preferably substituted by 1 to 3 substituents) selected from
  (i) a heterocyclic group (preferably an aromatic heterocyclic group (e.g., pyrazolyl, thiazolyl, preferably pyrazolyl)) optionally substituted by 1 to 3 $C_{1-6}$ alkyl groups (e.g., methyl), and
  (ii) a mono- or di-$C_{1-6}$ alkyl-carbamoyl group (e.g., dimethylcarbamoyl), or (2) —SO$_2$—R$^3$ wherein R$^3$ is a C$_{6-14}$ aryl group (e.g., phenyl) optionally substituted by 1 to 3 C$_{1-6}$ alkoxy groups (e.g., methoxy).

In the formula (I), n is 0 or 1.

In the formula (I), Ring A is a 5- or 6-membered nitrogen-containing heterocycle optionally further substituted by 1 to 3 substituents selected from a halogen atom, an acyl group, an optionally substituted C$_{1-6}$ alkyl group, an optionally substituted hydroxy group, an optionally substituted sulfanyl group, an optionally substituted amino group and an oxo group.

Examples of the "5- or 6-membered nitrogen-containing heterocycle" in Ring A include a 5- or 6-membered nitrogen-containing heterocycle containing, as a ring-constituting atom besides carbon atoms, at least one nitrogen atom and optionally further containing one or two hetero atoms selected from an oxygen atom, a sulfur atom and a nitrogen atom. Preferable examples of the 5- or 6-membered nitrogen-containing heterocycle include a pyrrolidine ring, an imidazolidine ring, a pyrazolidine ring, a piperidine ring, a piperazine ring, a morpholine ring, a thiomorpholine ring and the like. The "5- or 6-membered nitrogen-containing heterocycle" in Ring A is preferably a pyrrolidine ring, an imidazolidine ring, a piperidine ring or a piperazine ring, particularly preferably a pyrrolidine ring, a piperidine ring or a piperazine ring.

Examples of the "acyl group", "optionally substituted hydroxy group", "optionally substituted sulfanyl group" and "optionally substituted amino group", which are the substituents for the "5- or 6-membered nitrogen-containing heterocycle" in Ring A, include those similar to the "acyl group", "optionally substituted hydroxy group", "optionally substituted sulfanyl group" and "optionally substituted amino group", which are exemplified as the "substituent" represented by R$^4$, respectively.

The "C$_{1-6}$ alkyl group" of the "optionally substituted C$_{1-6}$ alkyl group", which is the substituent for the "5- or 6-membered nitrogen-containing heterocycle" in Ring A, optionally has 1 to 5 (preferably 1 to 3) substituents at substitutable position(s). Examples of the substituent include substituents selected from the above-mentioned Substituent Group A. When the number of the substituents is plural, the respective substituents may be the same or different.

Ring A is preferably a 5- or 6-membered nitrogen-containing heterocycle (preferably a 5- or 6-membered nitrogen-containing non-aromatic heterocycle (e.g., pyrrolidine, piperidine, piperazine)) optionally further substituted by 1 to 3 substituents selected from (1) a halogen atom (e.g., a fluorine atom), and (2) an oxo group.

Ring A is more preferably a 5- or 6-membered nitrogen-containing heterocycle (preferably a 5- or 6-membered nitrogen-containing non-aromatic heterocycle (e.g., pyrrolidine, piperidine)) optionally further substituted by 1 to 3 halogen atoms (e.g., a fluorine atom).

In the formula (I), Ring B is a 6-membered aromatic ring optionally further substituted by 1 to 3 substituents selected from a halogen atom, a cyano group, an acyl group, an optionally substituted C$_{1-6}$ alkyl group, an optionally substituted hydroxy group, an optionally substituted sulfanyl group, and an optionally substituted amino group.

Examples of the "6-membered aromatic ring" in Ring B include benzene and a 6-membered aromatic heterocycle (e.g., pyridine, pyridazine, pyrimidine, pyrazine, triazine). The "6-membered aromatic ring" in Ring B is preferably a benzene ring, a pyridine ring, a pyrimidine ring or a pyrazine ring, more preferably a benzene ring, a pyridine ring or a pyrazine ring, particularly preferably a pyridine ring or a pyrazine ring.

Examples of the "acyl group", "optionally substituted hydroxy group", "optionally substituted sulfanyl group" and "optionally substituted amino group", which are the substituents for the "6-membered aromatic ring" in Ring B, include those similar to the "acyl group", "optionally substituted hydroxy group", "optionally substituted sulfanyl group" and "optionally substituted amino group", which are exemplified as the "substituent" represented by R$^4$, respectively.

The "C$_{1-6}$ alkyl group" of the "optionally substituted C$_{1-6}$ alkyl group", which is the substituent for the "6-membered aromatic ring" in Ring B, optionally has 1 to 5 (preferably 1 to 3) substituents at substitutable position(s). Examples of the substituent include substituents selected from the above-mentioned Substituent Group A. When the number of the substituents is plural, the respective substituents may be the same or different.

Ring B is preferably a 6-membered aromatic ring optionally further substituted by 1 to 3 substituents selected from a halogen atom, a cyano group and an optionally substituted C$_{1-6}$ alkyl group.

Ring B is more preferably a 6-membered aromatic ring (e.g., benzene, pyridine, pyrimidine, pyrazine) optionally further substituted by 1 to 3 substituents selected from (1) a halogen atom (e.g., a fluorine atom, a chlorine atom), (2) a cyano group, and (3) a C$_{1-6}$ alkyl group (e.g., methyl) optionally substituted by 1 to 3 halogen atoms (e.g., a fluorine atom).

Ring B is further more preferably a 6-membered aromatic ring (e.g., benzene, pyridine, pyrazine) optionally further substituted by 1 to 3 substituents selected from (1) a halogen atom (e.g., a fluorine atom), and (2) a C$_{1-6}$ alkyl group (e.g., methyl).

Ring B is still more preferably a 6-membered aromatic ring (e.g., benzene, pyridine, pyrazine), particularly preferably a 6-membered aromatic heterocycle (e.g., pyridine or pyrazine).

Preferable examples of compound (I) include the following compounds.

[Compound A-1]

Compound (I) wherein

X is a carbon atom or a nitrogen atom;

Y is —O—, —CH$_2$—, —CO— or —SO$_2$—;

Z is CH or N;

R$^1$ is an optionally substituted C$_{1-6}$ alkyl group, —CO—R$^2$, or —SO$_2$—R$^3$;

R$^2$ is an optionally substituted C$_{1-6}$ alkyl group, an optionally substituted C$_{1-6}$ alkoxy group, an optionally substituted C$_{6-14}$ aryl group, or an optionally substituted C$_{3-8}$ cycloalkyl group;

R$^3$ is a substituent;

n is 0 or 1;

Ring A is a 5- or 6-membered nitrogen-containing heterocycle optionally further substituted by 1 to 3 substituents selected from a halogen atom and an oxo group; and Ring B is a 6-membered aromatic ring optionally further substituted by 1 to 3 substituents selected from a halogen atom, a cyano group and an optionally substituted C$_{1-6}$ alkyl group, provided that (4-ethylpiperazin-1-yl) (2-(pyrimidin-4-yl)phenyl)methanone, and (4-methylpiperazin-1-yl) (2-(pyrimidin-4-yl)phenyl)methanone are excluded.

[Compound A-2]
Compound (I) wherein
X is a carbon atom or a nitrogen atom;
Y is —O—, —CH$_2$—, —CO— or —SO$_2$—;
Z is CH or N;
R$^1$ is a substituted C$_{1-2}$ alkyl group, an optionally substituted C$_{3-6}$ alkyl group, —CO—R$^2$, or —SO$_2$—R$^3$;
R$^2$ is an optionally substituted C$_{1-6}$ alkyl group, an optionally substituted C$_{1-6}$ alkoxy group, an optionally substituted C$_{6-14}$ aryl group, or an optionally substituted C$_{3-8}$ cycloalkyl group; R$^3$ is a substituent;
n is 0 or 1;
Ring A is a 5- or 6-membered nitrogen-containing heterocycle optionally further substituted by 1 to 3 substituents selected from a halogen atom and an oxo group; and
Ring B is a 6-membered aromatic ring optionally further substituted by 1 to 3 substituents selected from a halogen atom, a cyano group and an optionally substituted C$_{1-6}$ alkyl group.

[Compound B-1]
Compound (I) wherein
X is a carbon atom or a nitrogen atom;
Y is —O—, —CH$_2$—, —CO— or —SO$_2$—;
Z is CH or N;
R$^1$ is
(1) a C$_{1-6}$ alkyl group (e.g., methyl, ethyl) optionally substituted by 1 to 3 substituents selected from
    (i) a C$_{6-14}$ aryl group (e.g., phenyl) optionally substituted by 1 to 3 substituents selected from
        (a) a C$_{1-6}$ alkoxy group (e.g., methoxy),
        (b) a cyano group, and
        (c) a halogen atom (e.g., a fluorine atom),
    (ii) a heterocyclic group (e.g., pyridyl, imidazolyl, oxazolyl, pyrazolyl, tetrahydrofuryl, isoxazolyl, pyrimidinyl, pyrazinyl, thiazolyl) optionally substituted by 1 to 3 C$_{1-6}$ alkyl groups (e.g., methyl),
    (iii) a C$_{3-8}$ cycloalkyl group (e.g., cyclopropyl),
    (iv) a mono- or di-C$_{1-6}$ alkyl-carbamoyl group (e.g., dimethylcarbamoyl, diethylcarbamoyl), and
    (v) a heterocyclylcarbonyl group (e.g., pyrrolidinylcarbonyl, morpholinylcarbonyl, azetidinylcarbonyl),
(2) —CO—R$^2$ wherein R$^2$ is
    (i) a C$_{1-6}$ alkyl group (e.g., methyl) optionally substituted by 1 to 3 substituents selected from
        (a) a C$_{6-14}$ aryl group (e.g., phenyl) optionally substituted by 1 to 3 C$_{1-6}$ alkoxy groups (e.g., methoxy), and
        (b) a C$_{3-8}$ cycloalkyl group (e.g., cyclopropyl),
    (ii) a C$_{1-6}$ alkoxy group (e.g., tert-butoxy),
    (iii) a C$_{6-14}$ aryl group (e.g., phenyl), or
    (iv) a C$_{3-8}$ cycloalkyl group (e.g., cyclopropyl), or
(3) —SO$_2$—R$^3$ wherein R$^3$ is
    (i) a C$_{1-6}$ alkyl group (e.g., methyl, ethyl, isopropyl) optionally substituted by 1 to 3 halogen atoms (e.g., a fluorine atom),
    (ii) a C$_{3-8}$ cycloalkyl group (e.g., cyclopropyl),
    (iii) a C$_{6-14}$ aryl group (e.g., phenyl) optionally substituted by 1 to 3 substituents selected from
        (a) a C$_{1-6}$ alkoxy group (e.g., methoxy), and
        (b) a halogen atom (e.g., a fluorine atom),
    (iv) a heterocyclic group (e.g., pyrazolyl, morpholinyl, pyridyl) optionally substituted by 1 to 3 C$_{1-6}$ alkyl groups (e.g., methyl), or
    (v) a mono- or di-C$_{1-6}$ alkyl-amino group (e.g., dimethylamino);
n is 0 or 1;

Ring A is a 5- or 6-membered nitrogen-containing heterocycle (preferably a 5- or 6-membered nitrogen-containing non-aromatic heterocycle (e.g., pyrrolidine, piperidine, piperazine)) optionally further substituted by 1 to 3 substituents selected from
    (1) a halogen atom (e.g., a fluorine atom), and
    (2) an oxo group; and
Ring B is a 6-membered aromatic ring (e.g., benzene, pyridine, pyrimidine, pyrazine) optionally further substituted by 1 to 3 substituents selected from
    (1) a halogen atom (e.g., a fluorine atom, a chlorine atom),
    (2) a cyano group, and
    (3) a C$_{1-6}$ alkyl group (e.g., methyl) optionally substituted by 1 to 3 halogen atoms (e.g., a fluorine atom),
provided that (4-ethylpiperazin-1-yl)(2-(pyrimidin-4-yl)phenyl)methanone, and (4-methylpiperazin-1-yl) (2-(pyrimidin-4-yl)phenyl)methanone are excluded.

[Compound B-2]
Compound (I) wherein
X is a carbon atom or a nitrogen atom;
Y is —O—, —CH$_2$—, —CO— or —SO$_2$—;
Z is CH or N;
R$^1$ is
(1) a C$_{1-6}$ alkyl group (e.g., methyl, ethyl) optionally substituted by 1 to 3 substituents selected from
    (i) a C$_{6-14}$ aryl group (e.g., phenyl) optionally substituted by 1 to 3 substituents selected from
        (a) a C$_{1-6}$ alkoxy group (e.g., methoxy),
        (b) a cyano group, and
        (c) a halogen atom (e.g., a fluorine atom),
    (ii) a pyridyl group, an imidazolyl group, an oxazolyl group, a pyrazolyl group, a tetrahydrofuryl group, an isoxazolyl group, a pyrimidinyl group, a pyrazinyl group and a thiazolyl group, each optionally substituted by 1 to 3 C$_{1-6}$ alkyl groups (e.g., methyl),
    (iii) a C$_{3-8}$ cycloalkyl group (e.g., cyclopropyl),
    (iv) a mono- or di-C$_{1-6}$ alkyl-carbamoyl group (e.g., dimethylcarbamoyl, diethylcarbamoyl), and
    (v) a pyrrolidinylcarbonyl group, a morpholinylcarbonyl group and an azetidinylcarbonyl group,
(2) —CO—R$^2$ wherein R$^2$ is
    (i) a C$_{1-6}$ alkyl group (e.g., methyl) optionally substituted by 1 to 3 substituents selected from
        (a) a C$_{6-14}$ aryl group (e.g., phenyl) optionally substituted by 1 to 3 C$_{1-6}$ alkoxy groups (e.g., methoxy), and
        (b) a C$_{3-8}$ cycloalkyl group (e.g., cyclopropyl),
    (ii) a C$_{1-6}$ alkoxy group (e.g., tert-butoxy),
    (iii) a C$_{6-14}$ aryl group (e.g., phenyl), or
    (iv) a C$_{3-6}$ cycloalkyl group (e.g., cyclopropyl), or
(3) —SO$_2$—R$^3$ wherein R$^3$ is
    (i) a C$_{1-6}$ alkyl group (e.g., methyl, ethyl, isopropyl) optionally substituted by 1 to 3 halogen atoms (e.g., a fluorine atom),
    (ii) a C$_{3-6}$ cycloalkyl group (e.g., cyclopropyl),
    (iii) a C$_{6-14}$ aryl group (e.g., phenyl) optionally substituted by 1 to 3 substituents selected from
        (a) a C$_{1-6}$ alkoxy group (e.g., methoxy), and
        (b) a halogen atom (e.g., a fluorine atom),
    (iv) a pyrazolyl group, a morpholinyl group or a pyridyl group, each optionally substituted by 1 to 3 C$_{1-6}$ alkyl groups (e.g., methyl), or
    (v) a mono- or di-C$_{1-6}$ alkyl-amino group (e.g., dimethylamino);
n is 0 or 1;

Ring A is a pyrrolidine ring, a piperidine ring or a piperazine ring, each optionally further substituted by 1 to 3 substituents selected from
(1) a halogen atom (e.g., a fluorine atom), and
(2) an oxo group; and
Ring B is a benzene ring, a pyridine ring, a pyrimidine ring or a pyrazine ring, each optionally further substituted by 1 to 3 substituents selected from
(1) a halogen atom (e.g., a fluorine atom, a chlorine atom),
(2) a cyano group, and
(3) a $C_{1-5}$ alkyl group (e.g., methyl) optionally substituted by 1 to 3 halogen atoms (e.g., a fluorine atom),
provided that (4-ethylpiperazin-1-yl)(2-(pyrimidin-4-yl)phenyl)methanone, and (4-methylpiperazin-1-yl) (2-(pyrimidin-4-yl)phenyl)methanone are excluded.

[Compound B-3]
Compound (I) wherein
X is a carbon atom or a nitrogen atom;
Y is —O—, —CH$_2$—, —CO— or —SO$_2$—;
Z is CH or N;
$R^1$ is
(1) a $C_{1-6}$ alkyl group (e.g., methyl, ethyl) optionally substituted by 1 to 3 substituents selected from
  (i) a phenyl group optionally substituted by 1 to 3 substituents selected from
    (a) a $C_{1-6}$ alkoxy group (e.g., methoxy),
    (b) a cyano group, and
    (c) a halogen atom (e.g., a fluorine atom),
  (ii) a pyridyl group, an imidazolyl group, an oxazolyl group, a pyrazolyl group, a tetrahydrofuryl group, an isoxazolyl group, a pyrimidinyl group, a pyrazinyl group and a thiazolyl group, each optionally substituted by 1 to 3 $C_{1-6}$ alkyl groups (e.g., methyl),
  (iii) a cyclopropyl group,
  (iv) a mono- or di-$C_{1-6}$ alkyl-carbamoyl group (e.g., dimethylcarbamoyl, diethylcarbamoyl), and
  (v) a pyrrolidinylcarbonyl group, a morpholinylcarbonyl group and an azetidinylcarbonyl group,
(2) —CO—$R^2$ wherein $R^2$ is
  (i) a $C_{1-5}$ alkyl group (e.g., methyl) optionally substituted by 1 to 3 substituents selected from
    (a) a phenyl group optionally substituted by 1 to 3 $C_{1-6}$ alkoxy groups (e.g., methoxy), and
    (b) a cyclopropyl group,
  (ii) a $C_{1-6}$ alkoxy group (e.g., tert-butoxy),
  (iii) a phenyl group, or
  (iv) a cyclopropyl group, or
(3) —SO$_2$—$R^3$ wherein $R^3$ is
  (i) a $C_{1-6}$ alkyl group (e.g., methyl, ethyl, isopropyl) optionally substituted by 1 to 3 halogen atoms (e.g., a fluorine atom),
  (ii) a cyclopropyl group,
  (iii) a phenyl group optionally substituted by 1 to 3 substituents selected from
    (a) a $C_{1-6}$ alkoxy group (e.g., methoxy), and
    (b) a halogen atom (e.g., a fluorine atom),
  (iv) a pyrazolyl group, a morpholinyl group or a pyridyl group, each optionally substituted by 1 to 3 $C_{1-6}$ alkyl groups (e.g., methyl), or
  (v) a mono- or di-$C_{1-6}$ alkyl-amino group (e.g., dimethylamino);
n is 0 or 1;
Ring A is a pyrrolidine ring, a piperidine ring or a piperazine ring, each optionally further substituted by 1 to 3 substituents selected from
(1) a halogen atom (e.g., a fluorine atom), and
(2) an oxo group; and
Ring B is a benzene ring, a pyridine ring, a pyrimidine ring or a pyrazine ring, each optionally further substituted by 1 to 3 substituents selected from
(1) a halogen atom (e.g., a fluorine atom, a chlorine atom),
(2) a cyano group, and
(3) a $C_{1-6}$ alkyl group (e.g., methyl) optionally substituted by 1 to 3 halogen atoms (e.g., a fluorine atom),
provided that (4-ethylpiperazin-1-yl)(2-(pyrimidin-4-yl)phenyl)methanone, and (4-methylpiperazin-1-yl) (2-(pyrimidin-4-yl)phenyl)methanone are excluded.

[Compound B-4]
Compound (I) wherein
X is a carbon atom or a nitrogen atom;
Y is —O—, —CH$_2$—, —CO— or —SO$_2$—;
Z is CH or N;
$R^1$ is
(1) a $C_{1-6}$ alkyl group (e.g., methyl) substituted by 1 to 3 substituents selected from
  (i) a phenyl group optionally substituted by 1 to 3 substituents selected from
    (a) a $C_{1-6}$ alkoxy group (e.g., methoxy),
    (b) a cyano group, and
    (c) a halogen atom (e.g., a fluorine atom),
  (ii) a pyridyl group, an imidazolyl group, an oxazolyl group, a pyrazolyl group, a tetrahydrofuryl group, an isoxazolyl group, a pyrimidinyl group, a pyrazinyl group and a thiazolyl group, each optionally substituted by 1 to 3 $C_{1-6}$ alkyl groups (e.g., methyl),
  (iii) a cyclopropyl group,
  (iv) a mono- or di-$C_{1-6}$ alkyl-carbamoyl group (e.g., dimethylcarbamoyl, diethylcarbamoyl), and
  (v) a pyrrolidinylcarbonyl group, a morpholinylcarbonyl group and an azetidinylcarbonyl group,
(2) —CO—$R^2$ wherein $R^2$ is
  (i) a $C_{1-6}$ alkyl group (e.g., methyl) optionally substituted by 1 to 3 substituents selected from
    (a) a phenyl group optionally substituted by 1 to 3 $C_{1-6}$ alkoxy groups (e.g., methoxy), and
    (b) a cyclopropyl group,
  (ii) a $C_{1-6}$ alkoxy group (e.g., tert-butoxy),
  (iii) a phenyl group, or
  (iv) a cyclopropyl group, or
(3) —SO$_2$—$R^3$ wherein $R^3$ is
  (i) a $C_{1-6}$ alkyl group (e.g., methyl, ethyl, isopropyl) optionally substituted by 1 to 3 halogen atoms (e.g., a fluorine atom),
  (ii) a cyclopropyl group,
  (iii) a phenyl group optionally substituted by 1 to 3 substituents selected from
    (a) a $C_{1-6}$ alkoxy group (e.g., methoxy), and
    (b) a halogen atom (e.g., a fluorine atom),
  (iv) a pyrazolyl group, a morpholinyl group or a pyridyl group, each optionally substituted by 1 to 3 $C_{1-6}$ alkyl groups (e.g., methyl), or
  (v) a mono- or di-$C_{1-6}$ alkyl-amino group (e.g., dimethylamino);
n is 0 or 1;
Ring A is a pyrrolidine ring, a piperidine ring or a piperazine ring, each optionally further substituted by 1 to 3 substituents selected from
(1) a halogen atom (e.g., a fluorine atom), and
(2) an oxo group; and
Ring B is a benzene ring, a pyridine ring, a pyrimidine ring or a pyrazine ring, each optionally further substituted by 1 to 3 substituents selected from (1) a halogen atom (e.g., a fluorine atom, a chlorine atom),
(2) a cyano group, and
(3) a $C_{1-6}$ alkyl group (e.g., methyl) optionally substituted by 1 to 3 halogen atoms (e.g., a fluorine atom).

[Compound C-1]

Compound (I) wherein

X is a carbon atom or a nitrogen atom;

Y is —O—, —CH$_2$—, —CO— or —SO$_2$—;

Z is CH or N;

$R^1$ is (1) a $C_{1-6}$ alkyl group (e.g., methyl) optionally substituted by 1 to 3 substituents selected from
- (i) a $C_{6-14}$ aryl group (e.g., phenyl) optionally substituted by 1 to 3 substituents selected from
  - (a) a $C_{1-6}$ alkoxy group (e.g., methoxy), and
  - (b) a halogen atom (e.g., a fluorine atom),
- (ii) a heterocyclic group (preferably an aromatic heterocyclic group (e.g., pyridyl, imidazolyl, pyrazolyl, thiazolyl)) optionally substituted by 1 to 3 $C_{1-6}$ alkyl groups (e.g., methyl),
- (iii) a mono- or di-$C_{1-6}$ alkyl-carbamoyl group (e.g., dimethylcarbamoyl, diethylcarbamoyl), and
- (iv) a heterocyclylcarbonyl group (e.g., morpholinylcarbonyl), (2) —CO—$R^2$ wherein $R^2$ is
- (i) a $C_{1-6}$ alkyl group (e.g., methyl) optionally substituted by 1 to 3 substituents selected from a $C_{6-14}$ aryl group (e.g., phenyl) optionally substituted by 1 to 3 $C_{1-6}$ alkoxy groups (e.g., methoxy), or
- (ii) a $C_{3-8}$ cycloalkyl group (e.g., cyclopropyl), or (3) —SO$_2$—$R^3$ wherein $R^3$ is
- (i) a $C_{1-6}$ alkyl group (e.g., ethyl),
- (ii) a $C_{6-14}$ aryl group (e.g., phenyl) optionally substituted by 1 to 3 substituents selected from
  - (a) a $C_{1-6}$ alkoxy group (e.g., methoxy), and
  - (b) a halogen atom (e.g., a fluorine atom), or
- (iii) a heterocyclic group (e.g., pyrazolyl, morpholinyl) optionally substituted by 1 to 3 $C_{1-6}$ alkyl groups (e.g., methyl);

n is 0 or 1;

Ring A is a 5- or 6-membered nitrogen-containing heterocycle (preferably a 5- or 6-membered nitrogen-containing non-aromatic heterocycle (e.g., pyrrolidine, piperidine, piperazine)) optionally further substituted by 1 to 3 substituents selected from
(1) a halogen atom (e.g., a fluorine atom), and
(2) an oxo group; and Ring B is a 6-membered aromatic ring (e.g., benzene, pyridine, pyrazine) optionally further substituted by 1 to 3 substituents selected from
(1) a halogen atom (e.g., a fluorine atom), and
(2) a $C_{1-6}$ alkyl group (e.g., methyl), provided that (4-ethylpiperazin-1-yl) (2-(pyrimidin-4-yl)phenyl)methanone, and (4-methylpiperazin-1-yl) (2-(pyrimidin-4-yl)phenyl)methanone are excluded.

[Compound C-2]

Compound (I) wherein

X is a carbon atom or a nitrogen atom;

Y is —O—, —CH$_2$—, —CO— or —SO$_2$—;

Z is CH or N;

$R^1$ is (1) a $C_{1-6}$ alkyl group (e.g., methyl) optionally substituted by 1 to 3 substituents selected from
- (i) a phenyl group optionally substituted by 1 to 3 substituents selected from
  - (a) a $C_{1-6}$ alkoxy group (e.g., methoxy), and
  - (b) a halogen atom (e.g., a fluorine atom),
- (ii) a pyridyl group, an imidazolyl group, a pyrazolyl group and a thiazolyl group, each optionally substituted by 1 to 3 $C_{1-6}$ alkyl groups (e.g., methyl),
- (iii) a mono- or di-$C_{1-6}$ alkyl-carbamoyl group (e.g., dimethylcarbamoyl, diethylcarbamoyl), and
- (iv) morpholinylcarbonyl, (2) —CO—$R^2$ wherein $R^2$ is
- (i) a $C_{1-6}$ alkyl group (e.g., methyl) optionally substituted by 1 to 3 substituents selected from a phenyl group optionally substituted by 1 to 3 $C_{1-6}$ alkoxy groups (e.g., methoxy), or
- (ii) a cyclopropyl group, or (3) —SO$_2$—$R^3$ wherein $R^3$ is
- (i) a $C_{1-6}$ alkyl group (e.g., ethyl),
- (ii) a phenyl group optionally substituted by 1 to 3 substituents selected from
  - (a) a $C_{1-6}$ alkoxy group (e.g., methoxy), and
  - (b) a halogen atom (e.g., a fluorine atom), or
- (iii) a pyrazolyl group or morpholinyl group, each optionally substituted by 1 to 3 $C_{1-6}$ alkyl groups (e.g., methyl);

n is 0 or 1;

Ring A is a pyrrolidine ring, a piperidine ring or a piperazine ring, each optionally further substituted by 1 to 3 substituents selected from
(1) a halogen atom (e.g., a fluorine atom), and
(2) an oxo group; and Ring B is a benzene ring, a pyridine ring or a pyrazine ring, each optionally further substituted by 1 to 3 substituents selected from
(1) a halogen atom (e.g., a fluorine atom), and
(2) a $C_{1-6}$ alkyl group (e.g., methyl), provided that (4-ethylpiperazin-1-yl) (2-(pyrimidin-4-yl)phenyl)methanone, and (4-methylpiperazin-1-yl) (2-(pyrimidin-4-yl)phenyl)methanone are excluded.

[Compound C-3]

Compound (I) wherein

X is a carbon atom or a nitrogen atom;

Y is —O—, —CH$_2$—, —CO— or —SO$_2$—;

Z is CH or N;

$R^1$ is (1) a $C_{1-6}$ alkyl group (e.g., methyl) substituted by 1 to 3 substituents selected from
- (i) a phenyl group optionally substituted by 1 to 3 substituents selected from
  - (a) a $C_{1-6}$ alkoxy group (e.g., methoxy), and
  - (b) a halogen atom (e.g., a fluorine atom),
- (ii) a pyridyl group, an imidazolyl group, a pyrazolyl group and a thiazolyl group, each optionally substituted by 1 to 3 $C_{1-6}$ alkyl groups (e.g., methyl),
- (iii) a mono- or di-$C_{1-6}$ alkyl-carbamoyl group (e.g., dimethylcarbamoyl, diethylcarbamoyl), and
- (iv) morpholinylcarbonyl, (2) —CO—$R^2$ wherein $R^2$ is
- (i) a $C_{1-6}$ alkyl group (e.g., methyl) optionally substituted by 1 to 3 substituents selected from a phenyl group optionally substituted by 1 to 3 $C_{1-6}$ alkoxy groups (e.g., methoxy), or
- (ii) a cyclopropyl group, or (3) —SO$_2$—$R^3$ wherein $R^3$ is
- (i) a $C_{1-6}$ alkyl group (e.g., ethyl),
- (ii) a phenyl group optionally substituted by 1 to 3 substituents selected from (a) a $C_{1-6}$ alkoxy group (e.g., methoxy), and
(b) a halogen atom (e.g., a fluorine atom), or
(iii) a pyrazolyl group or morpholinyl group, each optionally substituted by 1 to 3 $C_{1-6}$ alkyl groups (e.g., methyl);
n is 0 or 1;
Ring A is a pyrrolidine ring, a piperidine ring or a piperazine ring, each optionally further substituted by 1 to 3 substituents selected from
(1) a halogen atom (e.g., a fluorine atom), and
(2) an oxo group; and
Ring B is a benzene ring, a pyridine ring or a pyrazine ring, each optionally further substituted by 1 to 3 substituents selected from
(1) a halogen atom (e.g., a fluorine atom), and
(2) a $C_{1-6}$ alkyl group (e.g., methyl).

[Compound D-1]
Compound (I) wherein
X is a carbon atom;
Y is —O—;
Z is CH;
$R_1$ is
(1) a $C_{1-6}$ alkyl group (e.g., methyl) optionally substituted by 1 to 3 substituents selected from
(i) a heterocyclic group (e.g., pyrazolyl, thiazolyl) optionally substituted by 1 to 3 $C_{1-6}$ alkyl groups (e.g., methyl), and
(ii) a mono- or di-$C_{1-6}$ alkyl-carbamoyl group (e.g., dimethylcarbamoyl), or
(2) —SO$_2$—R$^3$ wherein R$^3$ is a heterocyclic group (e.g., pyrazolyl) optionally substituted by 1 to 3 $C_{1-6}$ alkyl groups (e.g., methyl);
n is 0 or 1;
Ring A is a 5- or 6-membered nitrogen-containing heterocycle (preferably a 5- or 6-membered nitrogen-containing non-aromatic heterocycle (e.g., pyrrolidine, piperidine)) optionally further substituted by 1 to 3 halogen atoms (e.g., a fluorine atom); and
Ring B is a 6-membered aromatic heterocycle (e.g., pyridine, pyrazine).

[Compound D-2]
Compound (I) wherein
X is a carbon atom;
Y is —O—;
Z is CH;
$R^1$ is
(1) a $C_{1-6}$ alkyl group (e.g., methyl) optionally substituted by 1 to 3 substituents selected from
(i) a pyrazolyl group and a thiazolyl group, each optionally substituted by 1 to 3 $C_{1-6}$ alkyl groups (e.g., methyl), and
(ii) a mono- or di-$C_{1-6}$ alkyl-carbamoyl group (e.g., dimethylcarbamoyl), or
(2) —SO$_2$—R$^3$ wherein R$^3$ is a pyrazolyl group optionally substituted by 1 to 3 $C_{1-6}$ alkyl groups (e.g., methyl);
n is 0 or 1;
Ring A is a pyrrolidine ring or a piperidine ring, each optionally further substituted by 1 to 3 halogen atoms (e.g., a fluorine atom); and
Ring B is a pyridine ring or a pyrazine ring.

[Compound E-1]
Compound (I) wherein
X is a carbon atom;
Y is —O—;
Z is CH;
$R^1$ is
(1) a $C_{1-6}$ alkyl group (e.g., methyl) optionally substituted by 1 to 3 substituents selected from
(i) a $C_{6-14}$ aryl group (e.g., phenyl),
(ii) a heterocyclic group (preferably an aromatic heterocyclic group (e.g., pyrazolyl, thiazolyl)) optionally substituted by 1 to 3 $C_{1-6}$ alkyl groups (e.g., methyl), and
(iii) a mono- or di-$C_{1-6}$ alkyl-carbamoyl group (e.g., dimethylcarbamoyl), or
(2) —SO$_2$—R$^3$ wherein R$^3$ is a $C_{6-14}$ aryl group (e.g., phenyl) optionally substituted by 1 to 3 $C_{1-6}$ alkoxy groups (e.g., methoxy);
n is 0 or 1;
Ring A is a 5- or 6-membered nitrogen-containing heterocycle (preferably a 5- or 6-membered nitrogen-containing non-aromatic heterocycle (e.g., pyrrolidine, piperidine)) optionally further substituted by 1 to 3 halogen atoms (e.g., a fluorine atom); and
Ring B is a 6-membered aromatic ring (e.g., benzene, pyridine, pyrazine).

[Compound E-2]
Compound (I) wherein
X is a carbon atom;
Y is —O—;
Z is CH;
$R^1$ is
(1) a $C_{1-6}$ alkyl group (e.g., methyl) optionally substituted by 1 to 3 substituents selected from
(i) a phenyl group,
(ii) a pyrazolyl group and a thiazolyl group, each optionally substituted by 1 to 3 $C_{1-6}$ alkyl groups (e.g., methyl), and
(iii) a mono- or di-$C_{1-6}$ alkyl-carbamoyl group (e.g., dimethylcarbamoyl), or
(2) —SO$_2$—R$^3$ wherein R$^3$ is a phenyl group optionally substituted by 1 to 3 $C_{1-6}$ alkoxy groups (e.g., methoxy);
n is 0 or 1;
Ring A is a pyrrolidine ring or a piperidine ring, each optionally further substituted by 1 to 3 halogen atoms (e.g., a fluorine atom); and
Ring B is a benzene ring, a pyridine ring or a pyrazine ring.

[Compound F-1]
Compound (I) wherein
X is a carbon atom;
Y is —O—;
Z is CH;
$R^1$ is
(1) a $C_{1-6}$ alkyl group (e.g., methyl) optionally substituted by 1 to 3 substituents selected from
(i) a heterocyclic group (preferably an aromatic heterocyclic group (e.g., pyrazolyl, thiazolyl, preferably pyrazolyl)) optionally substituted by 1 to 3 $C_{1-6}$ alkyl groups (e.g., methyl), and
(ii) a mono- or di-$C_{1-6}$ alkyl-carbamoyl group (e.g., dimethylcarbamoyl), or
(2) —SO$_2$—R$^3$ wherein R$^3$ is a $C_{6-14}$ aryl group (e.g., phenyl) optionally substituted by 1 to 3 $C_{1-6}$ alkoxy groups (e.g., methoxy);
n is 0 or 1;
Ring A is a 5- or 6-membered nitrogen-containing heterocycle (preferably a 5- or 6-membered nitrogen-containing non-aromatic heterocycle (e.g., pyrrolidine, piperidine)) optionally further substituted by 1 to 3 halogen atoms (e.g., a fluorine atom); and
Ring B is a 6-membered aromatic heterocycle (e.g., pyridine, pyrazine).

[Compound F-2]
Compound (I) wherein
X is a carbon atom;
Y is —O—;
Z is CH;
$R^1$ is
(1) a $C_{1-6}$ alkyl group (e.g., methyl) optionally substituted by 1 to 3 substituents selected from
  (i) a pyrazolyl group and a thiazolyl group, each optionally substituted by 1 to 3 $C_{1-6}$ alkyl groups (e.g., methyl), and
  (ii) a mono- or di-$C_{1-6}$ alkyl-carbamoyl group (e.g., dimethylcarbamoyl), or
(2) —$SO_2$—$R^3$ wherein $R^3$ is a phenyl group optionally substituted by 1 to 3 $C_{1-6}$ alkoxy groups (e.g., methoxy);
n is 0 or 1;
Ring A is a pyrrolidine ring or a piperidine ring, each optionally further substituted by 1 to 3 halogen atoms (e.g., a fluorine atom); and
Ring B is a pyridine ring or a pyrazine ring.

[Compound G-1]
Compound (I) wherein
X is a carbon atom;
Y is —O—;
Z is CH;
$R^1$ is
(1) a $C_{1-6}$ alkyl group (e.g., methyl) optionally substituted by 1 to 3 substituents selected from
  (i) a pyrazolyl group optionally substituted by 1 to 3 $C_{1-6}$ alkyl groups (e.g., methyl), and
  (ii) a mono- or di-$C_{1-6}$ alkyl-carbamoyl group (e.g., dimethylcarbamoyl), or
(2) —$SO_2$—$R^3$ wherein $R^3$ is a phenyl group optionally substituted by 1 to 3 $C_{1-6}$ alkoxy groups (e.g., methoxy);
n is 0 or 1;
Ring A is a pyrrolidine ring or a piperidine ring, each optionally further substituted by 1 to 3 halogen atoms (e.g., a fluorine atom); and
Ring B is a pyridine ring or a pyrazine ring.

[Compound H-1]
3-((1-((1-methyl-1H-pyrazol-4-yl)methyl)piperidin-4-yl)oxy)-2,4'-bipyridine or a salt thereof,
2-(3,3-difluoro-4-((3-(pyridin-4-yl)pyrazin-2-yl)oxy)piperidin-1-yl)-N,N-dimethylacetamide or a salt thereof, or
3-((1-((4-methoxyphenyl)sulfonyl)pyrrolidin-3-yl)oxy)-2,4'-bipyridine or a salt thereof.

[Compound H-2]
3-((1-((1-methyl-1H-pyrazol-4-yl)methyl)piperidin-4-yl)oxy)-2,4'-bipyridine or a salt thereof.

[Compound H-3]
2-(3,3-difluoro-4-((3-(pyridin-4-yl)pyrazin-2-yl)oxy)piperidin-1-yl)-N,N-dimethylacetamide or a salt thereof.

[Compound H-4]
3-((1-((4-methoxyphenyl)sulfonyl)pyrrolidin-3-yl)oxy)-2,4'-bipyridine or a salt thereof.

When compound (I) is in a form of a salt, examples thereof include metal salts, an ammonium salt, salts with organic base, salts with inorganic acid, salts with organic acid, salts with basic or acidic amino acid, and the like. Preferable examples of the metal salt include alkali metal salts such as sodium salt, potassium salt and the like; alkaline earth metal salts such as calcium salt, magnesium salt, barium salt and the like; an aluminum salt, and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like. Preferable examples of the salt with acidic amino acid include salts with aspartic acid, glutamic acid and the like.

Among them, a pharmaceutically acceptable salt is preferable. For example, when a compound has an acidic functional group, examples thereof include inorganic salts such as alkali metal salts (e.g., sodium salt, potassium salt etc.), alkaline earth metal salts (e.g., calcium salt, magnesium salt etc.) and the like, ammonium salt etc., and when a compound has a basic functional group, examples thereof include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

[Production Method]

The compound of the present invention and the raw material compounds can be produced by a method known per se, for example, by method shown in the following scheme and the like. In the following, the "room temperature" generally means 0-40° C. and, unless otherwise specified, each symbol in the chemical formulas described in the schemes is as defined above. In the schemes, each compound includes salts, and examples of such salt include those similar to the salts of the compound of the present invention, and the like. The compound obtained in each step can be used directly as the reaction mixture or as a crude product for the next reaction. It can also be isolated from a reaction mixture by a conventional method, and can be easily purified by a separation means such as recrystallization, distillation, chromatography and the like. When the compound in the scheme is commercially available, a commercially available product can also be used directly. When each ring in the formula (I) has a substituent, the corresponding precursor also has a similar substituent.

When the raw material compound has an amino group, a carboxyl group, a hydroxy group or a heterocyclic group, these groups may be protected by a protecting group generally used in peptide chemistry and the like. By removing the protecting group as necessary after the reaction, the objective compound can be obtained. The protection and deprotection can be performed according to a method known per se, for example, the method described in "Protective Groups in Organic Synthesis, 3rd Ed", John Wiley and Sons, Inc. (1999) (Theodora W. Greene, Peter G. M. Wuts). Preferable examples of the protecting group include a tert-butylcarbamate group, a benzylcarbamate group, a benzyl group, a 4-methoxybenzyl group, a methyl group, an ethyl group, a tert-butyl group, a trimethylsilyl group, a triethylsilyl group, a tert-butyldimethylsilyl group, a tert-butyldiphenylsilyl group, a triisopropylsilyl group and the like. Examples of the substituent represented by PG' include a hydrogen atom, a tert-butylcarbamate group, a benzylcarbamate group, benzyl group, a 4-methoxybenzyl group and the like.

The following each step can be performed without solvent, or by dissolving or suspending raw material compound in a suitable solvent prior to the reaction. In this case, solvent may be used alone, or two or more kinds of these solvents may be mixed in an appropriate ratio and used. Specific examples of the solvent used for the production method of the compound of the present invention include the followings.

alcohols: methanol, ethanol, 1-propanol, 2-propanol, tert-butyl alcohol, tert-amyl alcohol, 2-methoxyethanol etc.
ethers: diethyl ether, diisopropyl ether, diphenyl ether, tetrahydrofuran, 1,4-dioxane, 1,2-dimethoxyethane etc. aromatic hydrocarbons: benzene, chlorobenzene, toluene, xylene etc.
saturated hydrocarbons: cyclohexane, hexane etc.
amides: N,N-dimethylformamide, N,N-dimethylacetamide, hexamethylphosphoric triamide, N-methylpyrrolidone etc.
halogenated hydrocarbons: dichloromethane, chloroform, carbon tetrachloride, 1,2-dichloroethane etc.
nitriles: acetonitrile, propionitrile etc.
sulfoxides: dimethylsulfoxide etc.
organic bases: triethylamine, pyridine, 2,6-lutidine etc.
acid anhydrides: acetic anhydride etc.
organic acids: formic acid, acetic acid, propionic acid, trifluoroacetic acid, methanesulfonic acid etc.
inorganic acids: hydrochloric acid, sulfuric acid etc.
esters: methyl acetate, ethyl acetate, butyl acetate etc.
ketones: acetone, methyl ethyl ketone etc. water Specific examples of the base or acid scavenger used for the production method of the compound of the present invention include the followings.

inorganic bases: sodium hydroxide, potassium hydroxide, magnesium hydroxide etc.
basic salts: sodium carbonate, potassium carbonate, cesium carbonate, calcium carbonate, sodium hydrogen carbonate etc.
organic bases: triethylamine, diisopropylethylamine, tributylamine, cyclohexyldimethylamine, pyridine, 2,6-lutidine, 4-dimethylaminopyridine, N,N-dimethylaniline, N-methylpiperidine, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene, imidazole etc.
metal alkoxides: sodium methoxide, sodium ethoxide, potassium tert-butoxide etc.
alkali metal hydrides: sodium hydride, potassium hydride etc. metal amides: sodium amide, lithiumdiisopropylamide, lithiumhexamethyldisilazide etc.

organic lithium reagents: methyllithium, n-butyllithium, sec-butyllithium, tert-butyllithium etc.

Specific examples of the acid or acid catalyst used for the production method of the compound of the present invention include the followings.

inorganic acids: hydrochloric acid, sulfuric acid, nitric acid, hydrobromic acid, phosphoric acid etc.
organic acids: acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid etc.
Lewis acid: boron trifluoride ether complex, zinc iodide, anhydrous aluminum chloride, anhydrous zinc chloride, anhydrous iron chloride etc.

Compound (I) of the present invention can be produced according to the production method explained below.

Unless otherwise specified, each symbol in the general formulas in the schemes is as defined above. In the formulas, $LG^1$-$LG^3$ are each a leaving group, $PG^1$ is an amino-protecting group, $R^a$ is a hydrogen atom or an optionally substituted $C_{1-6}$ alkyl group, in the latter, two $R^a$ in combination optionally form a ring such as 4,4,5,5-tetramethyl-1,3,2-dioxaborolane and the like, $R^5$ is a hydrogen atom or a substituent selected from the above-mentioned Substituent Group A, $R^6$ is a hydrogen atom or an optionally substituted $C_{1-5}$ alkyl group.

The "$C_{1-6}$ alkyl group" of the "optionally substituted $C_{1-6}$ alkyl group" represented by $R^a$ optionally has 1 to 5 (preferably 1 to 3) substituents at substitutable position(s). Examples of the substituent include substituents selected from the above-mentioned Substituent Group A. When the number of the substituents is plural, the respective substituents may be the same or different.

The "$C_{1-5}$ alkyl group" of the "optionally substituted $C_{1-5}$ alkyl group" represented by $R^6$ optionally has 1 to 5 (preferably 1 to 3) substituents at substitutable position(s). Examples of the substituent include substituents selected from the above-mentioned Substituent Group A. When the number of the substituents is plural, the respective substituents may be the same or different.

Examples of the "leaving group" represented by $LG^1$-$LG^3$ include a halogen atom (e.g., a fluorine atom, a chlorine atom, a bromine atom, an iodine atom, etc.), $C_{1-6}$ alkylsulfonyloxy (e.g., methanesulfonyloxy, ethanesulfonyloxy, trifluoromethanesulfonyloxy, etc.), $C_{1-6}$ alkylsulfonyl (e.g., methanesulfonyl, ethanesulfonyl, etc.) and the like. In addition, $LG^1$-$LG^3$ contain substituents convertible to a leaving group, and they are converted to a leaving group in desire step according to a method known per se. For example, when $LG^1$-$LG^3$ are each a methylthio group, it is converted to a methanesulfonyl group by oxidation reaction.

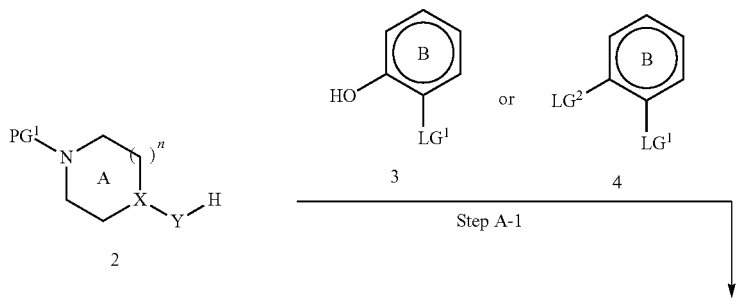

-continued

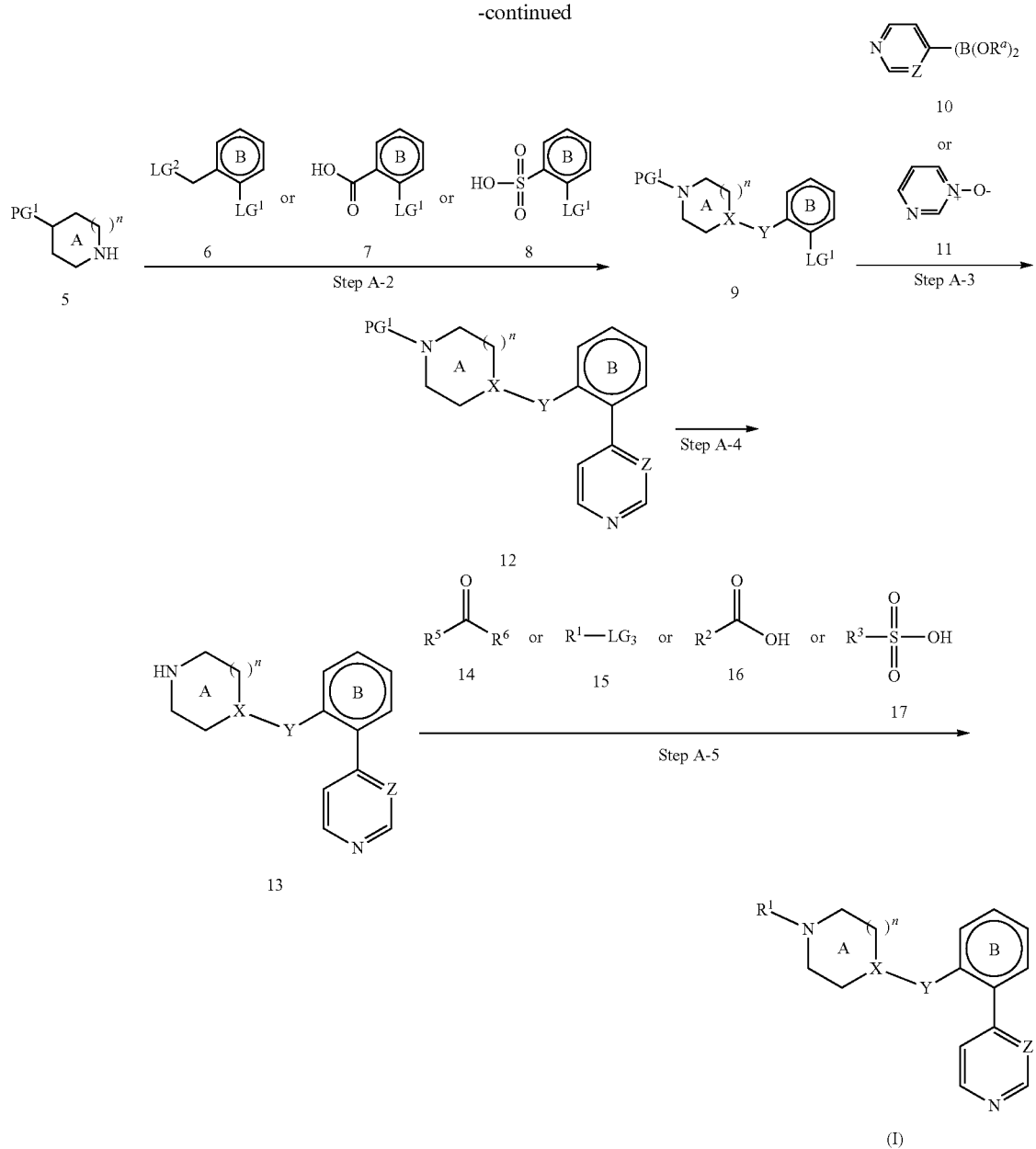

Compound (9) can be produced according to Step A-1 or Step A-2, or a method analogous thereto.

(Step A-1)

Compound (9) wherein Y is —O— can be produced by condensing compound (2) wherein Y is —O— with compound (3). Compound (9) wherein Y is —O—, —S— or —NH— can be produced by condensing compound (2) wherein Y is —O—, —S— or —NH— with compound (4). Compound (9) wherein Y is —SO— or —SO$_2$— can be produced by condensing compound (2) wherein Y is —S— with compound (4), and oxidizing the resulting compound.

When compound (2) wherein Y is —O— is condensed with compound (3), the reaction is carried out in the presence of a mixture of a phosphine reagent and an azo compound, or in the presence of a phosphorane reagent and the like. Examples of the phosphine reagent include triphenylphosphine, tributylphosphine and the like. Examples of the azo compound include diethyl azodicarboxylate, diisopropyl azodicarboxylate, 1,1'-(azodicarbonyl)piperidine and the like. Examples of the phosphorane reagent include cyanomethylenetributylphosphorane and the like. Each of the phosphine reagent and the azo compound, or the phosphorane reagent are(is) used in an amount of about 1 to 50 mol, preferably about 1 to 10 mol, per 1 mol of compound (2) wherein Y is —O—. This reaction is advantageously carried out in a solvent inert to the reaction. The solvent is not particularly limited as long as the reaction proceeds. Preferable examples thereof include ethers, aromatic hydrocarbons, saturated hydrocarbons, amides, halogenated hydrocarbons, nitriles, sulfoxides, mixed solvent thereof and the like. While the reaction time varies depending on the kind of the reagent and solvent to be used, it is generally 10 min-100 hr, preferably 10 min-24 hr. The reaction temperature is generally 0 to 100° C., preferably 0 to 60° C.

When compound (2) wherein Y is —O—, —S— or —NH— is condensed with compound (4), the reaction is carried out in the presence of a base or a metal catalyst, if necessary. Examples of the base include basic salts, organic bases, alkali metal hydrides, organic lithium reagents and the like. The base is used in an amount of about 1 to 20 mol per 1 mol of compound (4). Preferable examples of the metal catalyst include palladium compounds [e.g., palladium(II) acetate, tetrakis(triphenylphosphine)palladium(0), dichlorobis(triphenylphosphine)palladium(II), tris(dibenzylideneacetone)dipalladium(0), [1,1-bis(diphenylphosphino)ferrocene]dichloropalladium(II) and the like] and copper compounds [e.g., copper(I) iodide, copper(I) bromide and the like]. The metal catalyst is used in an amount of about 0.000001 to 10 mol per 1 mol of compound (4). The metal catalyst may be used together with a phosphine ligand [e.g., triphenylphosphine, 4,5-bis(diphenylphosphino)-9,9-dimethylxanthene, tri-tert-butylphosphine and the like] or an amine ligand [e.g., 2-methylquinolin-8-ol, 1,10-phenanthroline, 1,2-diaminocyclohexane, N,N'-dimethyl-1,2-ethanediamine and the like]. When the phosphine ligand or amine ligand is used, the phosphine ligand or amine ligand is used in an amount of about 0.01 to 5 mol per 1 mol of compound (4). Compound (2) wherein Y is —O—, —S— or —NH— is used in an amount of about 0.8 to 10 mol per 1 mol of compound (4). When the metal catalyst unstable to oxygen is used in this reaction, the reaction is preferably carried out under an inert gas such as argon gas, nitrogen gas and the like.

This reaction is advantageously carried out in a solvent inert to the reaction. The solvent is not particularly limited as long as the reaction proceeds. Preferable examples thereof include, alcohols, ethers, aromatic hydrocarbons, saturated hydrocarbons, amides, halogenated hydrocarbons, nitriles, esters, sulfoxides, water, mixed solvent thereof and the like. While the reaction time varies depending on the kind of the reagent and solvent to be used, it is generally 1 min-200 hr. The reaction temperature is preferably 0 to 200° C. In addition, microwave may be irradiated to promote the reaction.

Compound (2), (3) and (4) may be a commercially available product, or can also be produced according to a method known per se or a method analogous thereto.

(Step A-2)

Compound (9) wherein Y is —CH$_2$— can be produced by condensing compound (5) with compound (6). Compound (9) wherein Y is —CO— can be produced by condensing compound (5) with compound (7). Compound (9) wherein Y is —SO$_2$— can also be produced by condensing compound (5) with compound (8).

When compound (5) is condensed with compound (6), the reaction is carried out in the presence of a base. Examples of the base include potassium carbonate, sodium carbonate, sodium hydride, potassium hydride and the like. The base is used in an amount of about 1 to 20 mol per 1 mol of compound (6). Compound (5) is used in an amount of about 1 to 20 mol per 1 mol of compound (6). This reaction is advantageously carried out in a solvent inert to the reaction. The solvent is not particularly limited as long as the reaction proceeds. Preferable examples thereof include, alcohols, ethers, aromatic hydrocarbons, saturated hydrocarbons, amides, halogenated hydrocarbons, nitriles, esters, sulfoxides, water, mixed solvent thereof and the like. While the reaction time varies depending on the kind of the reagent and solvent to be used, it is generally 1 min-100 hr. The reaction temperature is preferably 0 to 100° C. In addition, microwave may be irradiated to promote the reaction.

When compound (5) is condensed with compound (7), a reactive derivative of compound (7) can be used. Examples of the reactive derivative include acid halides such as acid chlorides, acid bromides and the like; acid amides with pyrazole, imidazole, benzotriazole and the like; mixed anhydrides with acetic acid, propionic acid, butyric acid and the like; acid azides; activated esters such as diethoxyphosphoric acid ester, diphenoxyphosphoric acid ester, p-nitrophenyl ester, 2,4-dinitrophenyl ester, an ester with 1-hydroxybenzotriazole, and the like; activated thio esters such as 2-pyridylthio ester, 2-benzothiazolylthio ester and the like, and the like. Alternatively, instead of use of the reactive derivative, compound (5) may be directly reacted with carboxylic acid (7) in the presence of a suitable condensing agent. Examples of the condensing agent include N,N'-disubstituted carbodiimides such as N,N'-dicyclohexylcarbodiimide, 1-ethyl-3-(3-dimethylaminopropyl)carbodiimide (WSC) hydrochloride and the like; azolides such as N,N'-carbonyldiimidazole and the like; dehydrating agents such as N-ethoxycarbonyl-2-ethoxy-1,2-dihydroquinoline, phosphorus oxychloride, alkoxyacetylenes and the like; 2-halogeno pyridinium salts such as 2-chloromethylpyridinium iodide, 2-fluoro-1-methylpyridinium iodide and the like; phosphorylcyanides such as diethylphosphorylcyanide and the like; 2-(7-azabenzotriazol-1-yl)-1,1,3,3-tetramethyluronium hexafluorophosphate (HATU), 0-(7-azabenzotriazol-1-yl)-N,N,N',N'-tetramethyluronium tetrafluoroborate (TATU) and the like. The reaction is considered to proceed via a reactive derivative of carboxylic acid (7) by using a condensing agent. Carboxylic acid (7) or a reactive derivative thereof is generally used in an amount of about 0.8 to 5 mol per 1 mol of compound (5). This reaction is advantageously carried out in a solvent inert to the reaction. The solvent is not particularly limited as long as the reaction proceeds. Preferable examples thereof include, ethers, aromatic hydrocarbons, saturated hydrocarbons, amides, halogenated hydrocarbons, nitriles, sulfoxides, aromatic organic bases, mixed solvent thereof and the like. In addition, when an acidic substance is generated due to the reaction, the reaction can be carried out in the presence of an acid scavenger to remove the acidic substance from the reaction system. Examples of the acid scavenger include basic salts, organic bases and the like. In addition, basic salts, organic bases and the like can also be used to promote the reaction. While the reaction time varies depending on the kind of the reagent and solvent to be used, it is generally 1 min-72 hr. The reaction temperature is preferably 0 to 100° C.

When compound (5) is condensed with compound (8), compound (9) can be produced by condensing compound (5) with compound (8) or a reactive derivative thereof. The reaction is carried out in the same manner as in the condensation of compound (5) with compound (7). Compound (5), (6), (7) and (8) may be a commercially available product, or can also be produced according to a method known per se or a method analogous thereto.

(Step A-3)

Compound (12) can be produced by condensing compound (9) with compound (10), or compound (12) wherein Z is N can also be produced by condensing compound (9) with compound (11). The condensation reaction is carried out by reacting compound (9) with compound (10), or compound (9) with compound (11), in the presence of a metal catalyst. Preferable examples of the metal catalyst include palladium compounds [e.g., palladium(II) acetate, tetrakis(triphenylphosphine)palladium(0), dichlorobis(triphenylphosphine)palladium(II), tris(dibenzylideneacetone)dipalladium(0), a complex of palladium(II) acetate and 1,1'- bis(diphenylphosphino)ferrocene, and the like]. The metal catalyst is used in an amount of about 0.000001 to 1.0 mol per 1 mol of compound (9). The metal catalyst can be used together with a phosphine ligand. When the phosphine ligand is used, it is used in an amount of about 0.01 to 5 mol per 1 mol of compound (9). Examples of the phosphine ligand include triphenylphosphine, 4,5-bis(diphenylphosphino)-9,9-dimethylxanthene, tri-tert-butylphosphine and the like. The reaction is generally carried out in the presence of a base. Examples of the base include for example inorganic bases, basic salts and the like. In addition, the reaction can also be carried out by addition of an additive such as copper(I) cyanide, copper(I) bromide and the like, if desired. Compound (10) or compound (11) is used in an amount of about 0.8 to 10 mol per 1 mol of compound (9). The base is used in an amount of about 1 to 20 mol per 1 mol of compound (9). The additive is used in an amount of about 0.000001 to 5.0 mol per 1 mol of compound (9). When the metal catalyst unstable to oxygen is used in this reaction, the reaction is preferably carried out under an inert gas such as argon gas, nitrogen gas and the like. This reaction is advantageously carried out in a solvent inert to the reaction. The solvent is not particularly limited as long as the reaction proceeds. Preferable examples thereof include alcohols, ethers, aromatic hydrocarbons, saturated hydrocarbons, amides, halogenated hydrocarbons, nitriles, esters, water, mixed solvent thereof and the like. While the reaction time varies depending on the kind of the reagent and solvent to be used, it is generally 1 min-200 hr. The reaction temperature is preferably 0 to 150° C. In addition, microwave may be irradiated to promote the reaction. Compound (9), (10) and (11) may be a commercially available product, or can also be produced according to a method known per se or a method analogous thereto.

(Step A-4)

Compound (13) can be produced by removing the protecting group $PG^1$ of compound (12). The removal of the protecting group can be carried out according to a method known per se, for example, the method described in "Protective Groups in Organic Synthesis, 3rd Ed.", Wiley-Interscience (1999) (Theodora W. Greene, Peter G. M. Wuts) and the like. Compound (12) can also be produced according to a method known per se or a method analogous thereto.

(Step A-5)

Compound (I) of the present invention wherein $R^1$ is an optionally substituted $C_{1-6}$ alkyl group can be produced by subjecting compound (13) to a reductive amination reaction with compound (14), or can also be produced by condensing compound (13) with compound (15). Compound (I) of the present invention wherein $R^1$ is —CO—$R^2$ can be produced by condensing compound (13) with compound (16). Compound (I) of the present invention wherein $R^1$ is —SO$_2$—$R^3$ can be produced by condensing compound (13) with compound (17).

When compound (13) is condensed with compound (14), the reaction is carried out in the presence of a reducing agent. Compound (14) is used in an amount of about 1 mol to large excess, preferably about 1 to 10 mol, per 1 mol of compound (13). Examples of the reducing agent include metal hydrogen complex compounds such as sodium triacetoxyborohydride, sodium borohydride, sodium cyanoborohydride, lithium aluminium hydride and the like, diborane and the like, and it is used in an amount of about 0.3 mol to large excess, preferably about 1 to 10 mol, per 1 mol of compound (13). Alternatively, instead of use of the reducing agent, the reaction can also be carried out by employing a catalytic reduction in the presence of a catalyst such as palladium, Raney nickel and the like, an electrolytic reduction using lead or platinum as a cathode, and the like. An acid (e.g., mineral acid such as hydrochloric acid, phosphoric acid, sulfuric acid and the like, organic acid such as toluenesulfonic acid, methanesulfonic acid, acetic acid and the like) may be added to the reaction system in an amount of about 0.1 to 2 mol per 1 mol of compound (13). The solvent is not particularly limited as long as the reaction proceeds. Preferable examples thereof include, alcohols, carboxylic acids, ethers, aromatic hydrocarbons, saturated hydrocarbons, amides, halogenated hydrocarbons, nitriles, esters, sulfoxides, water, mixed solvent thereof and the like. The reaction time is generally about 0.5-about 72 hr, preferably about 1-about 24 hr. The reaction temperature is generally about −30° C.-about 200° C., preferably about 0° C.-about 100° C.

When compound (13) is condensed with compound (15), the reaction is carried out in the same manner as in the reaction of compound (5) with compound (6).

When compound (13) is condensed with compound (16), the reaction is carried out in the same manner as in the reaction of compound (5) with compound (7).

When compound (13) is condensed with compound (17), the reaction is carried out in the same manner as in the reaction of compound (5) with compound (8).

Compound (13) can be produced according to the method described in the above-mentioned (Step A-4) or a method known per se or a method analogous thereto, or may be a commercially available product.

Compound (14), (15), (16) and (17) may be a commercially available product, or can also be produced according to a method known per se or a method analogous thereto.

The raw material compound and/or the production intermediate for compound (I) may form a salt. While the salt is not particularly limited as long as the reaction can be performed, examples thereof include those similar to the salts optionally formed by compound (I) and the like, and the like.

As for the configuration isomers (E, Z forms) of compound (I), they can be isolated and purified when isomerization occurs, for example, according to a conventional separation means such as extraction, recrystallization, distillation, chromatography and the like to obtain a pure compound. In addition, the corresponding pure isomer can be obtained by isomerizing a double bond using heating, an acid catalyst, a transition metal complex, a metal catalyst, a radical catalyst, light irradiation or a strong base catalyst and the like, according to the method described in Shin-Jikken Kagaku Kouza 14 (The Chemical Society of Japan ed.), pages 251 to 253; 4th Edition Jikken Kagaku Kouza 19 (The Chemical Society of Japan ed.), pages 273 to 274 or a method analogous thereto.

Compound (I) contains a stereoisomer depending to the kind of a substituent, and each stereoisomer and a mixture thereof are encompassed in the present invention.

When desired, compound (I) can be synthesized by performing deprotection reaction, acylation reaction, alkylation reaction, hydrogenation reaction, oxidation reaction, reduction reaction, reaction of carbon chain extension, substituent exchange reaction singly or two or more thereof in combination.

When the objective product is obtained as a free form by the above-mentioned reaction, it can be converted to a salt according to a conventional method, or when the objective product is obtained as a salt, it can be converted to a free form or other salt according to a conventional method. The thus-obtained compound (I) can also be isolated and purified from a reaction mixture according to a known method such as phase transfer, concentration, solvent extraction, distillation, crystallization, recrystallization, chromatography and the like.

When compound (I) contains a configurational isomer, a diastereomer, a conformer and the like, each can be isolated according to the above-mentioned separation and purification methods, if desired. In addition, when compound (I) is recemic, d-form and l-form can be isolated according to a conventional optical resolution.

Compound (I) may be a prodrug, and the prodrug of compound (I) refers to a compound which is converted to compound (I) as a result of a reaction with an enzyme, gastric acid, etc. under physiological conditions in vivo, thus a compound that undergoes enzymatic oxidation, reduction, hydrolysis etc. to convert to compound (I) and a compound that undergoes hydrolysis and the like by gastric acid, etc. to convert to compound (I).

Examples of the prodrug for compound (I) include
(1) a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl) methoxycarbonylation, tetrahydrofurylation, pyrrolidylmethylation, pivaloyloxymethylation, tert-butylation, ethoxycarbonylation, tert-butoxycarbonylation or acetylation, cyclopropylcarbonylation, and the like);
(2) a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation, and the like);
(3) a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, and the like) and the like. Any of these compounds can be produced from compound (I) according to a method known per se.

A prodrug of compound (I) may also be one which is converted to compound (I) under physiological conditions as described in "IYAKUHIN no KAIHATSU (Development of Pharmaceuticals)", Vol. 7, Design of Molecules, p. 163-198, Published by HIROKAWA SHOTEN (1990).

In the present specification, compound (I) and a prodrug thereof are sometimes collectively abbreviated as "the compound of the present invention".

When compound (I) has isomers such as optical isomer, stereoisomer, positional isomer, rotamer and the like, such isomers and a mixture thereof are also encompassed in compound (I). For example, when compound (I) has optical isomers, an optical isomer resolved from this compound is also encompassed in compound (I). These isomers can be obtained as a single product according to synthesis methods or separation methods known per se (e.g., concentration, solvent extraction, column chromatography, recrystallization, etc.).

Compound (I) may be a crystal, and a single crystal form and a mixture of crystal forms are both encompassed in compound (I). The crystal can be produced by crystallizing according to a crystallization method known per se.

Compound (I) may be a hydrate, a non-hydrate, a solvate or a non-solvate.

Compound (I) may be labeled with an isotope (e.g., $^3$H, $^{11}$C, $^{14}$C, $^{15}$F, $^{35}$S, $^{125}$I etc.) and the like.

Compound (I) also encompasses a deuterium conversion form wherein $^1$H is converted to $^2$H(D).

Compound (I) may be a pharmaceutically acceptable cocrystal or a salt thereof. The cocrystal or a salt thereof means a crystalline substance constituted with two or more special solids at room temperature, each having different physical properties (e.g., structure, melting point, melting heat, hygroscopicity, solubility and stability etc.). The cocrystal or a salt thereof can be produced according to a cocrystallization a method known per se.

Compound (I) may also be used as a PET (Positron Emission Tomography) tracer.

The compound of the present invention has low toxicity, and can be used as it is or in the form of a pharmaceutical composition by mixing with a pharmacologically acceptable carrier etc. to mammals (e.g., human, mouse, rat, rabbit, dog, cat, bovine, horse, swine, monkey) as an agent for the prophylaxis or treatment of various diseases mentioned below.

As pharmacologically acceptable carriers, various organic or inorganic carrier substances conventionally used as preparation materials can be used. These are incorporated as excipient, lubricant, binder and disintegrant for solid preparations, or solvent, solubilizing agent, suspending agent, isotonicity agent, buffer and soothing agent for liquid preparations, and the like, and preparation additives such as preservative, antioxidant, colorant, sweetening agent and the like can be added as necessary.

Preferable examples of the excipient include lactose, sucrose, D-mannitol, D-sorbitol, starch, gelatinated starch, dextrin, crystalline cellulose, low-substituted hydroxypropylcellulose, sodium carboxymethylcellulose, gum arabic, pullulan, light anhydrous silicic acid, synthesis aluminum silicate and magnesium alumino metasilicate.

Preferable examples of the lubricant include magnesium stearate, calcium stearate, talc and colloidal silica.

Preferable examples of the binder include gelatinated starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, croscarmellose sodium, sodium carboxymethyl starch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionate, lecithin, benzalkonium chloride, benzethonium chloride, glycerol monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates; and polyoxyethylene hydrogenated castor oil.

Preferable examples of the isotonicity agent include sodium chloride, glycerol, D-mannitol, D-sorbitol and glucose.

Preferable examples of the buffer include buffers such as phosphate, acetate, carbonate, citrate and the like.

Preferable examples of the soothing agent include benzyl alcohol.

Preferable examples of the preservative include p-oxybenzoates, chlorobutanol, benzyl alcohol, phenethyl alcohol, dehydroacetic acid and sorbic acid.

Preferable examples of the antioxidant include sulfite, ascorbate and the like.

Preferable examples of the colorant include aqueous water-soluble food tar colors (e.g., food colors such as Food Color Red Nos. 2 and 3, Food Color Yellow Nos. 4 and 5, Food Color Blue Nos. 1 and 2 and the like), water insoluble lake dyes (e.g., aluminum salt of the above-mentioned water-soluble food tar color) and natural dyes (e.g., β-carotene, chlorophyll, ferric oxide red).

Preferable examples of the sweetening agent include saccharin sodium, dipotassium glycyrrhizinate, aspartame and stevia.

Examples of the dosage form of the pharmaceutical composition include oral preparations such as tablet (including sugar-coated tablet, film-coated tablet, sublingual tablet, orally disintegrating tablet), capsules (including soft capsule, microcapsule), granule, powder, troche, syrup, emulsion, suspension, films (e.g., orally disintegrable films) and the like; and parenteral agents such as injection (e.g., subcutaneous injection, intravenous injection, intramuscular injection, intraperitoneal injection, drip infusion), external preparations (e.g., dermal preparation, ointment), suppository (e.g., rectal suppository, vaginal suppository), pellet, nasal preparation, pulmonary preparation (inhalant), eye drop and the like.

These can be respectively safely administered orally or parenterally (e.g., topically, rectally, intravenously administered).

These preparations may be a release control preparation (e.g., sustained-release microcapsule) such as an immediate-release preparation, a sustained-release preparation and the like.

The pharmaceutical composition can be produced according to a method conventionally used in the field of pharmaceutical formulation, for example, the method described in the Japanese Pharmacopoeia, and the like.

While the content of the compound of the present invention in the pharmaceutical composition varies depending on the dosage form, dose of the compound of the present invention and the like, it is for example, about 0.1 to 100 wt %.

During production of an oral preparation, coating may be applied as necessary for the purpose of masking of taste, enteric property or durability.

Examples of the coating base to be used for coating include sugar coating base, water-soluble film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the water-soluble film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios. For coating, for example, a light shielding agent such as titanium oxide, red ferric oxide and the like can be used.

The compound of the present invention shows low toxicity (e.g., acute toxicity, chronic toxicity, genetic toxicity, reproductive toxicity, cardiotoxicity, carcinogenicity) and a few side effects. Therefore, it can be used as an agent for the prophylaxis or treatment or a diagnostic of various diseases in a mammal (e.g., human, bovine, horse, dog, cat, monkey, mouse, rat).

The compound of the present invention has a superior CH24H inhibitory action and can suppress nerve cell death, Aβ increase, intracerebral inflammation and the like.

Accordingly, the compound of the present invention is useful for the prophylaxis, improvement of symptoms, suppression of progression or treatment of diseases involving enhanced function of CH24H, for example, neurodegenerative disease.

In the present specification, the "neurodegenerative disease" means a disease associated with denaturation of neural tissues.

Specific examples of the neurodegenerative disease include Alzheimer's disease, mild cognitive disorder, Huntington's disease, Parkinson's disease, multiple sclerosis, amyotrophic lateral sclerosis, disorder or complication associated with brain injury (e.g., traumatic brain injury), post-concussional syndrome, shaken baby syndrome, cerebral infarction, glaucoma, neurodegenerative neurodegeneration deafness, frontotemporal dementia, spinal cord injury, dementia with Lewy bodies and the like.

In addition, the compound of the present invention is useful for the prophylaxis, improvement of symptoms, suppression of progression or treatment of diseases involving enhanced function of CH24H, for example, epilepsy, schizophrenia, convulsion, migraine, hepatic encephalopathy, age-related macular degeneration, pain (e.g., neuropathic pain, inflammatory pain), obsessive compulsive disorder, anxiety disorder, posttraumatic stress disorder, substance use disorder, schizophrenia, opsoclonus myoclonus syndrome, phantom limb pain, autism, opioid dependence, systemic lupus erythematosus and the like.

In addition, the compound of the present invention is useful for the prophylaxis, improvement of symptoms, suppression of progression or treatment of diseases involving CH24H-related inflammation, for example, AIDS-related dementia syndrome, major depression, radiation-induced somnolence syndrome, Down syndrome, and the like.

In addition, all compounds having a CH24H inhibitory action, which are described in the specifications of WO 2013/054822 filed on Oct. 3, 2012, PCT/JP2013/078008 filed on Oct. 15, 2013, and PCT/JP2013/083140 filed on Dec. 10, 2013, are also useful for the prophylaxis, improvement of symptoms, suppression of progression or treatment of the above-mentioned neurodegenerative disease, diseases involving enhanced function of CH24H, diseases involving CH24H-related inflammation, and the like.

The dose of the compound of the present invention varies depending on the administration subject, route of administration, target disease, symptoms, etc. For example, when it is administered orally to an adult patient (body weight 60 kg), its dose is about 0.01 to 100 mg/kg body weight per dose, preferably 0.05 to 30 mg/kg body weight per dose, more preferably 0.1 to 10 mg/kg body weight per dose and this amount is desirably administered in 1 to 3 portions daily.

When the compound of the present invention is applied to each of the above-mentioned diseases, it can be used in an appropriate combination with a medicament or a treatment method generally employed for the disease.

Examples of the medicament (hereinafter to be abbreviated as "concomitant drug") to be used in combination with the compound of the present invention include acetylcholine esterase inhibitors (e.g., donepezil, rivastigmine, galanthamine, zanapezil etc.), antidementia agents (e.g., memantine), inhibitors of β amyloid protein production, secretion, accumulation, coagulation and/or deposition, β secretase inhibitors (e.g., 6-(4-biphenyl)methoxy-2-[2-(N,N-dimethylamino)ethyl]tetralin, 6-(4-biphenyl)methoxy-2-(N,N-dimethylamino)methyltetralin, 6-(4-biphenyl)methoxy-2-(N,N-dipropylamino)methyltetralin, 2-(N,N-dimethylamino) methyl-6-(4'-methoxybiphenyl-4-yl)methoxytetralin, 6-(4-biphenyl)methoxy-2-[2-(N,N-diethylamino)ethyl]tetralin, 2-[2-(N,N-dimethylamino)ethyl]-6-(4'-methylbiphenyl-4-yl)methoxytetralin, 2-[2-(N,N-dimethylamino)ethyl]-6-(4'-methoxybiphenyl-4-yl)methoxytetralin, 6-(2',4'-dimethoxy-biphenyl-4-yl)methoxy-2-[2-(N,N-dimethylamino)ethyl] tetralin, 6-[4-(1,3-benzodioxol-5-yl)phenyl]methoxy-2-[2-(N,N-dimethylamino)ethyl]tetralin, 6-(3',4'-dimethoxybiphenyl-4-yl)methoxy-2-[2-(N,N-dimethylamino)ethyl]tetralin, an optically active form thereof, a salt thereof and a hydrate thereof, OM99-2 (WO01/00663)), γ secretase inhibitory agent, β amyloid protein coagulation inhibitory agent (e.g., PTI-00703, ALZHEMED (NC-531), PPI-368 (JP-A-11-514333), PPI-558 (JP-A-2001-500852), SKF-74652 (Biochem. J. (1999), 340(1), 283-289)), β amyloid vaccine, β amyloid degrading enzyme and the like, cerebral function activators (e.g., aniracetam, nicergoline), other therapeutic drug for Parkinson's disease [(e.g., dopamine receptor agonists (e.g., L-DOPA, bromocriptine, pergolide, talipexole, pramipexole, cabergoline, amantadine), a monoamine oxidase (MAO) inhibitors (e.g., deprenyl, Selgiline (selegiline), remacemide, riluzole), anticholinergic agents (e.g., trihexyphenidyl, biperiden), COMT inhibitors (e.g., entacapone)], therapeutic drug for amyotropic lateral sclerosis (e.g., rilu-zole etc., neurotrophic factor), therapeutic drug for abnormal behavior wandering and the like due to the progress of dementia (e.g., sedative drug, antianxiety drug), apoptosis inhibitors (e.g., CPI-1189, IDN-6556, CEP-1347), neuronal differentiation or regeneration promoters (e.g., leteprinim, xaliproden (SR-57746-A), SB-216763, Y-128, VX-853, pro- saptide, 5,6-dimethoxy-2-[2,2,4,6,7-pentamethyl-3-(4-methylphenyl)-2,3-dihydro-1-benzofuran-5-yl]isoindoline, 5,6-dimethoxy-2-[3-(4-isopropylphenyl)-2,2,4,6,7-pentamethyl-2,3-dihydro-1-benzofuran-5-yl]isoindoline, 6-[3-(4-isopropylphenyl)-2,2,4,6,7-pentamethyl-2,3-dihydro-1-benzofuran-5-yl]-6,7-dihydro-5H-[1,3]dioxolo[4,5-f]isoindole and optically active forms, salts and hydrates thereof), antidepressants (e.g., desipramine, amitriptyline, imipramine, tramadol), antiepilepsy drug (e.g., lamotrigine), antianxiety drugs (e.g., benzodiazepine), non-steroidal anti-inflammatory drugs (e.g., meloxicam, tenoxicam, indomethacin, ibuprofen, celecoxib, rofecoxib, aspirin), disease-modifying anti-rheumatic drugs (DMARDs), anti-cytokine drugs (e.g., TNF inhibitor MAP kinase inhibitor), steroidal drugs (e.g., dexamethasone, hexestrol, cortisone acetate), therapeutic agents for incontinence or frequent urination (e.g., flavoxate hydrochloride, oxybutynin hydrochloride, propiverine hydrochloride), phosphodiesterase inhibitors (e.g., sildenafil (citrate)), dopamine agonists (e.g., apomorphine etc.), antiarrhythmics (e.g., mexiletine), sex hormones or derivatives thereof (e.g., progesterone, estradiol, estradiol benzoate), therapeutic agents for osteoporosis (e.g., alfacalcidol, calcitriol, elcatonin, calcitonin salmon, estriol, ipriflavone, disodium pamidronate, sodium alendronate hydrate, disodium incadronate), parathyroid hormone (PTH), calcium receptor antagonists, therapeutic drugs for insomnia (e.g., benzodiazepine medicament, non-benzodiazepine medicament, melatonin agonist), therapeutic drugs for schizophrenia (e.g., typical antipsychotic agents such as haloperidol and the like; atypical antipsychotic agents such as clozapine, olanzapine, risperidone, aripiprazole and the like; medicament acted on metabotropic glutamate receptor or ionic channel-conjugated glutamate receptor; phosphodiesterase inhibitor) and the like.

In addition, a combined use with a transplantation method of neural stem cell or neural precursor cell prepared from embryonic stem cell or nervous tissue, or fetal neural tissue, and a combined use with a pharmaceutical agent such as an immunosuppressant after the transplantation and the like.

Furthermore, the compound of the present invention may be used in combination with the following concomitant drugs.

(1) Therapeutic Agent for Diabetes

For example, insulin preparations (e.g., animal insulin preparation extracted from the pancreas of bovine, swine; human insulin preparation genetically synthesized using *Escherichia coli*, yeast; zinc insulin; protamine zinc insulin; insulin fragment or derivatives (e.g., INS-1), oral insulin preparation), insulin sensitizer (e.g., pioglitazone or a salt thereof (preferably hydrochloride), rosiglitazone or a salt thereof (preferably maleate), Tesaglitazar, Ragaglitazar, Muraglitazar, Edaglitazone, Metaglidasen, Naveglitazar, AMG-131, THR-0921), α-glucosidase inhibitor (e.g., voglibose, acarbose, miglitol, emiglitate), biguanide (e.g., metformin, buformin or a salt thereof (e.g., hydrochloride, fumarate, succinate)), insulin secretagogue [sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof, glucose-dependent insulin secretagogue (e.g., [(3S)-6-({2',6'-dimethyl-4'-[3-(methylsulfonyl)propoxy]biphenyl-3-yl}methoxy)-2,3-dihydro-1-benzofuran-3-yl]acetic acid or a salt thereof)], dipeptidyl peptidase IV inhibitor (e.g., Alogliptin, Vildagliptin, Sitagliptin, Saxagliptin, T-6666, TS-021), β3 agonist (e.g., AJ-9677), GPR40 agonist, GLP-1 receptor agonist [e.g., GLP-1, GLP-1MR agent, NN-2211, AC-2993 (exendin-4), BIM-51077, Aib(8,35)hGLP-1(7,37)NH$_2$, CJC-1131], amylin agonist (e.g., pramlintide), phosphotyrosine phosphatase inhibitors (e.g., sodium vanadate), gluconeogenesis inhibitor (e.g., glycogen phosphorylase inhibitor glucose-6-phosphatase inhibitors, glucagon antagonists), SGLUT (sodium-glucose cotransporter) inhibitor (e.g., T-1095), 11β-hydroxysteroid dehydrogenase inhibitor (e.g., BVT-3498), adiponectin or an agonist thereof, IKK inhibitor (e.g., AS-2868), leptin resistance improving drugs, somatostatin receptor agonists, glucokinase activators (e.g., Ro-28-1675), GIP (Glucose-dependent insulinotropic peptide) and the like.

(2) Therapeutic Agents for Diabetic Complications

For example, aldose reductase inhibitors (e.g., tolrestat, epalrestat, zenarestat, zopolrestat, minalrestat, fidarestat, CT-112), neurotrophic factor and an increasing agent thereof (e.g., NGF, NT-3, BDNF, neurotrophic factors and increasing drugs described in WO01/14372 (e.g., 4-(4-chlorophenyl)-2-(2-methyl-1-imidazolyl)-5-[3-(2-methylphenoxy)propyl]oxazole)), nerve regeneration promoting agent (e.g., Y-128), PKC inhibitor (e.g., ruboxistaurin mesylate), AGE inhibitor (e.g., ALT946, pimagedine, pyratoxanthine, N-phenacylthiazolium bromide (ALT766), ALT-711, EXO-226, Pyridorin, pyridoxamine), active oxygen scavengers (e.g., thioctic acid), cerebral vasodilator (e.g., tiapuride, mexiletine), somatostatin receptor agonists (e.g., BIM23190), apoptosis signal regulating kinase-1 (ASK-1) inhibitor and the like can be mentioned.

(3) Therapeutic Agent for Hyperlipidemia

For example, statin compound (e.g., pravastatin, simvastatin, lovastatin, atorvastatin, fluvastatin, rosuvastatin, pitavastatin, or a salt thereof (e.g., sodium salt, calcium salt)), squalene synthase inhibitors (e.g., lapaquistat acetate or a salt thereof), fibrate compound (e.g., bezafibrate, clofibrate, simfibrate, clinofibrate), ACAT inhibitor (e.g., Avasimibe, Eflucimibe), anion exchange resin (e.g., colestyramine), probucol, nicotinic acid drug (e.g., nicomol, niceritrol), ethyl icosapentate, phytosterol (e.g., soysterol, gamma oryzanol) and the like.

(4) Antihypertensive Agent

For example, angiotensin converting enzyme inhibitor (e.g., captopril, enalapril, delapril), angiotensin II antagonist (e.g., candesartan cilexetil, losartan, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid, Azilsartan, Azilsartan medoxomil), calcium antagonist (e.g., manidipine, nifedipine, amlodipine, efonidipine, nicardipine), potassium channel opener (e.g., levcromakalim, L-27152, AL 0671, NIP-121), clonidine and the like.

(5) Antiobesity Agent

For example, central-acting antiobesity agent (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compounds described in WO01/82925 and WO01/87834); neuropeptide Y antagonist (e.g., CP-422935); cannabinoid receptor antagonists (e.g., SR-141716, SR-147778); ghrelin antagonist; 11β-hydroxysteroid dehydrogenase inhibitor (e.g., BVT-3498)), pancreatic lipase inhibitors (e.g., orlistat, cetilistat), β3 agonist (e.g., AJ-9677, AZ40140), anorectic peptides (e.g., leptin, CNTF (ciliary neurotrophic factor)), cholecystokinin agonist (e.g., lintitript, FPL-15849), anorexigenic agent (e.g., P-57) and the like.

(6) Diuretic

For example, xanthine derivative (e.g., theobromine sodium salicylate, theobromine calcium salicylate), thiazide preparation (e.g., ethiazide, cyclopenthiazide, trichloromethyazide, hydrochlorothiazide, hydroflumethiazide, benzylhydrochlorothiazide, penflutizide, polythiazide, methyclothiazide), antialdosterone preparation (e.g., spironolactone, triamterene), carbonic anhydrase inhibitors (e.g., acetazolamide), chlorobenzenesulfonamide agent (e.g., chlortalidone, mefruside, indapamide), azosemide, isosorbide, ethacrynic acid, piretanide, bumetanide, furosemide and the like.

(7) Chemotherapeutic Agent

For example, alkylating agents (e.g., cyclophosphamide, ifosfamide), metabolic antagonists (e.g., methotrexate, 5-fluorouracil or derivative thereof), antitumor antibiotics (e.g., mitomycin, adriamycin), plant-derived antitumor agents (e.g., vincristine, vindesine, Taxol), cisplatin, carboplatin, etoposide and the like. Of these, Furtulon and Neo-Furtulon, which are 5-fluorouracil derivatives, and the like are preferable.

(8) Immunotherapeutic Agent

For example, microorganism or bacterial components (e.g., muramyl dipeptide derivative, Picibanil), polysaccharides having immunity potentiating activity (e.g., lentinan, schizophyllan, krestin), cytokines obtained by genetic engineering techniques (e.g., interferon, interleukin (IL)), colony stimulating factors (e.g., granulocyte colony stimulating factor erythropoietin) and the like, with preference given to interleukins such as IL-1, IL-2, IL-12 and the like.

(9) Antithrombotic Agent

For example, heparin (e.g., heparin sodium, heparin calcium, dalteparin sodium), warfarin (e.g., warfarin potassium), anti-thrombin drug (e.g., argatroban), thrombolytic agent (e.g., urokinase, tisokinase, alteplase, nateplase, monteplase, pamiteplase), platelet aggregation inhibitor (e.g., ticlopidine hydrochloride, cilostazol, ethyl icosapentate, beraprost sodium, sarpogrelate hydrochloride) and the like.

(10) Cachexia Improving Medicament

For example, cyclooxygenase inhibitors (e.g., indomethacin etc.) [Cancer Research, Vol. 49, pages 5935-5939, 1989], progesterone derivatives (e.g., megestrol acetate)

[Journal of Clinical Oncology, Vol. 12, pages 213-225, 1994], glucosteroids (e.g., dexamethasone etc.), metoclopramide agents, tetrahydrocannabinol agents (publications are all as mentioned above), fat metabolism improving agents (e.g., eicosapentanoic acid etc.) [British Journal of Cancer, Vol. 68, pages 314-318, 1993], growth hormones, IGF-1, or antibodies to a cachexia-inducing factor such as TNF-α, LIF, IL-6, oncostatin M and the like.

Two or more kinds of the above-mentioned concomitant drugs may be used in combination at an appropriate ratio.

It is also possible to apply compound of the present invention to each of the above-mentioned diseases in combination with a biologic (e.g., antibody, vaccine preparation etc.), or as a combination therapy in combination with gene therapy method and the like.

Examples of the antibody and vaccine preparation include vaccine preparation to angiotensin II, vaccine preparation to CETP, CETP antibody, TNFα antibody and antibody to other cytokine, amyloid β vaccine preparation, type 1 diabetes vaccine (e.g., DIAPEP-277 manufactured by Peptor Ltd.), anti-HIV antibody, HIV vaccine preparation and the like, antibody or vaccine preparation to cytokine, renin-angiotensin enzyme and a product thereof, antibody or vaccine preparation to enzyme or protein involved in blood lipid metabolism, antibody or vaccine to enzyme or protein involved in blood coagulation or fibrinolytic system, antibody or vaccine preparation to protein involved in saccharometabolism or insulin resistance and the like.

In addition, a combined use with a biological preparation involved in a growth factor such as GH, IGF and the like is possible.

Examples of the gene therapy method include a treatment method using a gene relating to cytokine, renin-angiotensin enzyme and a product thereof, G protein, G protein conjugated receptor and its phosphorylation enzyme, a treatment method using a DNA decoy such as NFκB decoy and the like, a treatment method using an antisense, a treatment method using a gene relating to an enzyme or protein involved in blood lipid metabolism (e.g., gene relating to metabolism, excretion or absorption of cholesterol or triglyceride or HDL-cholesterol or blood phospholipid), a treatment method using a gene relating to an enzyme or protein involved in angiogenesis therapy targeting obstruction of peripheral vessel and the like (e.g., growth factors such as HGF, VEGF etc.), a treatment method using a gene relating to a protein involved in saccharometabolism or insulin resistance, an antisense to cytokine such as TNF and the like, and the like.

In addition, it is possible to use in combination with various organ regeneration methods such as heart regeneration, kidney regeneration, pancreas regeneration, blood vessel regeneration and the like or cell transplantation therapy utilizing bone marrow cell (myelomonocytic cell, myeloid stem cell) or an artificial organ utilizing tissue engineering (e.g., artificial blood vessel and cardiac muscle cell sheet).

The time of administration of the compound of the present invention and that of the concomitant drug are not limited, and they may be administered simultaneously or in a staggered manner to the administration subject. Furthermore, the compound of the present invention and the concomitant drug may be administered as two kinds of preparations containing each active ingredient, or a single preparation containing both active ingredients.

The dose of the concomitant drug can be appropriately determined based on the dose employed in clinical situations. The mixing ratio of the compound of the present invention and a concomitant drug can be appropriately determined depending on the administration subject, administration route, target disease, symptom, combination and the like. When the subject of administration is human, for example, a concomitant drug can be used in 0.01-100 parts by weight relative to 1 part by weight of the compound of the present invention.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bound silica gel. In HPLC (high performance liquid chromatography), C18 means use of octadecyl-bound silica gel. The ratios of elution solvents are volume mixing ratios, unless otherwise specified.

The abbreviations used in the specification mean the following.

THF: tetrahydrofuran
DME: 1,2-dimethoxyethane
DMF: N,N-dimethylformamide
DMA: N,N-dimethylacetamide
DMSO: dimethyl sulfoxide
ESI: Electron Spray Ionization
APCI: atmospheric pressure chemical ionization
M: mol concentration
IPE: diisopropyl ether
WSC: 1-[3-(dimethylamino)propyl]-3-ethylcarbodiimide
HATU: 2-(7-azabenzotriazol-1-yl)-1,1,3,3-tetramethyluronium hexafluorophosphate
HOBt: 1-hydroxybenzotriazole
HPLC: high-performance liquid chromatography
Pd(PPh$_3$)$_4$: tetrakis(triphenylphosphine)palladium(0)
DIPEA: N,N-diisopropylethylamine
IPA: isopropyl alcohol $^1$H NMR (protone nuclear magnetic resonance spectrum) was measured by Fourier-transform type NMR. For the analysis, ACD/SpecManager (trade name) and the like were used. Peaks with very mild protons such as a hydroxy group, an amino group and the like are not described.

MS (mass spectrum) was measured by LC/MS (liquid chromatography mass spectrometer). As API (Atmospheric Pressure Ionization), ESI (Electro Spray Ionization) method, or APCI (Atmospheric Pressure Chemical Ionization) method was used. The data indicates those found. Generally, a molecular ion peak ([M]+, [M+H]$^+$, [M−H]$^-$, etc.) is observed. In the case of a compound having a tert-butoxycarbonyl group (-Boc), a peak after elimination of a tert-butoxycarbonyl group or tert-butyl group may be observed as a fragment ion. In the case of a compound having a hydroxy group (—OH), a peak after elimination of H$_2$O may be observed as a fragment ion. In the case of a salt, a molecular ion peak or fragment ion peak of free form is generally observed.

The elemental analysis value (Anal.) shows Calculated value (Calcd) and Found value (Found).

Example 1

1-benzyl-4-(5-methyl-2-(pyridin-4-yl)benzoyl)piperazin-2-one

A) methyl 5-methyl-2-(pyridin-4-yl)benzoate

A mixture of methyl 2-bromo-5-methylbenzoate (5.2 g), pyridine-4-boronic acid (4.2 g), sodium carbonate (4.8 g), Pd(PPh$_3$)$_4$ (1.3 g), water (10 mL) and DME (50 mL) was heated with reflux overnight under nitrogen atmosphere. The reaction mixture was diluted with ethyl acetate, and filtered through silica gel. The filtrate was concentrated under reduced pressure, and the residue was purified by silica gel column chromatography (ethyl acetate/hexane) to give the title compound (2.5 g).

$^1$H NMR (300 MHz, CDCl$_3$) δ 2.45 (3H, s), 3.65 (3H, s), 7.18-7.25 (3H, m), 7.39 (1H, d, J=7.9 Hz), 7.73 (1H, s), 8.59-8.64 (2H, m).

B) 5-methyl-2-(pyridin-4-yl)benzoic acid hydrochloride

A mixture of methyl 5-methyl-2-(pyridin-4-yl)benzoate (8.8 g), 6M hydrochloric acid (65 mL) and acetic acid (100 mL) was heated with reflux overnight. The solvent was evaporated under reduced pressure, and the obtained solid was washed with ethyl acetate to give the title compound (6.6 g).

MS (APCI+): [M+H]$^+$ 214.3.

C) 4-(5-methyl-2-(pyridin-4-yl)benzoyl)piperazin-2-one

A mixture of 5-methyl-2-(pyridin-4-yl)benzoic acid hydrochloride (600 mg), piperazin-2-one (360 mg), HA= (1.4 g), triethylamine (1.7 mL) and DMF (6.0 mL) was stirred overnight. The mixture was poured into water, and extracted with ethyl acetate. The organic layer was washed with saturated brine, and dried over sodium sulfate, and the solvent was evaporated under reduced pressure. The residue was purified by silica gel column chromatography (NH, methanol/ethyl acetate) to give the title compound (170 mg).

$^1$H NMR (300 MHz, DMSO-d$_6$) δ 2.39-2.40 (3H, m), 2.80-4.13 (6H, m), 7.24-7.49 (5H, m), 7.88-7.99 (1H, m), 8.57-8.62 (2H, m).

D) 1-benzyl-4-(5-methyl-2-(pyridin-4-yl)benzoyl)piperazin-2-one

To a mixture of 4-(5-methyl-2-(pyridin-4-yl)benzoyl)piperazin-2-one (150 mg), benzyl bromide (0.10 mL) and DMF (2.0 mL) was added sodium hydride (31 mg) at room temperature, and the mixture was stirred at room temperature for 3 hr. The mixture was poured into water, and extracted with ethyl acetate. The organic layer was washed with saturated brine, and dried over sodium sulfate, and the solvent was evaporated under reduced pressure. The residue was filtered through NH silica gel, and purified by HPLC (C18, mobile phase: water/acetonitrile (containing 0.1% TFA)). To the obtained fraction was added saturated aqueous sodium hydrogencarbonate solution, and the mixture was extracted with ethyl acetate. The organic layer was dried over anhydrous magnesium sulfate, and concentrated under reduced pressure to give the title compound (90 mg).

$^1$H NMR (300 MHz, CDCl$_3$) δ 2.34-2.48 (3H, m), 2.90-4.67 (8H, m), 7.09-7.16 (2H, m), 7.21-7.40 (8H, m), 8.58-8.63 (2H, m).

Example 4

3-((1-benzylpiperidin-4-yl)oxy)-2,4'-bipyridine

A) 3-((1-benzylpiperidin-4-yl)oxy)-2-chloropyridine

To a mixture of 1-benzylpiperidin-4-ol (3.5 g), 2-chloropyridin-3-ol (2.0 g), triphenylphosphine (6.1 g) and THF (50 ml) was added diisopropyl azodicarboxylate (40% toluene solution) (13 mL) at room temperature, and the mixture was stirred overnight. The mixture was poured into water, and extracted with ethyl acetate. The organic layer was washed with saturated brine, and dried over sodium sulfate, and the solvent was evaporated under reduced pressure. The residue was purified by silica gel column chromatography (ethyl acetate/hexane) to give the title compound (4.5 g).

$^1$H NMR (300 MHz, CDCl$_3$) δ 1.83-2.03 (4H, m), 2.31-2.43 (2H, m), 2.65-2.79 (2H, m), 3.54 (2H, s), 4.36-4.46 (1H, m), 7.12-7.36 (7H, m), 7.98 (1H, dd, J=4.5, 1.5 Hz).

B) 3-((1-benzylpiperidin-4-yl)oxy)-2,4'-bipyridine

A mixture of 3-((1-benzylpiperidin-4-yl)oxy)-2-chloropyridine (540 mg), pyridin-4-ylboronic acid (330 mg), Pd(PPh$_3$)$_4$ (100 mg), sodium carbonate (570 mg), DME (3.0 ml) and water (0.6 ml) was irradiated with microwave at 150° C. for 1 hr. The mixture was poured into water, and extracted with ethyl acetate. The organic layer was washed with saturated brine, and dried over sodium sulfate, and the solvent was evaporated under reduced pressure. The residue was purified by silica gel column chromatography (NH, ethyl acetate/hexane), and the obtained solid was recrystallized from ethyl acetate to give the title compound (280 mg).

$^1$H NMR (300 MHz, CDCl$_3$) δ 1.73-1.92 (2H, m), 1.93-2.09 (2H, m), 2.23-2.41 (2H, m), 2.51-2.70 (2H, m), 3.49 (2H, s), 4.34-4.50 (1H, m), 7.21-7.37 (7H, m), 7.86-7.92 (2H, m), 8.33 (1H, dd, J=4.4, 1.3 Hz), 8.63-8.71 (2H, m).

Example 9 tert-butyl 4-(2-(pyridin-4-yl)phenoxy)piperidine-1-carboxylate

A) tert-butyl 4-(2-bromophenoxy)piperidine-1-carboxylate

To a mixture of tert-butyl 4-hydroxypiperidine-1-carboxylate (21 g), 2-bromophenol (10 mL), triphenylphosphine (34 g) and THF (250 mL) was added dropwise diisopropyl azodicarboxylate (40% toluene solution) (69 mL) at 0° C., and the mixture was stirred overnight at room temperature. The mixture was poured into water, and extracted with ethyl acetate. The organic layer was washed with saturated brine, and dried over sodium sulfate, and the solvent was evaporated under reduced pressure. The residue was purified by silica gel column chromatography (ethyl acetate/hexane) to give the title compound (24 g).

$^1$H NMR (300 MHz, CDCl$_3$) δ 1.47 (9H, s), 1.81-1.92 (4H, m), 3.43-3.55 (2H, m), 3.58-3.70 (2H, m), 4.52-4.60 (1H, m), 6.80-6.88 (1H, m), 6.92 (1H, d, J=7.9 Hz), 7.20-7.24 (1H, m), 7.54 (1H, dd, J=7.9, 1.1 Hz).

B) tert-butyl 4-(2-(pyridin-4-yl)phenoxy)piperidine-1-carboxylate

A mixture of tert-butyl 4-(2-bromophenoxy)piperidine-1-carboxylate (2.0 g), pyridin-4-ylboronic acid (690 mg), Pd(PPh$_3$)$_4$ (320 mg), sodium carbonate (1.8 g), DME (9.4 mL) and water (1.9 mL) was irradiated with microwave at 150° C. for 1.5 hr. The mixture was poured into saturated aqueous sodium carbonate solution, and extracted with ethyl acetate. The organic layer was separated, washed with saturated brine, and dried, and the solvent was evaporated under reduced pressure. The residue was purified by silica gel column chromatography (ethyl acetate/hexane) to give the title compound (820 mg).

$^1$H NMR (300 MHz, CDCl$_3$) δ 1.44 (9H, s), 1.66-1.93 (4H, m), 3.13-3.63 (4H, m), 4.49 (1H, m), 6.87-7.19 (2H, m), 7.30-7.41 (2H, m), 7.42-7.56 (2H, m), 8.52-8.73 (2H, m).

Example 11 phenyl(4-(2-(pyridin-4-yl)phenoxy)piperidin-1-yl)methanone

A) 4-(2-(piperidin-4-yloxy)phenyl)pyridine dihydrochloride

A mixture of tert-butyl 4-(2-(pyridin-4-yl)phenoxy)piperidine-1-carboxylate (4.1 g) and 5-10% hydrogen chloride/ methanol (30 mL) was stirred overnight at room temperature. The resulting solid was collected by filtration, and washed with IPA and ethyl acetate to give the title compound (1.3 g). Then, the filtrate was concentrated under reduced pressure, and the residue was washed with IPA and ethyl acetate to give the title compound (2.3 g).

$^1$H NMR (300 MHz, DMSO-d$_6$) δ 1.80-1.96 (2H, m), 2.05-2.21 (2H, m), 4.78-4.91 (1H, m), 7.13-7.24 (1H, m), 7.36 (1H, d, J=8.3 Hz), 7.51-7.66 (2H, m), 8.20 (2H, d, J=6.8 Hz), 8.93 (2H, d, J=6.8 Hz), 9.16 (1H, brs), 9.36 (1H, brs).

B) phenyl(4-(2-(pyridin-4-yl)phenoxy)piperidin-1-yl)methanone

To a mixture of 4-(2-(piperidin-4-yloxy)phenyl)pyridine dihydrochloride (300 mg), triethylamine (0.64 mL) and DMF (3.0 mL) was added dropwise benzoyl chloride (0.13 mL) at room temperature, and the mixture was stirred at room temperature for 2 hr. The mixture was diluted with water, and extracted with ethyl acetate. The organic layer was washed with saturated brine, and dried over sodium sulfate, and the solvent was evaporated under reduced pressure. The residue was purified by silica gel column chromatography (NH, ethyl acetate/hexane) to give the title compound (270 mg).

$^1$H NMR (300 MHz, CDCl$_3$) δ 1.84 (4H, brs), 3.13-4.00 (4H, m), 4.55-4.64 (1H, m), 7.02 (1H, d, J=8.3 Hz), 7.08 (1H, td, J=7.6, 1.1 Hz), 7.33-7.41 (7H, m), 7.47 (2H, dd, J=4.5, 1.9 Hz), 8.64 (2H, dd, J=4.5, 1.9 Hz).

Example 16

4-(2-((1-((1-methyl-1H-imidazol-2-yl)methyl)piperidin-4-yl)oxy)phenyl)pyridine

A) 4-(2-(piperidin-4-yloxy)phenyl)pyridine

To 4-(2-(piperidin-4-yloxy)phenyl)pyridine dihydrochloride (2.3 g) was added 1M aqueous sodium hydroxide solution (20 mL), and the mixture was stirred at room temperature for 5 min. The mixture was diluted with saturated brine, and extracted with ethyl acetate. The organic layer was dried over sodium sulfate, and the solvent was evaporated under reduced pressure to give the title compound (1.7 g).

$^1$H NMR (300 MHz, CDCl$_3$) δ 1.47 (1H, brs), 1.55-1.70 (2H, m), 1.86-1.98 (2H, m), 2.60-2.72 (2H, m), 2.92-3.04 (2H, m), 4.33-4.46 (1H, m), 6.97-7.09 (2H, m), 7.30-7.40 (2H, m), 7.45-7.54 (2H, m), 8.57-8.66 (2H, m).

B) 4-(2-((1-((1-methyl-1H-imidazol-2-yl)methyl)piperidin-4-yl)oxy)phenyl)pyridine To a mixture of 4-(2-(piperidin-4-yloxy)phenyl)pyridine (220 mg) and acetonitrile (4.0 mL) was added 1-methyl-1H-imidazole-2-carbaldehyde (110 mg), and the mixture was stirred at room temperature for 10 min. To the mixture were added sodium triacetoxyborohydride (370 mg) and acetic acid (0.10 mL), and the mixture was stirred overnight at room temperature. To the mixture was added saturated aqueous sodium carbonate solution, and the mixture was extracted with ethyl acetate. The organic layer was dried, and the solvent was evaporated under reduced pressure. The obtained solid was recrystallized from ethyl acetate to give the title compound (140 mg).

$^1$H NMR (300 MHz, CDCl$_3$) δ 1.59-1.78 (2H, m), 1.81-2.04 (2H, m), 2.27 (2H, m), 2.43-2.75 (2H, m), 3.54 (2H, s), 3.68 (3H, s), 4.32 (1H, m), 6.83 (1H, m), 6.91 (1H, m), 6.95-7.13 (2H, m), 7.29-7.41 (2H, m), 7.41-7.56 (2H, m), 8.38-8.71 (2H, m).

Example 22

3-((1-((1-methyl-1H-pyrazol-4-yl)methyl)piperidin-4-yl)oxy)-2,4'-bipyridine

A) 3-(piperidin-4-yloxy)-2,4'-bipyridine

A mixture of 3-((1-benzylpiperidin-4-yl)oxy)-2,4'-bipyridine (440 mg), ammonium formate (400 mg), 10% palladium on carbon (140 mg) and methanol (5.0 mL) was heated with reflux for 6 hr. The mixture was filtered through Celite, and the filtrate was concentrated under reduced pressure. The residue was purified by silica gel column chromatography (NH, methanol/ethyl acetate) to give the title compound (220 mg).

$^1$H NMR (300 MHz, CDCl$_3$) δ 1.64-1.78 (2H, m), 1.91-2.10 (2H, m), 2.72 (2H, ddd, J=12.4, 8.7, 3.3 Hz), 2.98-3.13 (2H, m), 4.39-4.54 (1H, m), 7.21-7.41 (2H, m), 7.92 (2H, d, J=6.1 Hz), 8.34 (1H, d, J=4.3 Hz), 8.68 (2H, d, J=6.0 Hz).

B) 3-((1-((1-methyl-1H-pyrazol-4-yl)methyl)piperidin-4-yl)oxy)-2,4'-bipyridine

To a mixture of 3-(piperidin-4-yloxy)-2,4'-bipyridine (100 mg) and acetonitrile (2.0 mL) was added 1-methyl-1H-pyrazole-4-carbaldehyde (43 mg), and the mixture was stirred for 10 min. To the mixture were added sodium triacetoxyborohydride (170 mg) and acetic acid (0.045 mL), and the mixture was stirred at room temperature for 2 hr. To the mixture was added sodium triacetoxyborohydride (170 mg), and the mixture was stirred at room temperature for 2 hr. The mixture was poured into 2M aqueous sodium hydroxide solution, and extracted with ethyl acetate. The organic layer was dried, and the solvent was evaporated under reduced pressure. The residue was purified by silica gel column chromatography (ethyl acetate/hexane), and the obtained solid was recrystallized from ethyl acetate/hexane to give the title compound (61 mg).

$^1$H NMR (300 MHz, CDCl$_3$) δ 1.72-1.89 (2H, m), 1.91-2.07 (2H, m), 2.32 (2H, m), 2.59 (2H, m), 3.39 (2H, s), 3.87 (3H, s), 4.29-4.56 (1H, m), 7.14-7.47 (4H, m), 7.70-8.01 (2H, m), 8.33 (1H, m), 8.53-8.91 (2H, m).

Example 29

1-((4-fluoro-2-(pyridin-4-yl)phenyl)sulfonyl)-4-(4-methoxybenzyl)piperazine

A) 1-((2-bromo-4-fluorophenyl)sulfonyl)-4-(4-methoxybenzyl) piperazine

To a mixture of 1-(4-methoxybenzyl)piperazine (0.75 g), triethylamine (1.5 mL) and DMF (10 mL) was added 2-bromo-4-fluorobenzene-1-sulfonyl chloride (1.0 g) at room temperature, and the mixture was stirred overnight. The mixture was poured into water, and extracted with ethyl acetate. The organic layer was washed with saturated brine, and dried over sodium sulfate, and the solvent was evaporated under reduced pressure. The residue was purified by silica gel column chromatography (ethyl acetate/hexane) to give the title compound (1.6 g).

¹H NMR (300 MHz, CDCl₃) δ 2.43-2.52 (4H, m), 3.24-3.33 (4H, m), 3.79 (3H, s), 6.80-6.87 (2H, m), 7.09-7.22 (3H, m), 7.48 (1H, dd, J=8.1, 2.5 Hz), 8.08 (1H, dd, J=8.9, 5.9 Hz).

B) 1-((4-fluoro-2-(pyridin-4-yl)phenyl)sulfonyl)-4-(4-methoxybenzyl)piperazine

A mixture of 1-((2-bromo-4-fluorophenyl)sulfonyl)-4-(4-methoxybenzyl)piperazine (500 mg), pyridin-4-ylboronic acid (210 mg), Pd(PPh₃)₄ (65 mg), sodium carbonate (360 mg), DME (2.5 mL) and water (0.50 mL) was irradiated with microwave at 150° C. for 1 hr. The mixture was poured into water, and extracted with ethyl acetate. The organic layer was washed with saturated brine, and dried over sodium sulfate, and the solvent was evaporated under reduced pressure. The residue was purified by silica gel column chromatography (ethyl acetate/hexane) and silica gel column chromatography (NH, ethyl acetate/hexane) to give the title compound (430 mg).
¹H NMR (300 MHz, CDCl₃) δ 2.16-2.27 (4H, m), 2.76-2.86 (4H, m), 3.36 (2H, s), 3.79 (3H, s), 6.79-6.86 (2H, m), 7.00 (1H, dd, J=8.7, 2.7 Hz), 7.13 (2H, d, J=8.3 Hz), 7.18-7.26 (1H, m), 7.30-7.37 (2H, m), 8.12 (1H, dd, J=9.1, 5.7 Hz), 8.61-8.68 (2H, m).

Example 40

2-((1-((1-methyl-1H-pyrazol-4-yl)methyl)piperidin-4-yl)oxy)-3-(pyridin-4-yl)pyrazine A) tert-butyl 4-((3-chloropyrazin-2-yl)oxy)piperidine-1-carboxylate To a mixture of tert-butyl 4-hydroxypiperidine-1-carboxylate (1.4 g) and DMF (20 mL) was added sodium hydride (0.30 g) at 0° C., and the mixture was stirred for 20 min. To the mixture was added 2,3-dichloropyrazine (1.5 g), and the mixture was stirred at 90° C. for 5 hr, and then overnight at room temperature. The mixture was poured into saturated sodium hydrogencarbonate solution, and extracted with ethyl acetate. The organic layer was dried, and the solvent was evaporated under reduced pressure. The residue was purified by silica gel column chromatography (ethyl acetate/hexane) to give the title compound (1.3 g).
¹H NMR (300 MHz, CDCl₃) δ 1.48 (9H, s), 1.70-1.91 (2H, m), 1.91-2.06 (2H, m), 3.42 (2H, m), 3.60-3.84 (2H, m), 5.30 (1H, m), 7.95 (2H, m).

B) tert-butyl 4-((3-(pyridin-4-yl)pyrazin-2-yl)oxy)piperidine-1-carboxylate

A mixture of tert-butyl 4-((3-chloropyrazin-2-yl)oxy)piperidine-1-carboxylate (1.3 g), sodium carbonate (1.3 g), Pd(PPh₃)₄ (0.24 g), pyridin-4-ylboronic acid (0.76 g), DME (7.0 mL) and water (1.4 mL) was irradiated with microwave at 150° C. for 1 hr. The mixture was poured into saturated sodium hydrogencarbonate solution, and extracted with ethyl acetate. The organic layer was dried, and the solvent was evaporated under reduced pressure. The residue was purified by silica gel column chromatography (ethyl acetate/hexane) to give the title compound (1.0 g).
¹H NMR (300 MHz, CDCl₃) δ 1.37-1.54 (9H, m), 1.85 (2H, m), 1.95-2.18 (2H, m), 3.22-3.52 (2H, m), 3.58-3.85 (2H, m), 5.42 (1H, m), 7.91-8.05 (2H, m), 8.13 (1H, m), 8.29 (1H, m), 8.60-8.83 (2H, m).

C) 2-(piperidin-4-yloxy)-3-(pyridin-4-yl)pyrazine

A mixture of tert-butyl 4-((3-(pyridin-4-yl)pyrazin-2-yl)oxy)piperidine-1-carboxylate (1.0 g) and 5% hydrogen chloride/methanol (10 g) was heated with reflux for 1 hr. The mixture was concentrated under reduced pressure. To the residue were added water and 2M aqueous sodium hydroxide solution, and the mixture was extracted with ethyl acetate. The organic layer was dried, and the solvent was evaporated under reduced pressure to give the title compound (640 mg).
¹H NMR (300 MHz, CDCl₃) δ 1.77 (2H, m), 1.96-2.29 (2H, m), 2.82 (2H, m), 3.01-3.28 (2H, m), 5.35 (1H, m), 7.93-8.07 (2H, m), 8.12 (1H, m), 8.27 (1H, m), 8.61-8.89 (2H, m).

D) 2-((1-((1-methyl-1H-pyrazol-4-yl)methyl)piperidin-4-yl)oxy)-3-(pyridin-4-yl)pyrazine To a mixture of 2-(piperidin-4-yloxy)-3-(pyridin-4-yl)pyrazine (210 mg), 1-methyl-1H-pyrazole-4-carbaldehyde (90 mg) and THF (4.0 mL) were added acetic acid (0.094 mL) and sodium triacetoxyhydroborate (350 mg), and the mixture was stirred overnight at room temperature. The mixture was poured into saturated sodium hydrogencarbonate solution, and extracted with ethyl acetate. The organic layer was dried over sodium sulfate, and the solvent was evaporated under reduced pressure. The residue was purified by silica gel column chromatography (ethyl acetate/hexane), and crystallized from hexane/diethyl ether, and the obtained solid was recrystallized from ethyl acetate to give the title compound (130 mg).
¹H NMR (300 MHz, CDCl₃) δ 1.91 (2H, m), 2.02-2.24 (2H, m), 2.40 (2H, m), 2.70 (2H, brs), 3.45 (2H, s), 3.88 (3H, s), 5.28 (1H, m), 7.27-7.32 (1H, m), 7.41 (1H, s), 7.91-8.06 (2H, m), 8.11 (1H, dm), 8.26 (1H, m), 8.56-8.82 (2H, m).

Example 47

3-((1-(1,3-thiazol-4-ylmethyl)piperidin-4-yl)oxy)-2,4'-bipyridine

To a mixture of 3-(piperidin-4-yloxy)-2,4'-bipyridine (150 mg), 1,3-thiazole-4-carbaldehyde (67 mg) and THF (3 mL) were added acetic acid (0.067 mL) and sodium triacetoxyhydroborate (250 mg), and the mixture was stirred overnight at room temperature. The mixture was poured into saturated sodium hydrogencarbonate solution, and extracted with ethyl acetate. The organic layer was separated, washed with saturated brine, and dried, and the solvent was evaporated under reduced pressure. The residue was purified by silica gel column chromatography (ethyl acetate/hexane), the obtained oil was crystallized from hexane, and the obtained solid was recrystallized from ethyl acetate/hexane to give the title compound (90 mg).
¹H NMR (300 MHz, CDCl₃) δ 1.76-2.20 (4H, m), 2.25-2.79 (4H, m), 3.73 (2H, s), 4.46 (1H, brs), 7.08-7.38 (3H, m), 7.89 (2H, m), 8.33 (1H, m), 8.52-8.88 (3H, m). MS (API+): [M+H]⁺ 353.1

Example 54

2-(3,3-difluoro-4-((3-(pyridin-4-yl)pyrazin-2-yl)oxy)piperidin-1-yl)-N,N-dimethylacetamide A) tert-butyl 4-((3-chloropyrazin-2-yl)oxy)-3,3-difluoropiperidine-1-carboxylate To a mixture of tert-butyl 3,3-difluoro-4-hydroxypiperidine-1-carboxylate (400 mg) and DMF (6.0 mL) was added sodium hydride (88 mg) at 0° C., and the mixture was stirred for 15 min. To the mixture was added 2,3-dichloropyrazine (250 mg), and the mixture was stirred overnight at room temperature. The mixture was poured into saturated sodium hydrogencarbonate, and extracted with ethyl acetate. The organic layer was dried, and the solvent was evaporated under reduced pressure. The residue was purified by silica gel column chromatography (ethyl acetate/hexane) to give the title compound (440 mg).

$^1$H NMR (300 MHz, CDCl$_3$) δ 1.39-1.52 (9H, m), 1.90-2.29 (2H, m), 3.39 (1H, m), 3.56-3.91 (2H, m), 3.91-4.28 (1H, m), 5.60 (1H, m), 8.02 (2H, s).

B) tert-butyl 3,3-difluoro-4-((3-(pyridin-4-yl)pyrazin-2-yl)oxy)piperidine-1-carboxylate A mixture of tert-butyl 4-((3-chloropyrazin-2-yl)oxy)-3,3-difluoropiperidine-1-carboxylate (440 mg), Pd(PPh$_3$)$_4$ (73 mg), sodium carbonate (400 mg), pyridin-4-ylboronic acid (230 mg), DME (2.5 mL) and water (0.50 mL) was irradiated with microwave at 150° C. for 1 hr. The mixture was poured into saturated sodium hydrogencarbonate solution, and extracted with ethyl acetate. The organic layer was dried, and the solvent was evaporated under reduced pressure. The residue was purified by silica gel column chromatography (NH, ethyl acetate/hexane) to give the title compound (340 mg).

$^1$H NMR (300 MHz, CDCl$_3$) δ 1.42-1.51 (9H, s), 1.95-2.11 (1H, m), 2.16 (1H, brs), 3.52 (2H, m), 3.72-3.93 (2H, m), 5.46-5.82 (1H, m), 7.79-8.02 (2H, m), 8.14 (1H, m), 8.38 (1H, m), 8.60-8.82 (2H, m).

C) 2-((3,3-difluoropiperidin-4-yl)oxy)-3-(pyridin-4-yl)pyrazine

A mixture of tert-butyl 3,3-difluoro-4-((3-(pyridin-4-yl)pyrazin-2-yl)oxy)piperidine-1-carboxylate (340 mg) and 5% hydrogen chloride/methanol (3.1 g) was stirred overnight at room temperature. The mixture was concentrated under reduced pressure. To the residue were added water and 2M aqueous sodium hydroxide solution, and the mixture was extracted with ethyl acetate. The organic layer was dried, and the solvent was evaporated under reduced pressure to give the title compound (230 mg).

$^1$H NMR (300 MHz, DMSO-d$_6$) δ 1.71-1.94 (1H, m), 2.12 (1H, m), 2.62-3.19 (4H, m), 5.50-5.81 (1H, m), 7.80-8.10 (2H, m), 8.35 (1H, m), 8.49 (1H, m), 8.62-8.85 (2H, m).

D) 2-(3,3-difluoro-4-((3-(pyridin-4-yl)pyrazin-2-yl)oxy)piperidin-1-yl)-N,N-dimethylacetamide A mixture of 2-((3,3-difluoropiperidin-4-yl)oxy)-3-(pyridin-4-yl)pyrazine (120 mg), potassium carbonate (110 mg), 2-chloro-N,N-dimethylacetamide (48 mg) and THF (3.0 mL) was stirred overnight at room temperature. The mixture was poured into saturated sodium hydrogencarbonate solution, and extracted with ethyl acetate. The organic layer was dried, and the solvent was evaporated under reduced pressure. The residue was purified by silica gel column chromatography (NH, ethyl acetate/hexane), the obtained oil was crystallized from ethyl acetate/hexane, and the obtained solid was recrystallized from ethyl acetate to give the title compound (84 mg).

$^1$H NMR (300 MHz, CDCl$_3$) δ 1.94-2.37 (2H, m), 2.64-2.88 (2H, m), 2.90-3.23 (7H, m), 3.38 (1H, s), 3.51-4.11 (1H, m), 4.76 (1H, s), 5.46-5.81 (1H, m), 7.90-8.07 (2H, m), 8.09-8.20 (1H, m), 8.27-8.44 (1H, m), 8.62-8.87 (2H, m).

Example 55

1-(2,4'-bipyridin-3-ylmethyl)-4-(4-fluorobenzyl)piperazin-2-one

A) (2,4'-bipyridine)-3-ylmethanol

A mixture of Pd(PPh$_3$)$_4$ (0.62 g), (2-bromopyridin-3-yl)methanol (1.0 g), sodium carbonate (1.7 g), pyridin-4-ylboronic acid (0.98 g), DME (8.0 mL) and water (1.6 mL) was irradiated with microwave at 150° C. for 1 hr. The mixture was poured into 2M aqueous sodium hydroxide solution, and extracted with ethyl acetate. The organic layer was dried, and the solvent was evaporated under reduced pressure. The obtained solid was washed with warmed methanol, and the filtrate was concentrated under reduced pressure. The residue was purified by silica gel column chromatography (methanol/ethyl acetate) to give the title compound (460 mg).

$^1$H NMR (300 MHz, CDCl$_3$) δ 2.18 (1H, s), 4.71 (2H, m), 7.39 (1H, m), 7.49-7.57 (2H, m), 7.98 (1H, m), 8.67 (1H, m), 8.69-8.74 (2H, m).

B) tert-butyl 4-((2,4'-bipyridine)-3-ylmethyl)-3-oxopiperazine-1-carboxylate

A mixture of (2,4'-bipyridine)-3-ylmethanol (360 mg) and thionyl chloride (2.8 mL) was stirred at 0° C. for 1 hr. To the mixture was added toluene, and the mixture was stirred at 0° C. for 20 min. The mixture was filtered, to the obtained solid were added methanol and silica gel (NH). The mixture was filtered, and the filtrate was concentrated under reduced pressure to give 3-(chloromethyl)-2,4'-bipyridine (420 mg). To a mixture of tert-butyl 3-oxopiperazine-1-carboxylate (410 mg) and DMF (10 mL) was added sodium hydride (150 mg) at 0° C., and the mixture was stirred for 15 min. To the mixture was added dropwise a solution of 3-(chloromethyl)-2,4'-bipyridine (420 mg) obtained above in DMF (4 mL). The mixture was stirred for 3 hr while raising the temperature from 0° C. to room temperature. The mixture was poured into saturated sodium hydrogencarbonate solution, and extracted with ethyl acetate. The organic layer was dried, and the solvent was evaporated under reduced pressure. The residue was purified by silica gel column chromatography (NH, ethyl acetate/hexane) to give the title compound (390 mg).

$^1$H NMR (300 MHz, CDCl$_3$) δ 1.46 (9H, s), 3.03 (2H, m), 3.34-3.63 (3H, m), 4.09-4.15 (2H, m), 4.73 (2H, s), 7.37 (1H, m), 7.39-7.51 (2H, m), 7.69 (1H, m), 8.66 (1H, m), 8.69-8.79 (2H, m).

C) 1-((2,4'-bipyridine)-3-ylmethyl)piperazin-2-one

A mixture of tert-butyl 4-((2,4'-bipyridine)-3-ylmethyl)-3-oxopiperazine-1-carboxylate (73 mg) and 5% hydrogen chloride/methanol (720 mg) was stirred at 70° C. for 1 hr. The mixture was concentrated under reduced pressure. To the residue were added water and 2M aqueous sodium hydroxide solution, and the mixture was extracted with ethyl acetate. The organic layer was dried, and the solvent was evaporated under reduced pressure to give the title compound (25 mg).

MS (API+): [M+H]$^+$ 269.2

D) 1-(2,4'-bipyridin-3-ylmethyl)-4-(4-fluorobenzyl)piperazin-2-one

To a mixture of 1-((2,4'-bipyridine)-3-ylmethyl)piperazin-2-one (80 mg), 4-fluorobenzaldehyde (37 mg) and THF (3.0 mL) were added acetic acid (0.034 mL) and sodium triacetoxyhydroborate (130 mg), and the mixture was stirred overnight at room temperature. The mixture was poured into saturated aqueous sodium carbonate solution, and extracted with ethyl acetate. The organic layer was dried, and the solvent was evaporated under reduced pressure. The residue was purified by silica gel column chromatography (NH, ethyl acetate/hexane) and HPLC (C18, mobile phase: water/acetonitrile (containing 0.1% TFA)), to the obtained fraction was added saturated aqueous sodium hydrogencarbonate solution, and the mixture was extracted with ethyl acetate. The organic layer was dried over anhydrous magnesium sulfate, and concentrated under reduced pressure to give the title compound (4.0 mg).

$^1$H NMR (300 MHz, CDCl$_3$) δ 2.50-2.65 (2H, m), 2.90-3.05 (2H, m), 3.18 (2H, s), 3.50 (2H, s), 4.70 (2H, s), 6.85-7.06 (2H, m), 7.19-7.27 (2H, m), 7.36 (1H, m), 7.40-7.46 (2H, m), 7.70 (1H, m), 8.64 (1H, m), 8.69-8.80 (2H, m).

Example 61

3-((1-benzylpyrrolidin-3-yl)oxy)-2,4'-bipyridine

A) 3-((1-benzylpyrrolidin-3-yl)oxy)-2-chloropyridine

A mixture of 1-benzylpyrrolidin-3-ol (1.6 g), 2-chloro-3-hydroxypyridine (1.0 g), triphenylphosphine (3.0 g), diisopropyl azodicarboxylate (40% toluene solution) (6.1 mL) and THF (25 mL) was stirred at room temperature for 3 hr. The mixture was poured into water, and extracted with ethyl acetate. The organic layer was washed with saturated brine, and dried over magnesium sulfate, and the solvent was evaporated under reduced pressure. The residue was purified by silica gel column chromatography (NH, ethyl acetate/hexane) and silica gel column chromatography (ethyl acetate/hexane) to give the title compound (2.1 g).

$^1$H NMR (300 MHz, CDCl$_3$) δ 1.97-2.10 (1H, m), 2.24-2.39 (1H, m), 2.65-2.82 (3H, m), 3.11 (1H, dd, J=10.5, 6.3 Hz), 3.69 (2H, s), 4.84 (1H, tt, J=6.8, 3.4 Hz), 7.04-7.19 (2H, m), 7.21-7.39 (5H, m), 7.97 (1H, dd, J=4.6, 1.6 Hz).

B) 3-((1-benzylpyrrolidin-3-yl)oxy)-2,4'-bipyridine

A mixture of Pd(PPh$_3$)$_4$ (0.20 g), 3-((1-benzylpyrrolidin-3-yl)oxy)-2-chloropyridine (1.0 g), sodium carbonate (1.1 g), pyridin-4-ylboronic acid (0.64 g), DME (10 mL) and water (2.0 mL) was irradiated with microwave at 150° C. for 1.5 hr. The mixture was poured into saturated brine, and extracted with ethyl acetate. The organic layer was dried over magnesium sulfate, and the solvent was evaporated under reduced pressure. The residue was purified by silica gel column chromatography (methanol/ethyl acetate), and the part was purified by HPLC (C18, mobile phase: water/acetonitrile (containing 10 mM NH$_4$HCO$_3$)) to give the title compound (64 mg).

$^1$H NMR (300 MHz, CDCl$_3$) δ 1.93-2.08 (1H, m), 2.25-2.40 (1H, m), 2.63 (1H, td, J=8.3, 5.7 Hz), 2.70-2.86 (2H, m), 2.98 (1H, dd, J=10.5, 5.9 Hz), 3.56-3.78 (2H, m), 4.80-4.97 (1H, m), 7.17-7.30 (3H, m), 7.31-7.35 (4H, m), 7.91-7.98 (2H, m), 8.33 (1H, dd, J=4.3, 1.5 Hz), 8.63-8.73 (2H, m).

Example 64

3-((1-((4-methoxyphenyl)sulfonyl)pyrrolidin-3-yl)oxy)-2,4'-bipyridine

A) 3-(pyrrolidin-3-yloxy)-2,4'-bipyridine

A mixture of 3-((1-benzylpyrrolidin-3-yl)oxy)-2,4'-bipyridine (300 mg), ammonium formate (285 mg), 10% palladium on carbon (96 mg) and methanol (5 mL) was heated with reflux for 6 hr. The mixture was filtered through Celite, and the filtrate was concentrated under reduced pressure. The residue was purified by silica gel column chromatography (NH, methanol/ethyl acetate) to give the title compound (180 mg).

$^1$H NMR (300 MHz, CDCl$_3$) δ 1.91-2.21 (2H, m), 2.95 (1H, ddd, J=11.2, 8.3, 5.3 Hz), 3.06-3.24 (3H, m), 4.91 (1H, ddt, J=6.3, 4.4, 2.0 Hz), 7.28-7.33 (2H, m), 7.81-7.90 (2H, m), 8.35 (1H, dd, J=3.6, 2.3 Hz), 8.60-8.73 (2H, m).

B) 3-((1-((4-methoxyphenyl)sulfonyl)pyrrolidin-3-yl)oxy)-2,4'-bipyridine

To a mixture of 3-(pyrrolidin-3-yloxy)-2,4'-bipyridine (80 mg), triethylamine (0.14 mL) and DMF (2.0 mL) was added p-methoxybenzenesulfonyl chloride (75 mg) at 0° C., and the mixture was stirred at room temperature for 4 hr. Water was poured into the mixture, and the mixture was extracted with ethyl acetate. The organic layer was washed with water and saturated brine, and dried over magnesium sulfate, and the solvent was evaporated under reduced pressure. The residue was washed with ethyl acetate, and the obtained solid was recrystallized from ethanol/IPE to give the title compound (52 mg).

$^1$H NMR (300 MHz, CDCl$_3$) δ 2.08-2.21 (2H, m), 3.17-3.29 (1H, m), 3.47 (1H, d, J=11.7 Hz), 3.56 (1H, ddd, J=9.4, 7.1, 3.9 Hz), 3.70 (1H, dd, J=11.8, 4.8 Hz), 3.80 (3H, s), 4.81-4.94 (1H, m), 6.81-6.88 (2H, m), 7.13-7.18 (1H, m), 7.27-7.31 (1H, m), 7.58-7.72 (4H, m), 8.37 (1H, dd, J=4.6, 1.2 Hz), 8.52-8.64 (2H, m).

Example 67

(4-(2,4'-bipyridin-3-yloxy)piperidin-1-yl)(cyclopropyl)methanone

A mixture of 3-(piperidin-4-yloxy)-2,4'-bipyridine (70 mg), cyclopropanecarboxylic acid (0.033 mL), HOBt anhydride (56 mg), WSC hydrochloride (79 mg) and DMF (1.0 mL) was stirred at room temperature for 6 hr. The mixture was diluted with 1M aqueous sodium hydroxide solution and ethyl acetate, and extracted with ethyl acetate. The organic layer was washed with saturated brine, and dried over magnesium sulfate, and the solvent was evaporated under reduced pressure. The residue was purified by silica gel column chromatography (methanol/ethyl acetate) to give the title compound (61 mg).

$^1$H NMR (300 MHz, CDCl$_3$) δ 0.68-0.80 (2H, m), 0.94-1.02 (2H, m), 1.66-1.77 (1H, m), 1.79-2.02 (4H, m), 3.66 (4H, brs), 4.63 (1H, tt, J=6.4, 3.4 Hz), 7.28-7.40 (2H, m), 7.84-7.90 (2H, m), 8.38 (1H, dd, J=4.3, 1.5 Hz), 8.66-8.73 (2H, m).

Example 71

3-((1-((1-methyl-1H-pyrazol-4-yl)sulfonyl)pyrrolidin-3-yl)oxy)-2,4'-bipyridine To a mixture of 3-(pyrrolidin-3-yloxy)-2,4'-bipyridine (85 mg), triethylamine (0.15 mL) and DMF (1.0 mL) was added 1-methyl-1H-pyrazole-4-sulfonyl chloride (0.051 mL) at 0° C. The mixture was stirred at room temperature for 1 hr. The mixture was diluted with saturated brine, and extracted with ethyl acetate. The organic layer was dried over magnesium sulfate, and the solvent was evaporated under reduced pressure. The residue was purified by silica gel column chromatography (NH, ethyl acetate), and the obtained solid was recrystallized from ethyl acetate/hexane to give the title compound (89 mg).

$^1$H NMR (300 MHz, DMSO-$d_6$) δ 1.96-2.19 (2H, m), 3.20 (1H, td, J=9.6, 7.0 Hz), 3.31-3.40 (2H, m), 3.55 (1H, dd, J=11.9, 4.7 Hz), 3.74 (3H, s), 5.12 (1H, t, J=4.6 Hz), 7.44 (1H, dd, J=8.3, 4.5 Hz), 7.59 (1H, dd, J=8.5, 1.1 Hz), 7.68-7.78 (3H, m), 8.28-8.36 (2H, m), 8.55-8.64 (2H, m).

Example 84

4-(4-fluoro-2-((1-((1-methyl-1H-pyrazol-4-yl)sulfonyl)pyrrolidin-3-yl)oxy)phenyl)pyrimidine

A) 1-(2-((1-benzylpyrrolidin-3-yl)oxy)-4-fluorophenyl)ethanone

A mixture of 1-benzylpyrrolidin-3-ol (4.1 g), 1-(4-fluoro-2-hydroxyphenyl)ethanone (3.0 g), triphenylphosphine (7.7 g), diisopropyl azodicarboxylate (40% toluene solution) (15 mL) and THF (50 mL) was stirred at room temperature for 3 hr. The mixture was concentrated under reduced pressure. The residue was purified by silica gel column chromatography (ethyl acetate/hexane) to give the title compound (3.7 g).

$^1$H NMR (300 MHz, CDCl$_3$) δ 1.95-2.10 (1H, m), 2.26-2.43 (1H, m), 2.56-2.68 (4H, m), 2.72-2.83 (2H, m), 3.01 (1H, dd, J=10.5, 6.0 Hz), 3.60-3.74 (2H, m), 4.83-4.94 (1H, m), 6.52 (1H, dd, J=10.9, 2.3 Hz), 6.62-6.72 (1H, m), 7.28-7.37 (5H, m), 7.81 (1H, dd, J=8.7, 6.8 Hz).

B) 4-(2-((1-benzylpyrrolidin-3-yl)oxy)-4-fluorophenyl) pyrimidine

A mixture of 1-(2-((1-benzylpyrrolidin-3-yl)oxy)-4-fluorophenyl)ethanone (3.6 g), N,N-dimethylformamide dimethyl acetal (20 mL) and acetonitrile (20 mL) was stirred overnight at 90° C. The mixture was concentrated under reduced pressure. A mixture of the residue, n-butyl alcohol (20 mL), DIPEA (20 mL) and formamidine acetate (7.2 g) was stirred overnight at 110° C. The mixture was concentrated under reduced pressure, and the residue was diluted with ethyl acetate. The organic layer was washed with 1M aqueous sodium hydroxide solution and saturated brine, and dried over sodium sulfate, and the solvent was evaporated under reduced pressure. The residue was purified by silica gel column chromatography (ethyl acetate/hexane) to give the title compound (2.1 g).

$^1$H NMR (300 MHz, CDCl$_3$) δ 1.94-2.06 (1H, m), 2.29-2.44 (1H, m), 2.61 (1H, td, J=8.4, 5.8 Hz), 2.77-2.88 (2H, m), 2.92-3.00 (1H, m), 3.58-3.78 (2H, m), 4.90 (1H, ddt, J=7.6, 5.4, 2.7 Hz), 6.60 (1H, dd, J=10.7, 2.4 Hz), 6.75-6.85 (1H, m), 7.27-7.37 (5H, m), 7.99-8.13 (2H, m), 8.69 (1H, d, J=5.7 Hz), 9.25 (1H, s).

C) 4-(4-fluoro-2-(pyrrolidin-3-yloxy)phenyl)pyrimidine

A mixture of 4-(2-((1-benzylpyrrolidin-3-yl)oxy)-4-fluorophenyl)pyrimidine (2.1 g), ammonium formate (1.9 g), 10% palladium on carbon (0.63 g) and methanol (20 mL) was heated with reflux for 1 hr. The insoluble substance was removed by filtration, and the filtrate was concentrated under reduced pressure. The residue was purified by silica gel column chromatography (NH, ethyl acetate/hexane) to give the title compound (0.91 g).

$^1$H NMR (300 MHz, DMSO-$d_6$) δ 1.73-1.88 (1H, m), 1.96-2.14 (1H, m), 2.45 (1H, brs), 2.71-2.84 (1H, m), 2.85-2.98 (2H, m), 3.01-3.15 (1H, m), 4.95-5.13 (1H, m), 6.86-6.98 (1H, m), 7.09 (1H, dd, J=11.5, 2.5 Hz), 7.99-8.11 (2H, m), 8.79 (1H, d, J=5.3 Hz), 9.22 (1H, d, J=1.3 Hz).

D) 4-(4-fluoro-2-((1-((1-methyl-1H-pyrazol-4-yl)sulfonyl)pyrrolidin-3-yl)oxy)phenyl)pyrimidine To a mixture of 4-(4-fluoro-2-(pyrrolidin-3-yloxy)phenyl) pyrimidine (100 mg), triethylamine (0.16 mL) and DMF (2.0 mL) was added 1-methyl-1H-pyrazole-4-sulfonyl chloride (77 mg) at 0° C., and the mixture was stirred at room temperature for 3 hr. The mixture was diluted with water, and extracted with ethyl acetate. The organic layer was washed with saturated brine, and dried over magnesium sulfate, and the solvent was evaporated under reduced pressure. The residue was recrystallized from ethyl acetate/hexane to give the title compound (130 mg).

$^1$H NMR (300 MHz, DMSO-$d_6$) δ 2.03-2.22 (2H, m), 3.12-3.26 (1H, m), 3.32-3.40 (2H, m), 3.55 (1H, dd, J=12.1, 4.5 Hz), 3.72 (3H, s), 5.14 (1H, brs), 6.91-7.03 (1H, m), 7.10 (1H, dd, J=11.5, 2.5 Hz), 7.61-7.76 (2H, m), 8.06 (1H, dd, J=8.8, 7.1 Hz), 8.28 (1H, s), 8.73 (1H, d, J=5.7 Hz), 9.22 (1H, d, J=1.1 Hz).

Example 85

3-((1-(morpholin-4-ylsulfonyl)pyrrolidin-3-yl)oxy)-2,4'-bipyridine

To a mixture of 3-(pyrrolidin-3-yloxy)-2,4'-bipyridine (100 mg), triethylamine (0.17 mL) and DMF (2.0 mL) was added morpholine-4-sulfonyl chloride (120 mg) at 0° C., and the mixture was stirred at room temperature for 2 hr. The mixture was diluted with saturated brine, and extracted with ethyl acetate. The organic layer was dried over magnesium sulfate, and the solvent was evaporated under reduced pressure. The residue was purified by silica gel column chromatography (NH, ethyl acetate/hexane), and the obtained solid was recrystallized from ethyl acetate/hexane to give the title compound (60 mg).

$^1$H NMR (300 MHz, DMSO-$d_6$) b 2.08-2.20 (1H, m), 2.22-2.36 (1H, m), 2.95-3.08 (4H, m), 3.33-3.57 (7H, m), 3.58-3.69 (1H, m), 5.25 (1H, brs), 7.47 (1H, dd, J=8.5, 4.5 Hz), 7.70 (1H, dd, J=8.5, 1.1 Hz), 7.86-7.94 (2H, m), 8.35 (1H, dd, J=4.5, 1.1 Hz), 8.59-8.69 (2H, m).

Example 88

4-(2-((1-(ethylsulfonyl)pyrrolidin-3-yl)oxy)-4-fluorophenyl)pyridine

A) 1-benzyl-3-(2-bromo-5-fluorophenoxy)pyrrolidine

To a mixture of 1-benzylpyrrolidin-3-ol (4.3 g), 2-bromo-5-fluorophenol (3.8 g), triphenylphosphine (7.9 g) and THF (60 mL) was added diisopropyl azodicarboxylate (40% toluene solution) (16 mL), and the mixture was stirred overnight at room temperature. The mixture was concentrated, and the residue was suspended in IPE/hexane. The resulting solid was removed by filtration, and the filtrate was concentrated. The residue was purified by silica gel column chromatography (NH, ethyl acetate/hexane) to give the title compound (6.5 g).

$^1$H NMR (300 MHz, CDCl$_3$) δ 1.97-2.10 (1H, m), 2.22-2.38 (1H, m), 2.64-2.81 (3H, m), 3.06-3.16 (1H, m), 3.62-3.75 (2H, m), 4.73-4.85 (1H, m), 6.48-6.60 (2H, m), 7.21-7.38 (5H, m), 7.41-7.50 (1H, m).

B) 4-(2-((1-benzylpyrrolidin-3-yl)oxy)-4-fluorophenyl)pyridine

A mixture of 1-benzyl-3-(2-bromo-5-fluorophenoxy)pyrrolidine (2.1 g), Pd(PPh$_3$)$_4$ (0.69 g), pyridin-4-ylboronic acid (1.1 g), potassium carbonate (1.2 g), DME (12 mL) and water (3 mL) was irradiated with microwave at 130° C. for 1.5 hr. This reaction was performed in three batches. The combined reaction mixture was poured into water, and the mixture was extracted with ethyl acetate. The organic layer was washed with saturated brine, and dried over sodium sulfate, and the solvent was evaporated under reduced pressure. The residue was purified by silica gel column chromatography (NH, ethyl acetate/hexane) to give the title compound (5.0 g).

MS (API+): [M+1-1]$^+$349.1

C) 4-(4-fluoro-2-(pyrrolidin-3-yloxy)phenyl)pyridine

A mixture of 4-(2-((1-benzylpyrrolidin-3-yl)oxy)-4-fluorophenyl)pyridine (5.0 g), ammonium formate (4.5 g), 10% palladium on carbon (3.1 g) and methanol (50 mL) was heated with reflux for 2 hr. The mixture was filtered through Celite, and the filtrate was concentrated under reduced pressure. The residue was diluted with saturated brine, and extracted with ethyl acetate. The organic layer was dried over sodium sulfate, and the solvent was evaporated under reduced pressure. The residue was purified by silica gel column chromatography (NH, methanol/ethyl acetate) to give the title compound (2.5 g).

$^1$H NMR (300 MHz, CDCl$_3$) δ 1.85-1.99 (1H, m), 2.01-2.15 (1H, m), 2.84-2.96 (1H, m), 2.99-3.19 (3H, m), 4.77-4.87 (1H, m), 6.64-6.82 (2H, m), 7.30 (1H, dd, J=8.3, 6.8 Hz), 7.36-7.43 (2H, m), 8.56-8.66 (2H, m).

D) 4-(2-((1-(ethylsulfonyl)pyrrolidin-3-yl)oxy)-4-fluorophenyl)pyridine

To a mixture of 4-(4-fluoro-2-(pyrrolidin-3-yloxy)phenyl)pyridine (200 mg), triethylamine (0.24 mL) and THF (2.0 mL) was added ethanesulfonyl chloride (0.095 mL), and the mixture was stirred at room temperature for 2 hr. The mixture was diluted with ethyl acetate and saturated sodium hydrogencarbonate solution, and extracted with ethyl acetate. The organic layer was separated, washed with water and saturated brine, and dried over sodium sulfate, and the solvent was evaporated under reduced pressure. The residue was purified by silica gel column chromatography (NH, ethyl acetate/hexane), and the obtained solid was recrystallized from ethyl acetate to give the title compound (140 mg).

$^1$H NMR (300 MHz, CDCl$_3$) δ 1.21 (3H, t, J=7.3 Hz), 2.13-2.28 (2H, m), 2.75 (2H, q, J=7.3 Hz), 3.22-3.34 (1H, m), 3.50-3.62 (2H, m), 3.69 (1H, dd, J=11.7, 4.2 Hz), 4.92-4.99 (1H, m), 6.68 (1H, dd, J=10.4, 2.4 Hz), 6.83 (1H, td, J=8.5, 2.4 Hz), 7.32 (1H, dd, J=8.5, 6.6 Hz), 7.36-7.39 (2H, m), 8.61-8.65 (2H, m).

Example 110

2-((1-((4-fluorophenyl)sulfonyl)pyrrolidin-3-yl)oxy)-3-(pyridin-4-yl)pyrazine

A) tert-butyl 3-((3-chloropyrazin-2-yl)oxy)pyrrolidine-1-carboxylate

To a mixture of 1-Boc-3-hydroxypyrrolidine (2.3 mL) and DMF (40 ml) was added sodium hydride (0.69 g) at 0° C., and the mixture was stirred for 30 min. To the mixture was added 2,3-dichloropyrazine (2.0 g), and the mixture was stirred overnight at room temperature. The mixture was poured into water, and extracted with ethyl acetate. The organic layer was dried over magnesium sulfate, and the solvent was evaporated under reduced pressure. The residue was purified by silica gel column chromatography (ethyl acetate/hexane) to give the title compound (4.0 g).

$^1$H NMR (300 MHz, CDCl$_3$) δ 1.48 (9H, s), 2.22 (2H, brs), 3.46-3.77 (4H, m), 5.56 (1H, brs), 7.95 (1H, s), 8.00 (1H, brs).

B) tert-butyl 3-((3-(pyridin-4-yl)pyrazin-2-yl)oxy)pyrrolidine-1-carboxylate

A mixture of tert-butyl 3-((3-chloropyrazin-2-yl)oxy)pyrrolidine-1-carboxylate (4.0 g), pyridin-4-ylboronic acid (2.4 g), Pd(PPh$_3$)$_4$ (1.5 g), potassium carbonate (2.7 g), DME (48 mL) and water (12 mL) was stirred overnight at 80° C. The mixture was poured into water, and extracted with ethyl acetate. The organic layer was washed with saturated brine, and dried over sodium sulfate, and the solvent was evaporated under reduced pressure. The residue was purified by silica gel column chromatography (NH, ethyl acetate/hexane) to give the title compound (2.5 g).

$^1$H NMR (300 MHz, CDCl$_3$) δ 1.47 (9H, s), 2.17-2.32 (2H, m), 3.43-3.81 (4H, m), 5.65-5.76 (1H, m), 7.91-8.04 (2H, m), 8.14 (1H, brs), 8.34 (1H, brs), 8.67-8.81 (2H, m).

C) 2-(pyridin-4-yl)-3-(pyrrolidin-3-yloxy)pyrazine dihydrochloride

A mixture of tert-butyl 3-((3-(pyridin-4-yl)pyrazin-2-yl)oxy)pyrrolidine-1-carboxylate (2.5 g), methanol (10 mL) and 4N hydrogen chloride/ethyl acetate (20 mL) was stirred at room temperature for 2 hr. The mixture was concentrated under reduced pressure, and the residue was washed with ethyl acetate to give the title compound (2.1 g).

$^1$H NMR (300 MHz, DMSO-d$_6$) δ 2.24-2.36 (2H, m), 3.28-3.44 (2H, m), 3.49-3.61 (2H, m), 5.76-5.84 (1H, m), 8.50 (1H, d, J=2.3 Hz), 8.57 (1H, d, J=2.3 Hz), 8.67 (2H, d, J=6.8 Hz), 8.97 (2H, d, J=6.8 Hz), 9.78 (1H, brs), 10.20 (1H, brs).

D) 2-((1-((4-fluorophenyl)sulfonyl)pyrrolidin-3-yl)oxy)-3-(pyridin-4-yl)pyrazine To a mixture of 2-(pyridin-4-yl)-3-(pyrrolidin-3-yloxy)pyrazine dihydrochloride (150 mg), triethylamine (0.33 mL) and DMF (3.0 mL) was added 4-fluorobenzene-1-sulfonyl chloride (0.074 mL) at 0° C., and the mixture was stirred overnight at room temperature. The mixture was diluted with saturated brine, and extracted with ethyl acetate. The organic layer was dried over magnesium sulfate, and the solvent was evaporated under reduced pressure. The residue was purified by silica gel column chromatography (NH, ethyl acetate), and the obtained solid was recrystallized from ethyl acetate/hexane to give the title compound (140 mg).

$^1$H NMR (300 MHz, CDCl$_3$) δ 2.19-2.30 (2H, m), 3.35-3.47 (1H, m), 3.51-3.64 (2H, m), 3.68-3.77 (1H, m), 5.53-5.61 (1H, m), 6.94-7.05 (2H, m), 7.69-7.77 (2H, m), 7.77-7.83 (2H, m), 8.11 (1H, d, J=2.6 Hz), 8.33 (1H, d, J=2.6 Hz), 8.63-8.71 (2H, m).

Example 124

3-((1-(pyridin-2-ylmethyl)piperidin-4-yl)oxy)-2,4'-bipyridine

To a mixture of 3-(piperidin-4-yloxy)-2,4'-bipyridine (50 mg), picoline aldehyde (0.022 mL), acetic acid (0.011 mL) and acetonitrile (1.0 mL) was added sodium triacetoxyborohydride (83 mg) at room temperature, and the mixture was stirred at room temperature for 3 hr. To the mixture was added saturated sodium hydrogencarbonate, and the mixture was extracted with ethyl acetate. The organic layer was washed with saturated brine, and dried over magnesium sulfate, and the solvent was evaporated under reduced pressure. The residue was purified by silica gel column chromatography (NH, ethyl acetate/hexane and methanol/ethyl acetate), and the obtained solid was recrystallized from ethyl acetate/hexane to give the title compound (23 mg).

$^1$H NMR (300 MHz, CDCl$_3$) δ 1.79-1.95 (2H, m), 1.97-2.09 (2H, m), 2.32-2.46 (2H, m), 2.60-2.78 (2H, m), 3.65 (2H, s), 4.44 (1H, dt, J=7.3, 3.5 Hz), 7.13-7.20 (1H, m), 7.27-7.40 (3H, m), 7.60-7.70 (1H, m), 7.88-7.93 (2H, m), 8.33 (1H, dd, J=4.5, 1.5 Hz), 8.54-8.60 (1H, m), 8.64-8.71 (2H, m).

The compounds of Examples produced according to the above-mentioned methods or a method analogous thereto are shown in the following tables. MS in the tables means actual measured value.

TABLE 1-1

| Example No. | IUPAC Name | Structure | MS |
|---|---|---|---|
| 1 | 1-benzyl-4-(5-methyl-2-(pyridin-4-yl)benzoyl)piperazin-2-one | 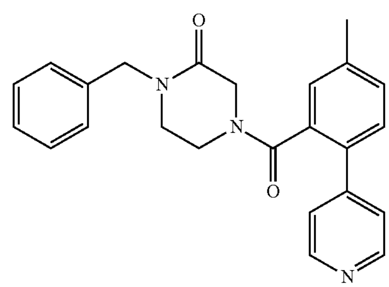 [SMILES: Cc1ccc(-c2ccncc2)c(C(=O)N2CCN(Cc3ccccc3)C(=O)C2)c1] | 386.2 |
| 2 | 4-(2-((1-benzylpiperidin-4-yl)oxy)-4-methylphenyl)pyridine | 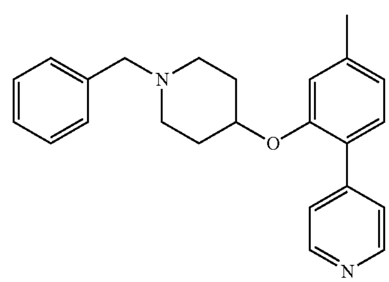 [SMILES: Cc1ccc(-c2ccncc2)c(OC2CCN(Cc3ccccc3)CC2)c1] | 359.2 |
| 3 | (4-(4-methoxybenzyl)piperazin-1-yl)(5-methyl-2-(pyridin-4-yl)phenyl)methanone | 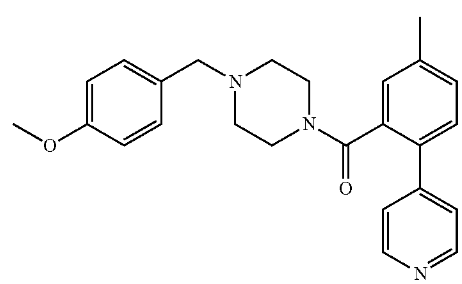 [SMILES: COc1ccc(CN2CCN(C(=O)c3cc(C)ccc3-c3ccncc3)CC2)cc1] | 402.2 |

TABLE 1-1-continued

| Example No. | IUPAC Name | Structure | MS |
|---|---|---|---|
| 4 | 3-((1-benzylpiperidin-4-yl)oxy)-2,4'-bipyridine | 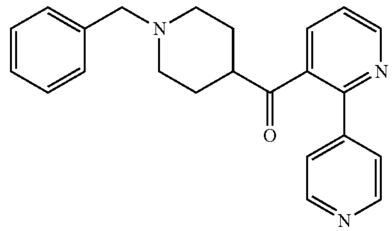 [SMILES: O=C(c1cccnc1-c1ccncc1)C1CCN(Cc2ccccc2)CC1] | 346.2 |
| 5 | 4-(2-((1-benzylpiperidin-4-yl)oxy)-5-fluorophenyl)pyridine | 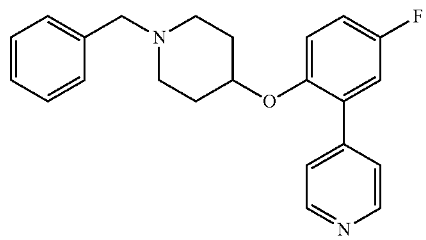 [SMILES: Fc1ccc(OC2CCN(Cc3ccccc3)CC2)c(-c2ccncc2)c1] | 363.2 |
| 6 | 4-((1-benzylpiperidin-4-yl)oxy)-5-(pyridin-4-yl)pyrimidine | 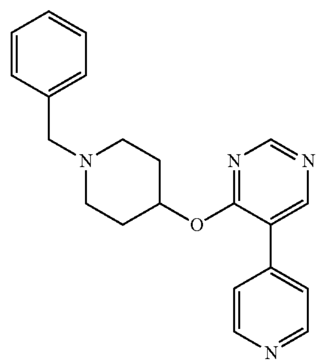 [SMILES: c1ccc(CN2CCC(Oc3ncncc3-c3ccncc3)CC2)cc1] | 347.2 |
| 7 | 4-(2-((1-benzylpiperidin-4-yl)oxy)-4-fluorophenyl)pyridine | 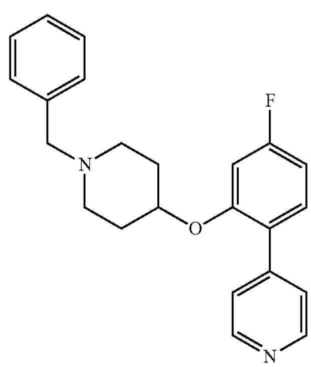 [SMILES: Fc1ccc(-c2ccncc2)c(OC2CCN(Cc3ccccc3)CC2)c1] | 363.2 |
| 8 | 4-(2-((1-benzylpiperidin-4-yl)oxy)phenyl)pyridine | 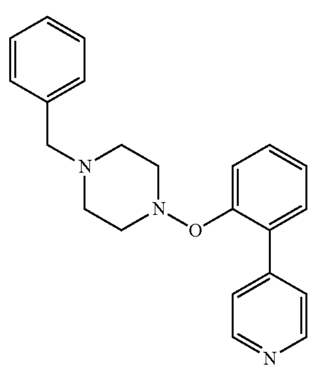 [SMILES: c1ccc(CN2CCN(Oc3ccccc3-c3ccncc3)CC2)cc1] | 345.2 |

TABLE 1-1-continued

| Example No. | IUPAC Name | Structure | MS |
|---|---|---|---|
| 9 | tert-butyl 4-(2-(pyridin-4-yl)phenoxy)piperidine-1-carboxylate | 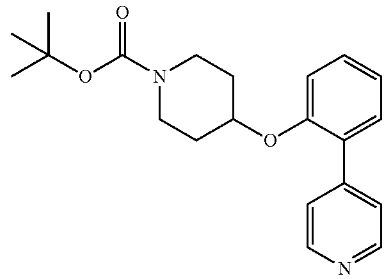 [SMILES: CC(C)(C)OC(=O)N1CCC(Oc2ccccc2-c2ccncc2)CC1] | 355.2 |
| 10 | 2-((4-(2-(pyridin-4-yl)phenoxy)piperidin-1-yl)methyl)pyridine | 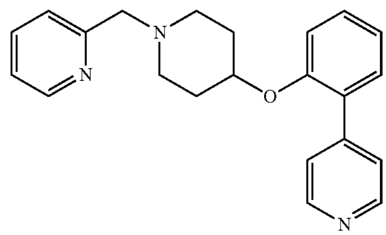 [SMILES: c1ccc(CN2CCC(Oc3ccccc3-c3ccncc3)CC2)nc1] | 346.2 |

TABLE 1-2

| Example No. | IUPAC Name | Structure | MS |
|---|---|---|---|
| 11 | phenyl(4-(2-(pyridin-4-yl)phenoxy)piperidin-1-yl)methanone | 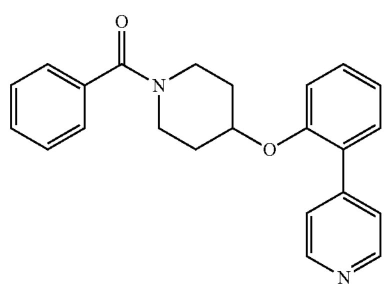 [SMILES: O=C(c1ccccc1)N1CCC(Oc2ccccc2-c2ccncc2)CC1] | 359.2 |
| 12 | 4-(2-((1-(cyclopropylmethyl)piperidin-4-yl)oxy)phenyl)pyridine | 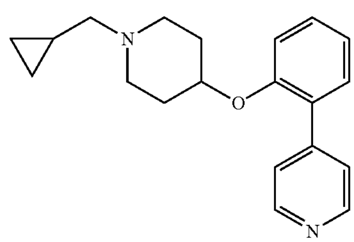 [SMILES: c1ccc(-c2ccncc2)c(OC2CCN(CC3CC3)CC2)c1] | 309.2 |
| 13 | 4-(2-((1-methylpiperidin-4-yl)oxy)phenyl)pyridine | 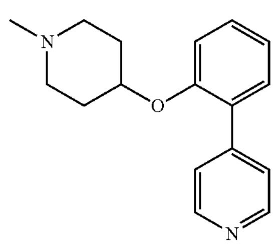 [SMILES: CN1CCC(Oc2ccccc2-c2ccncc2)CC1] | 269.1 |

TABLE 1-2-continued

| Example No. | IUPAC Name | Structure | MS |
|---|---|---|---|
| 14 | 4-(2-((1-ethylpiperidin-4-yl)oxy)phenyl)pyridine | 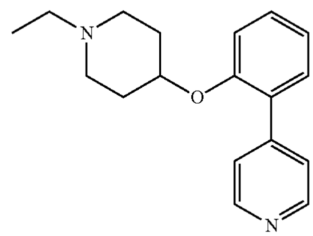 [SMILES: CCN1CCC(Oc2ccccc2-c2ccncc2)CC1] | 283.2 |
| 15 | 4-(2-((1-benzylpiperidin-4-yl)oxy)phenyl)pyrimidine | 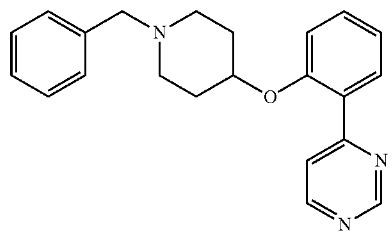 [SMILES: c1ccc(CN2CCC(Oc3ccccc3-c3ccncn3)CC2)cc1] | 346.2 |
| 16 | 4-(2-((1-((1-methyl-1H-imidazol-2-yl)methyl)piperidin-4-yl)oxy)phenyl)pyridine | 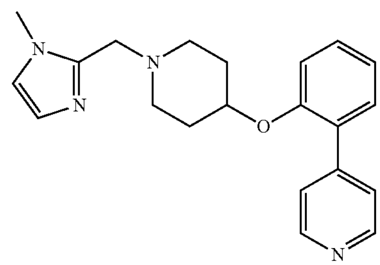 [SMILES: Cn1ccnc1CN1CCC(Oc2ccccc2-c2ccncc2)CC1] | 349.2 |
| 17 | 4-(2-((1-(1,3-oxazol-4-ylmethyl)piperidin-4-yl)oxy)phenyl)pyridine | 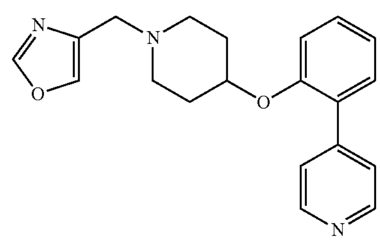 [SMILES: c1ccc(-c2ccncc2)c(OC2CCN(Cc3cocn3)CC2)c1] | 336.2 |
| 18 | 3-((4-(2(pyridin-4-yl)phenoxy)piperidin-1-yl)methyl)pyridine | 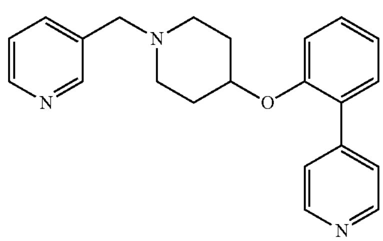 [SMILES: c1cncc(CN2CCC(Oc3ccccc3-c3ccncc3)CC2)c1] | 346.2 |
| 19 | 4-(2-((1-((1-methyl-1H-pyrazol-4-yl)methyl)piperidin-4-yl)oxy)phenyl)pyridine | 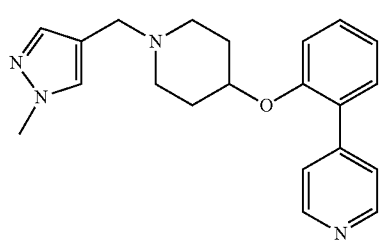 [SMILES: Cn1cc(CN2CCC(Oc3ccccc3-c3ccncc3)CC2)cn1] | 349.2 |

TABLE 1-2-continued

| Example No. | IUPAC Name | Structure | MS |
|---|---|---|---|
| 20 | N,N-dimethyl-2-(4-(2-(pyridin-4-yl)phenoxy)piperidin-1-yl)acetamide | 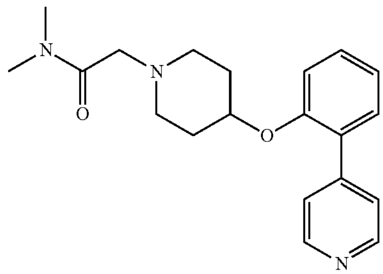 [SMILES: CN(C)C(=O)CN1CCC(Oc2ccccc2-c2ccncc2)CC1] | 340.2 |

TABLE 1-3

| Example No. | IUPAC Name | Structure | MS |
|---|---|---|---|
| 21 | 2-(4-(2,4'-bipyridin-3-yloxy)piperidin-1-yl)-N,N-dimethylacetamide | 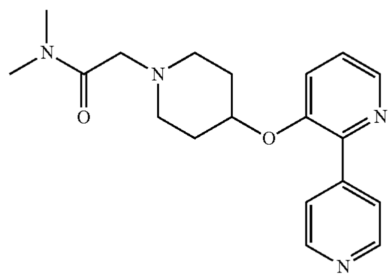 [SMILES: CN(C)C(=O)CN1CCC(Oc2cccnc2-c2ccncc2)CC1] | 341.2 |
| 22 | 3-((1-((1-methyl-1H-pyrazol-4-yl)methyl)piperidin-4-yl)oxy)-2,4'-bipyridine | 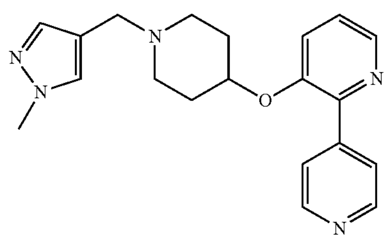 [SMILES: Cn1cc(CN2CCC(Oc3cccnc3-c3ccncc3)CC2)cn1] | 350.2 |
| 23 | (4-(4-methoxybenzyl)piperazin-1-yl)(2-(pyrimidin-4-yl)phenyl)methanone | 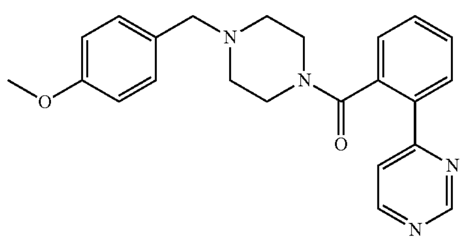 [SMILES: COc1ccc(CN2CCN(C(=O)c3ccccc3-c3ccncn3)CC2)cc1] | 389.2 |
| 24 | 4-(5-fluoro-2-((1-((1-methyl-1H-pyrazol-4-yl)methyl)piperidin-4-yl)oxy)phenyl)pyrimidine | 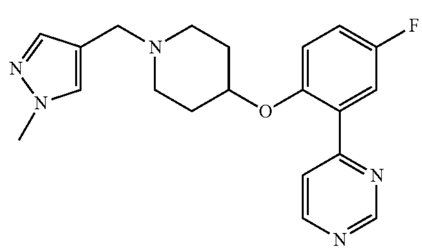 [SMILES: Cn1cc(CN2CCC(Oc3ccc(F)cc3-c3ccncn3)CC2)cn1] | 368.2 |

TABLE 1-3-continued

| Example No. | IUPAC Name | Structure | MS |
|---|---|---|---|
| 25 | 4-(4-chloro-2-((1-((1-methyl-1H-pyrazol-4-yl)methyl)piperidin-4-yl)oxy)phenyl)pyrimidine | 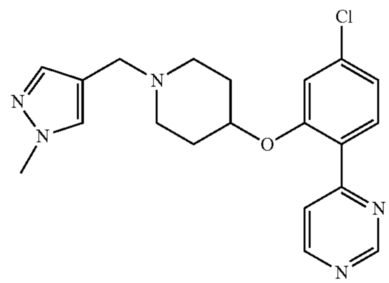 [SMILES: Cn1cc(CN2CCC(Oc3cc(Cl)ccc3-c3ccncn3)CC2)cn1] | 384.1 |
| 26 | 2-(4-(5-chloro-2-(pyrimidin-4-yl)phenoxy)piperidin-1-yl)-N,N-dimethylacetamide | 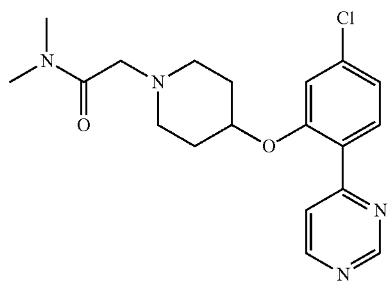 [SMILES: CN(C)C(=O)CN1CCC(Oc2cc(Cl)ccc2-c2ccncn2)CC1] | 375.2 |
| 27 | 4-(3-((1-benzylpiperidin-4-yl)oxy)pyridin-2-yl)pyrimdine | 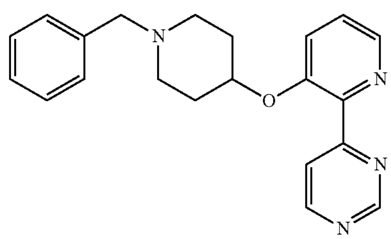 [SMILES: c1ccc(CN2CCC(Oc3cccnc3-c3ccncn3)CC2)cc1] | 347.2 |
| 28 | 2-(4-(4-fluoro-2-(pyrimidin-4-yl)phenoxy)piperidin-1-yl)-N,N-dimethylacetamide | 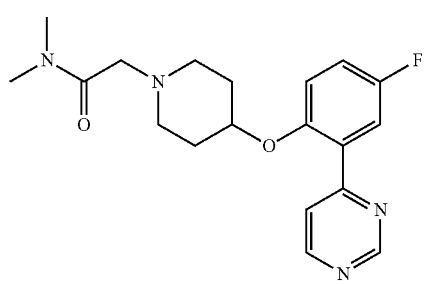 [SMILES: CN(C)C(=O)CN1CCC(Oc2ccc(F)cc2-c2ccncn2)CC1] | 359.2 |
| 29 | 1-((4-fluoro-2-(pyridin-4-yl)phenyl)sulfonyl)-4-(4-methoxybenzyl)piperazine | 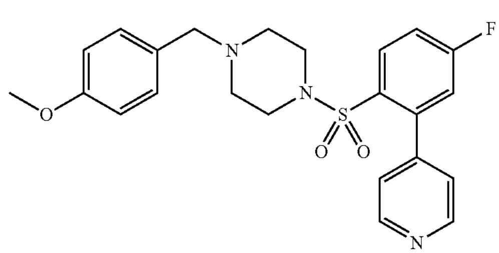 [SMILES: COc1ccc(CN2CCN(S(=O)(=O)c3ccc(F)cc3-c3ccncc3)CC2)cc1] | 442.1 |

TABLE 1-3-continued

| Example No. | IUPAC Name | Structure | MS |
|---|---|---|---|
| 30 | (5-fluoro-2-(pyrimidin-4-yl)phenyl)(4-(4-methoxybenzyl)piperazin-1-yl)methanone | 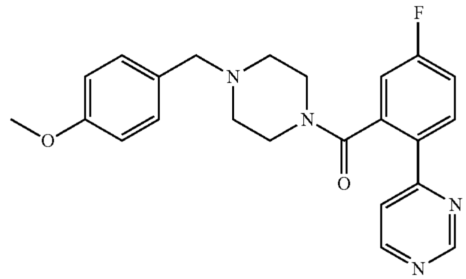 [SMILES: COc1ccc(CN2CCN(C(=O)c3cc(F)ccc3-c3ccncn3)CC2)cc1] | 407.2 |

TABLE 1-4

| Example No. | IUPAC Name | Structure | MS |
|---|---|---|---|
| 31 | N,N-dimethyl-2-(4-(2-(pyrimidin-4-yl)phenoxy)piperidin-1-yl)acetamide | 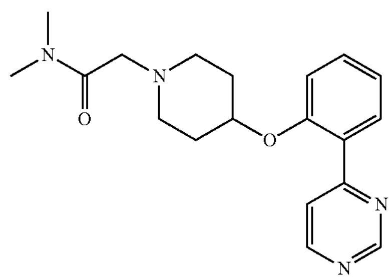 [SMILES: CN(C)C(=O)CN1CCC(Oc2ccccc2-c2ccncn2)CC1] | 341.2 |
| 32 | 2-(4-(5-fluoro-2-(pyrimidin-4-yl)phenoxy)piperidin-1-yl)-N,N-dimethylacetamide | 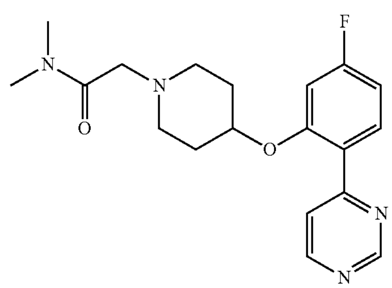 | 359.2 |
| 33 | 4-(2-((1-((1-methyl-1H-pyrazol-4-yl)methyl)piperidin-4-yl)oxy)phenyl)pyrimidine | 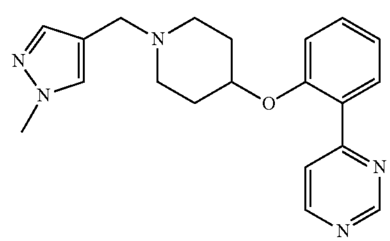 [SMILES: Cn1cc(CN2CCC(Oc3ccccc3-c3ccncn3)CC2)cn1] | 350.2 |
| 34 | 4-(2-((1-benzyl-3,3-difluoropiperidin-4-yl)oxy)phenyl)pyrimidine | 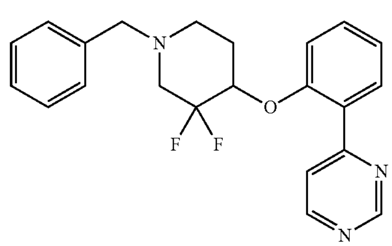 [SMILES: FC1(F)CN(Cc2ccccc2)CCC1Oc1ccccc1-c1ccncn1] | 382.1 |

TABLE 1-4-continued

| Example No. | IUPAC Name | Structure | MS |
|---|---|---|---|
| 35 | 2-((1-(((1-methyl-1H-pyrazol-4-yl)methyl)piperidin-4-yl)oxy)-3,4'-bipyridine | 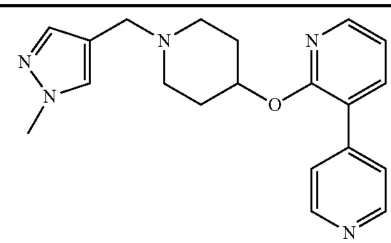 | 350.2 |
| 36 | 3-((1-(tetrahydrofuran-3-ylmethyl)piperidin-4-yl)oxy)-2,4'-bipyridine | 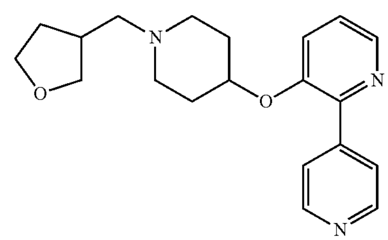 [SMILES: c1cnc(-c2ccncc2)c(OC2CCN(CC3CCOC3)CC2)c1] | 340.2 |
| 37 | 2-(4-(2,4'-bipyridin-3-yloxy)piperidin-1-yl)-1-(pyrrolidin-1-yl)ethanone | 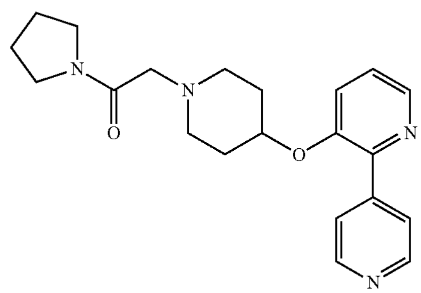 [SMILES: O=C(CN1CCC(Oc2cccnc2-c2ccncc2)CC1)N1CCCC1] | 367.2 |
| 38 | 2-(4-(2,4'-bipyridin-3-yloxy)piperidin-1-yl)-1-(morpholin-4-yl)ethanone | 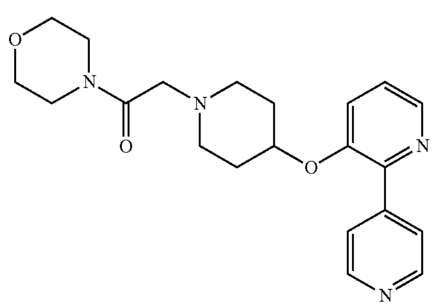 [SMILES: O=C(CN1CCC(Oc2cccnc2-c2ccncc2)CC1)N1CCOCC1] | 383.2 |
| 39 | 1-(azetidin-1-yl)-2-(4-(2,4'-bipyridin-3-yloxy)piperidin-1-yl)ethanone | 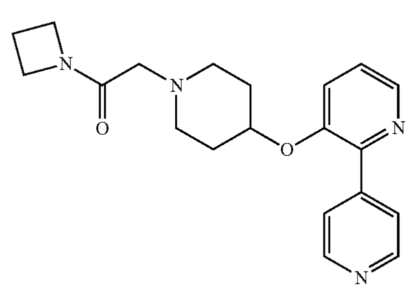 [SMILES: O=C(CN1CCC(Oc2cccnc2-c2ccncc2)CC1)N1CCC1] | 353.2 |

TABLE 1-4-continued

| Example No. | IUPAC Name | Structure | MS |
|---|---|---|---|
| 40 | 2-((1-((1-methyl-1H-pyrazol-4-yl)methyl)piperidin-4-yl)oxy)-3-(pyridin-4-yl)pyrazine | 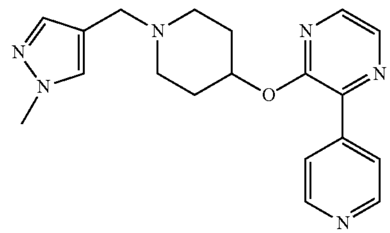 [SMILES: Cn1cc(CN2CCC(Oc3nccnc3-c3ccncc3)CC2)cn1] | 351.1 |

TABLE 1-5

| Example No. | IUPAC Name | Structure | MS |
|---|---|---|---|
| 41 | 3-((1-((3-methyl-1,2-oxazol-5-yl)methyl)piperidin-4-yl)oxy)-2,4'-bipyridine | 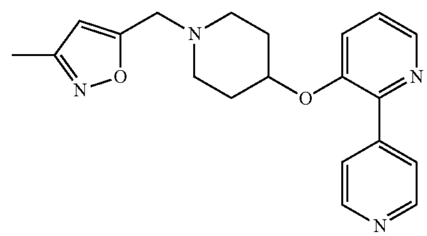 [SMILES: Cc1cc(CN2CCC(Oc3cccnc3-c3ccncc3)CC2)on1] | 351.1 |
| 42 | 3-((1-((5-methyl-1,2-oxazol-3-yl)methyl)piperidin-4-yl)oxy)-2,4'-bipyridine | 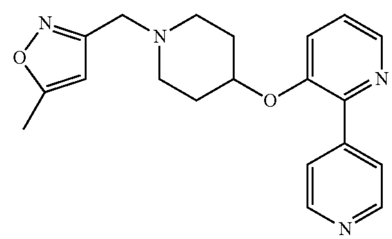 [SMILES: Cc1cc(CN2CCC(Oc3cccnc3-c3ccncc3)CC2)no1] | 351.1 |
| 43 | 4-((4-(2,4'-bipyridin-3-yloxy)piperidin-1-yl)methyl)benzonitrile | 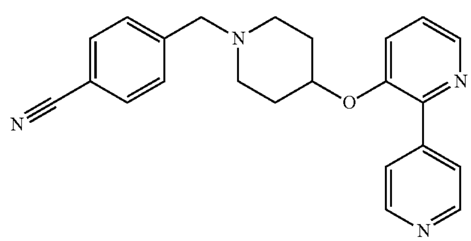 [SMILES: N#Cc1ccc(CN2CCC(Oc3cccnc3-c3ccncc3)CC2)cc1] | 371.2 |
| 44 | 3-((1-(pyrimidin-5-ylmethyl)piperidin-4-yl)oxy)-2,4'-bipyridine | 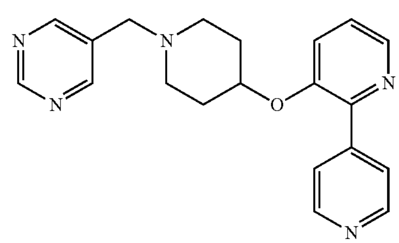 [SMILES: c1cnc(-c2ccncc2)c(OC2CCN(Cc3cncnc3)CC2)c1] | 348.2 |

TABLE 1-5-continued

| Example No. | IUPAC Name | Structure | MS |
|---|---|---|---|
| 45 | 3-((1-(pyrazin-2-ylmethyl)piperidin-4-yl)oxy)-2,4'-bipyridine | 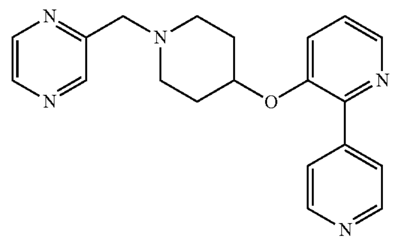 [SMILES: c1cnc(-c2ccncc2)c(OC2CCN(Cc3cnccn3)CC2)c1] | 348.2 |
| 46 | 3-((1-(pyrimidin-2-ylmethyl)piperidin-4-yl)oxy)-2,4'-bipyridine | 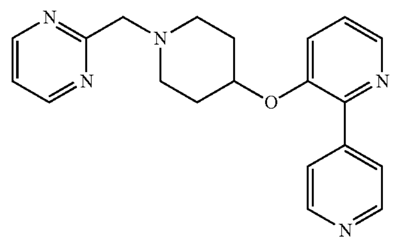 [SMILES: c1cnc(CN2CCC(Oc3cccnc3-c3ccncc3)CC2)nc1] | 348.2 |
| 47 | 3-((1-(1,3-thiazol-4-ylmethyl)piperidin-4-yl)oxy)-2,4'-bipyridine | 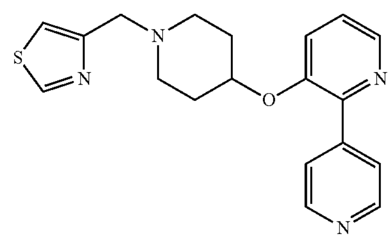 [SMILES: c1cnc(-c2ccncc2)c(OC2CCN(Cc3cscn3)CC2)c1] | 353.1 |
| 48 | 3-((1-((2-methyl-1,3-oxazol-5-yl)methyl)piperidin-4-yl)oxy)-2,4'-bipyridine | 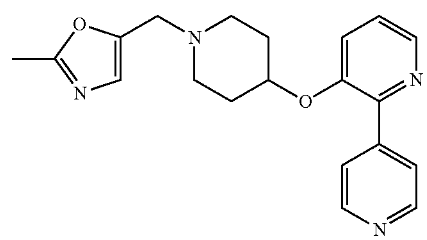 [SMILES: Cc1ncc(CN2CCC(Oc3cccnc3-c3ccncc3)CC2)o1] | 351.2 |
| 49 | 2-(4-(2,4'-bipyridin-3-yloxy)piperidin-1-yl)-N,N-diethylacetamide | 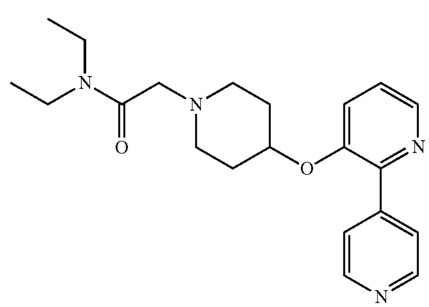 [SMILES: CCN(CC)C(=O)CN1CCC(Oc2cccnc2-c2ccncc2)CC1] | 369.1 |
| 50 | 3-((1-(4-fluorobenzyl)piperidin-4-yl)oxy)-2,4'-bipyridine | 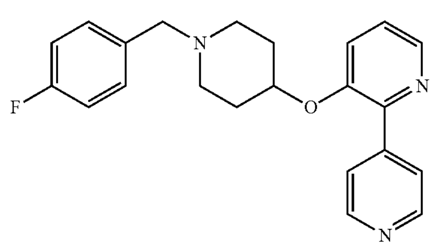 [SMILES: Fc1ccc(CN2CCC(Oc3cccnc3-c3ccncc3)CC2)cc1] | 364.2 |

TABLE 1-6

| Example No. | IUPAC Name | Structure | MS |
|---|---|---|---|
| 51 | 1-(2,4'-bipyridin-3-ylmethyl)-4-((1-methyl-1H-pyrazol-4-yl)methyl)piperazin-2-one | 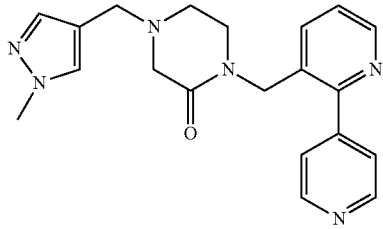 [SMILES: Cn1cc(CN2CCN(Cc3cccnc3-c3ccncc3)C(=O)C2)cn1] | 363.2 |
| 52 | 2-((3,3-difluoro-1-((1-methyl-1H-pyrazol-4-yl)methyl)piperidin-4-yl)oxy)-3,4'-bipyridine | 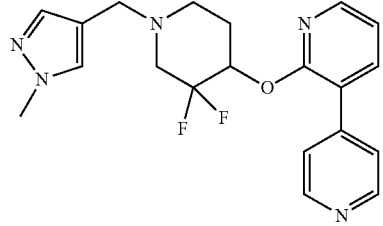 [SMILES: Cn1cc(CN2CCC(Oc3ncccc3-c3ccncc3)C(F)(F)C2)cn1] | 386.1 |
| 53 | 2-((3,3-difluoro-1-((1-methyl-1H-pyrazol-4-yl)methyl)piperidin-4-yl)oxy)-3-(pyridin-4-yl)pyrazine | 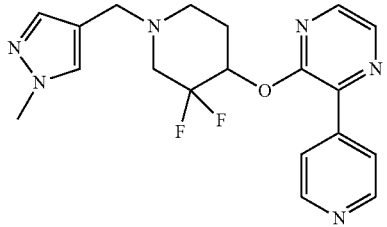 [SMILES: Cn1cc(CN2CCC(Oc3nccnc3-c3ccncc3)C(F)(F)C2)cn1] | 387.1 |
| 54 | 2-(3,3-difluoro-4-((3-(pyridin-4-yl)pyrazin-2-yl)oxy)piperidin-1-yl)-N,N-dimethylacetamide | 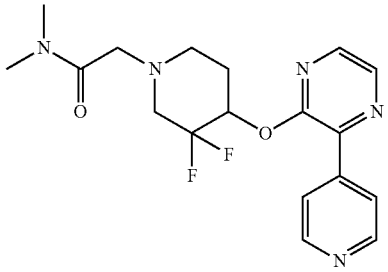 [SMILES: CN(C)C(=O)CN1CCC(Oc2nccnc2-c2ccncc2)C(F)(F)C1] | 378.1 |
| 55 | 1-(2,4'-bipyridin-3-ylmethyl)-4-(4-fluorobenzyl)piperazin-2-one | 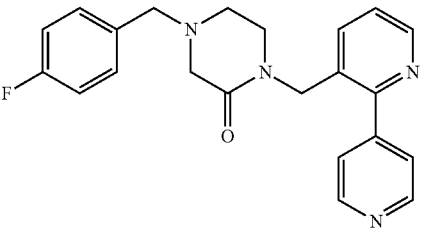 [SMILES: O=C1CN(Cc2ccc(F)cc2)CCN1Cc1cccnc1-c1ccncc1] | 377.1 |
| 56 | 2-((1-(pyrazin-2-ylmethyl)piperidin-4-yl)oxy)-3-(pyridin-4-yl)pyrazine | 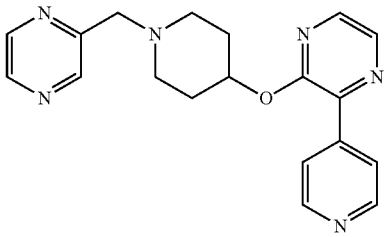 [SMILES: c1cc(-c2nccnc2OC2CCN(Cc3cnccn3)CC2)ccn1] | 349.2 |

TABLE 1-6-continued

| Example No. | IUPAC Name | Structure | MS |
|---|---|---|---|
| 57 | 4-(2-((1-(pyrazin-2-ylmethyl)piperidin-4-yl)oxy)phenyl)pyrimidine | 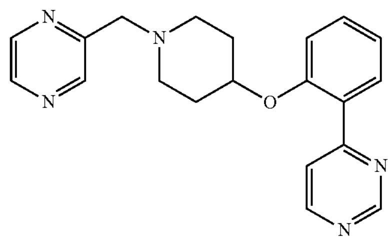 [SMILES: c1ccc(-c2ccncn2)c(OC2CCN(Cc3cnccn3)CC2)c1] | 348.2 |
| 58 | 1-(morpholin-4-yl)-2-(4-(2-(pyrimidin-4-yl)phenoxy)piperidin-1-yl)ethanone | 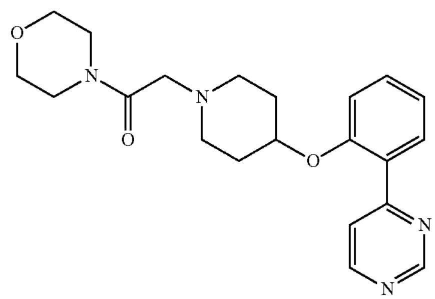 [SMILES: O=C(CN1CCC(Oc2ccccc2-c2ccncn2)CC1)N1CCOCC1] | 383.1 |
| 59 | 1-(morpholin-4-yl)-2-(4-((3-(pyridin-4-yl)pyrazin-2-yl)oxy)piperidin-1-yl)ethanone | 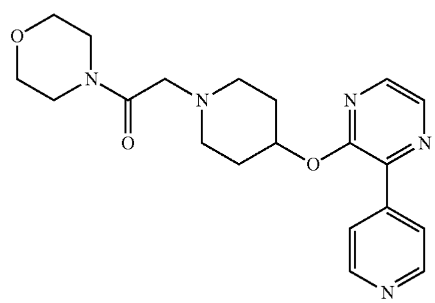 [SMILES: O=C(CN1CCC(Oc2nccnc2-c2ccncc2)CC1)N1CCOCC1] | 384.1 |
| 60 | 2-(4-(5-fluoro-2-(pyrimidin-4-yl)phenoxy)piperidin-1-yl)-1-(morpholin-4-yl)ethanone | 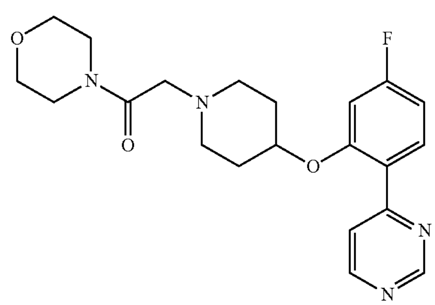 [SMILES: O=C(CN1CCC(Oc2cc(F)ccc2-c2ccncn2)CC1)N1CCOCC1] | 401.1 |

TABLE 1-7

| Example No. | IUPAC Name | Structure | MS |
|---|---|---|---|
| 61 | 3-((1-benzylpyrrolidin-3-yl)oxy)-2,4'-bipyridine | 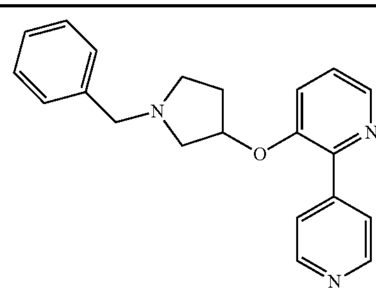 | 332.2 |

TABLE 1-7-continued
| Example No. | IUPAC Name | Structure | MS |
|---|---|---|---|
| 62 | 1-(3-(2,4'-bipyridin-3-yloxy)pyrrolidin-1-yl)-2-(4-methoxyphenyl)ethanone | 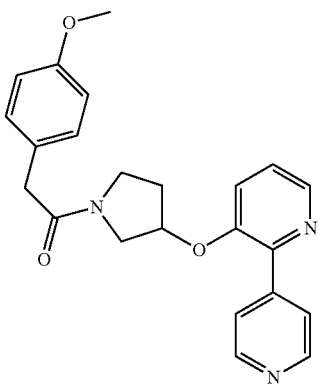 [SMILES: COc1ccc(CC(=O)N2CCC(Oc3cccnc3-c3ccncc3)C2)cc1] | 390.2 |
| 63 | 1-(4-(2,4'-bipyridin-3-yloxy)piperidin-1-yl)-2-(4-methoxyphenyl)ethanone | 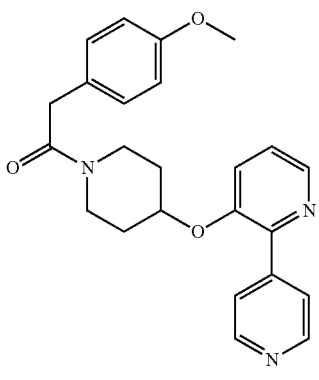 [SMILES: COc1ccc(CC(=O)N2CCC(Oc3cccnc3-c3ccncc3)CC2)cc1] | 404.2 |
| 64 | 3-((1-((4-methoxyphenyl)sulfonyl)pyrrolidin-3-yl)oxy)-2,4'-bipyridine | 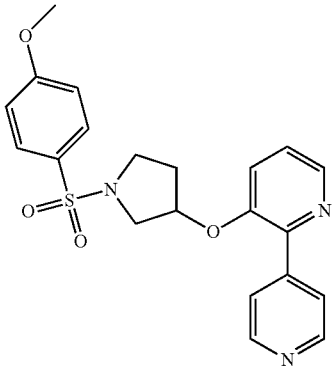 [SMILES: COc1ccc(S(=O)(=O)N2CCC(Oc3cccnc3-c3ccncc3)C2)cc1] | 412.1 |
| 65 | 3-((1-((4-methoxyphenyl)sulfonyl)piperidin-4-yl)oxy)-2,4'-bipyridine | 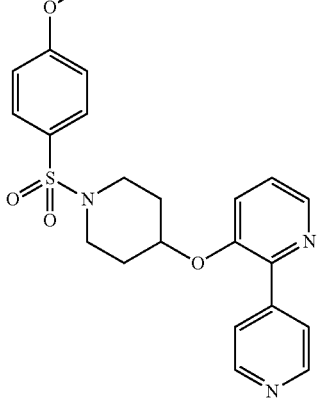 | 426.1 |

TABLE 1-7-continued
| Example No. | IUPAC Name | Structure | MS |
|---|---|---|---|
| 66 | (3-(2,4'-bipyridin-3-yloxy)pyrrolidin-1-yl)(cyclopropyl)methanone | 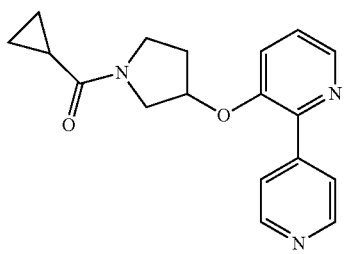 [SMILES: O=C(C1CC1)N1CCC(Oc2cccnc2-c2ccncc2)C1] | 310.2 |
| 67 | (4-(2,4'-bipyridin-3-yloxy)piperidin-1-yl)(cyclopropyl)methanone | 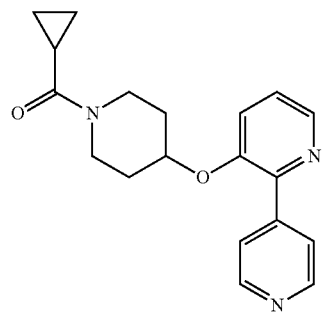 [SMILES: O=C(C1CC1)N1CCC(Oc2cccnc2-c2ccncc2)CC1] | 324.2 |
| 68 | 3-((1-(cyclopropylsulfonyl)pyrrolidin-3-yl)oxy)-2,4'-bipyridine | 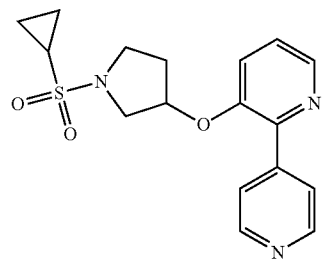 | 346.1 |
| 69 | 3-((1-(ethylsulfonyl)pyrrolidin-3-yl)oxy)-2,4'-bipyridine | 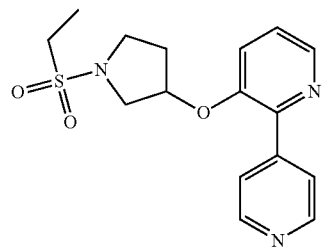 [SMILES: CCS(=O)(=O)N1CCC(Oc2cccnc2-c2ccncc2)C1] | 334.1 |
| 70 | 3-((1-((trifluoromethyl)sulfonyl)pyrrolidin-3-yl)oxy)-2,4'-bipyridine | 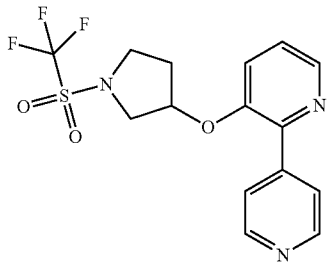 [SMILES: O=S(=O)(N1CCC(Oc2cccnc2-c2ccncc2)C1)C(F)(F)F] | 374.0 |

TABLE 1-8

| Example No. | IUPAC Name | Structure | MS |
|---|---|---|---|
| 71 | 3-((1-((1-methyl-1H-pyrazol-4-yl)sulfonyl)pyrrolidin-3-yl)oxy)-2,4'-bipyridine | 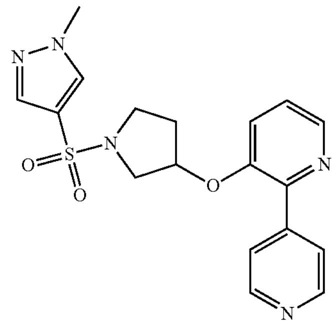 [SMILES: Cn1cc(S(=O)(=O)N2CCC(Oc3cccnc3-c3ccncc3)C2)cn1] | 386.0 |
| 72 | 1-(4-(2,4'-bipyridin-3-yloxy)piperidin-1-yl)-2-cyclopropylethanone | 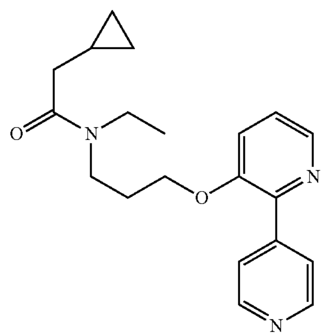 [SMILES: CCN(CCCOc1cccnc1-c1ccncc1)C(=O)CC1CC1] | 338.2 |
| 73 | 3-((1-((4-fluorophenyl)sulfonyl)pyrrolidin-3-yl)oxy)-2,4'-bipyridine | 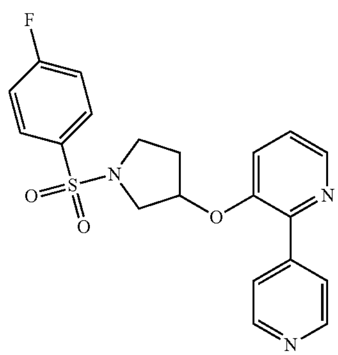 [SMILES: O=S(=O)(c1ccc(F)cc1)N1CCC(Oc2cccnc2-c2ccncc2)C1] | 400.0 |
| 74 | 2-(4-methoxyphenyl)-1-(4-(2-(pyrimidin-4-yl)phenoxy)piperidin-1-yl)ethanone | 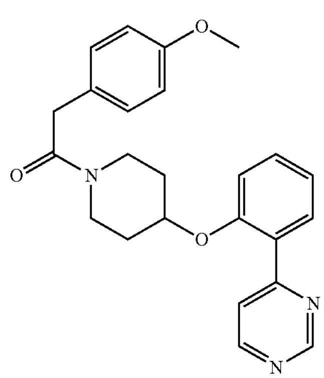 [SMILES: COc1ccc(CC(=O)N2CCC(Oc3ccccc3-c3ccncn3)CC2)cc1] | 404.2 |

TABLE 1-8-continued
| Example No. | IUPAC Name | Structure | MS |
|---|---|---|---|
| 75 | cyclopropyl(4-(2-(pyrimidin-4-yl)phenoxy)piperidin-1-yl)methanone | 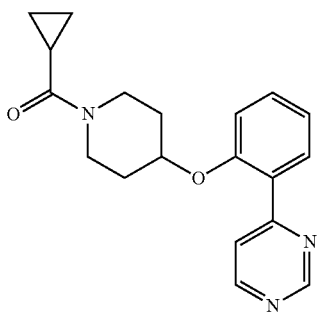 [SMILES: O=C(C1CC1)N1CCC(Oc2ccccc2-c2ccncn2)CC1] | 324.2 |
| 76 | 2-cyclopropyl-1-(4-(2-(pyrimidin-4-yl)phenoxy)piperidin-1-yl)ethanone | 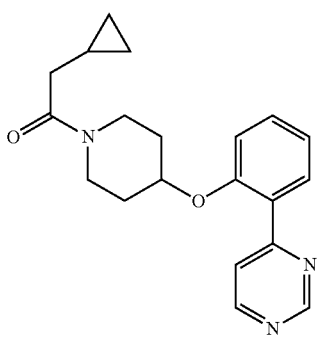 [SMILES: O=C(CC1CC1)N1CCC(Oc2ccccc2-c2ccncn2)CC1] | 338.1 |
| 77 | 4-(2-((1-benzylpyrrolidin-3-yl)oxy)-5-fluorophenyl)pyridine | 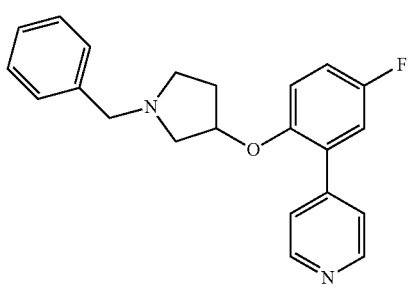 [SMILES: Fc1ccc(OC2CCN(Cc3ccccc3)C2)c(-c2ccncc2)c1] | 349,1 |
| 78 | 4-(2-((1-(cyclopropylsulfonyl)pyrrolidin-3-yl)oxy)-5-fluorophenyl)pyridine | 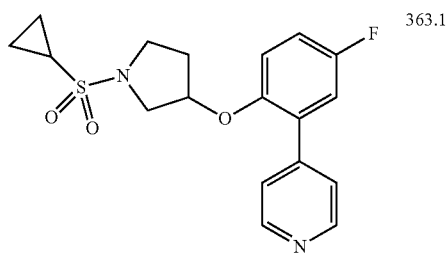 | 363.1 |
| 79 | 4-(2-((1-(ethylsulfonyl)pyrrolidin-3-yl)oxy)-5-fluorophenyl)pyridine | 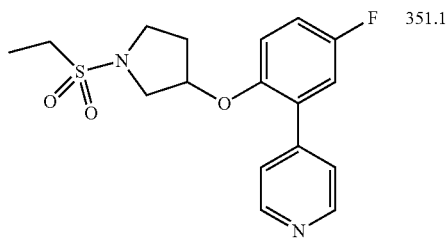 | 351.1 |

TABLE 1-8-continued

| Example No. | IUPAC Name | Structure | MS |
|---|---|---|---|
| 80 | 4-(5-fluoro-2-((1-((1-methyl-1H-pyrazol-4-yl)sulfonyl)pyrrolidin-3-yl)oxy)phenyl)pyridine | 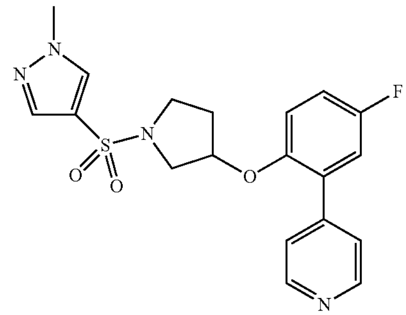 [SMILES: Cn1cc(S(=O)(=O)N2CCC(Oc3ccc(F)cc3-c3ccncc3)C2)cn1] | 403.1 |

TABLE 1-9

| Example No. | IUPAC Name | Structure | MS |
|---|---|---|---|
| 81 | 4-(2-((1-benzylpyrrolidin-3-yl)oxy)-4-fluorophenyl)pyrimidine | 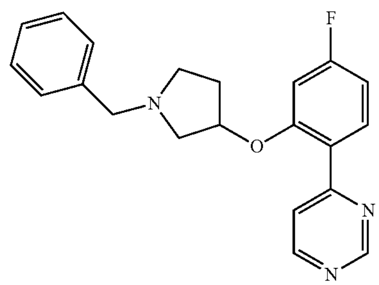 [SMILES: Fc1ccc(-c2ccncn2)c(OC2CCN(Cc3ccccc3)C2)c1] | 350.0 |
| 82 | 3-(2,4'-bipyridin-3-yloxy)-N,N-dimethylpyrrolidine-1-sulfonamide | 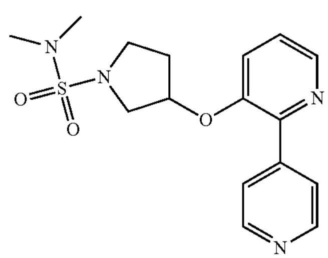 [SMILES: CN(C)S(=O)(=O)N1CCC(Oc2cccnc2-c2ccncc2)C1] | 349.0 |
| 83 | 4-(2-((1-(cyclopropylsulfonyl)pyrrolidin-3-yl)oxy)-4-fluorophenyl)pyrimidine | 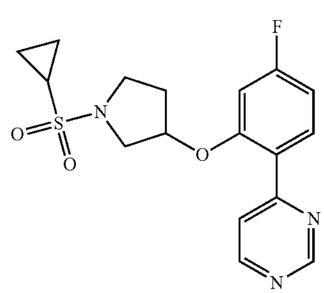 [SMILES: O=S(=O)(C1CC1)N1CCC(Oc2cc(F)ccc2-c2ccncn2)C1] | 364.0 |

TABLE 1-9-continued

| Example No. | IUPAC Name | Structure | MS |
|---|---|---|---|
| 84 | 4-(4-fluoro-2-((1-((1-methyl-1H-pyrazol-4-yl)sulfonyl)pyrrolidin-3-yl)oxy)phenyl)pyrimidine | 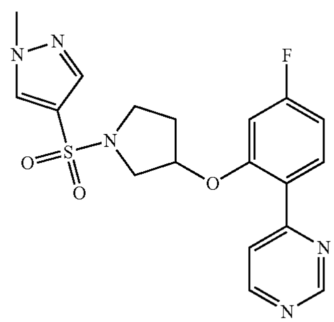 [SMILES: Cn1cc(S(=O)(=O)N2CCC(Oc3cc(F)ccc3-c3ccncn3)C2)cn1] | 404.0 |
| 85 | 3-((1-(morpholin-4-ylsulfonyl)pyrrolidin-3-yl)oxy)-2,4'-bipyridine | 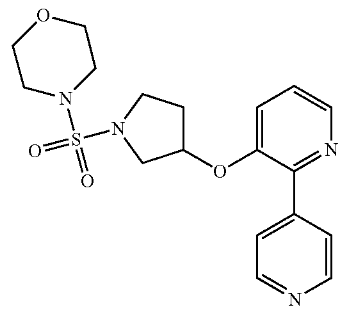 [SMILES: O=S(=O)(N1CCOCC1)N1CCC(Oc2cccnc2-c2ccncc2)C1] | 391.0 |
| 86 | 4-(2-((1-(ethylsulfonyl)pyrrolidin-3-yl)oxy)-4-fluorophenyl)pyrimidine | 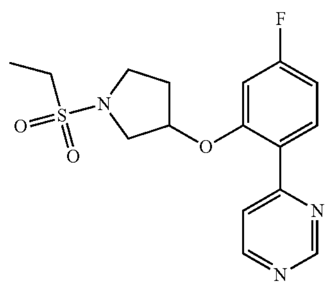 [SMILES: CCS(=O)(=O)N1CCC(Oc2cc(F)ccc2-c2ccncn2)C1] | 352.0 |
| 87 | 4-(2-((1-(cyclopropylsulfonyl)pyrrolidin-3-yl)oxy)-4-fluorophenyl)pyridine | 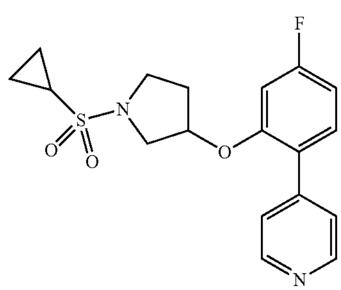 [SMILES: O=S(=O)(C1CC1)N1CCC(Oc2cc(F)ccc2-c2ccncc2)C1] | 363.1 |
| 88 | 4-(2-((1-(ethylsulfonyl)pyrrolidin-3-yl)oxy)-4-fluorophenyl)pyridine | 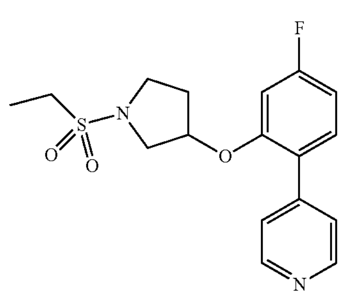 [SMILES: CCS(=O)(=O)N1CCC(Oc2cc(F)ccc2-c2ccncc2)C1] | 351.0 |

TABLE 1-9-continued

| Example No. | IUPAC Name | Structure | MS |
|---|---|---|---|
| 89 | 4-(4-fluoro-2-((1-((1-methyl-1H-pyrazol-4-yl)sulfonyl)pyrrolidin-3-yl)oxy)phenyl)pyridine | 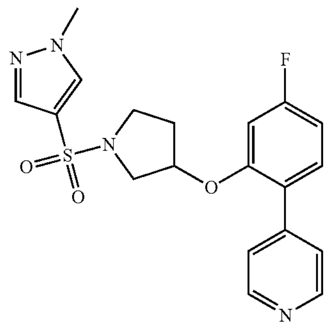 [SMILES: Cn1cc(S(=O)(=O)N2CCC(Oc3cc(F)ccc3-c3ccncc3)C2)cn1] | 403.0 |
| 90 | 4-(2-((1-benzylpyrrolidin-3-yl)oxy)phenyl)pyrimidine | 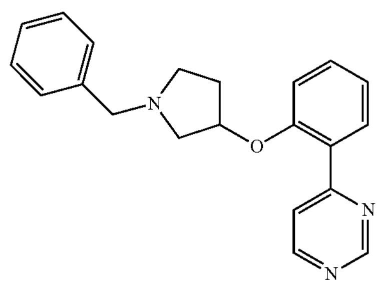 [SMILES: c1ccc(CN2CCC(Oc3ccccc3-c3ccncn3)C2)cc1] | 332.1 |

TABLE 1-10

| Example No. | IUPAC Name | Structure | MS |
|---|---|---|---|
| 91 | tert-butyl 3-((3-(pyridin-4-yl)pyrazin-2-yl)oxy)pyrrolidine-1-carboxylate | 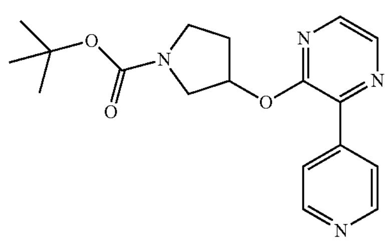 [SMILES: CC(C)(C)OC(=O)N1CCC(Oc2nccnc2-c2ccncc2)C1] | 343.2 |
| 92 | 4-(2-((1-(cyclopropylsulfonyl)pyrrolidin-3-yl)oxy)-5-fluorophenyl)pyrimidine | 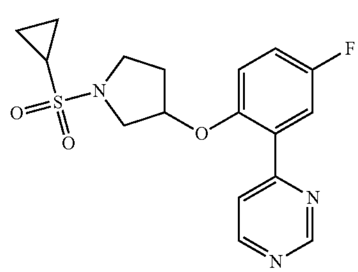 [SMILES: O=S(=O)(C1CC1)N1CCC(Oc2ccc(F)cc2-c2ccncn2)C1] | 364.1 |

TABLE 1-10-continued

| Example No. | IUPAC Name | Structure | MS |
|---|---|---|---|
| 93 | 4-(5-fluoro-2-((1-((1-methyl-1H-pyrazol-4-yl)sulfonyl)pyrrolidin-3-yl)oxy)phenyl)pyrimidine | 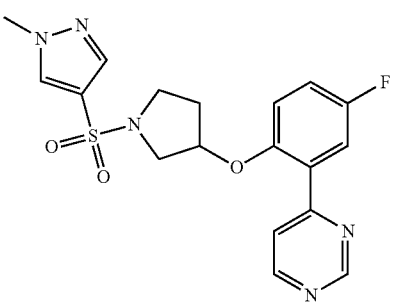 [SMILES: Cn1cc(S(=O)(=O)N2CCC(Oc3ccc(F)cc3-c3ccncn3)C2)cn1] | 404.1 |
| 94 | 4-(2-((1-(ethylsulfonyl)pyrrolidin-3-yl)oxy)-5-fluorophenyl)pyrimidine | 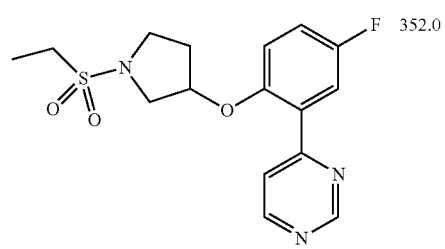 | 352.0 |
| 95 | 2-((1-(cyclopropylsulfonyl)pyrrolidin-3-yl)oxy)-3-(pyridin-4-yl)pyrazine | 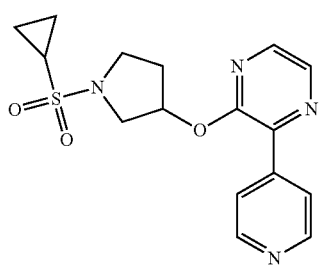 [SMILES: O=S(=O)(C1CC1)N1CCC(Oc2nccnc2-c2ccncc2)C1] | 347.1 |
| 96 | 2-((1-((1-methyl-1H-pyrazol-4-yl)sulfonyl)pyrrolidin-3-yl)oxy)-3-(pyridin-4-yl)pyrazine | 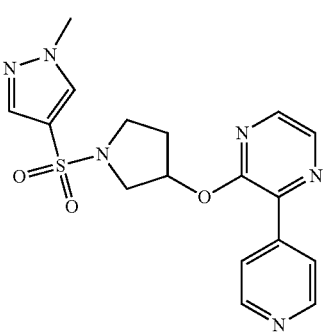 [SMILES: Cn1cc(S(=O)(=O)N2CCC(Oc3nccnc3-c3ccncc3)C2)cn1] | 387.1 |
| 97 | 2-((1-(ethylsulfonyl)pyrrolidin-3-yl)oxy)-3-(pyridin-4-yl)pyrazine | 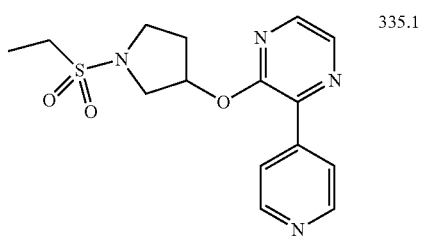 | 335.1 |

TABLE 1-10-continued

| Example No. | IUPAC Name | Structure | MS |
|---|---|---|---|
| 98 | optically active 3-((1-(cyclopropylsulfonyl)pyrrolidin-3-yl)oxy)-2,4'-bipyridine | 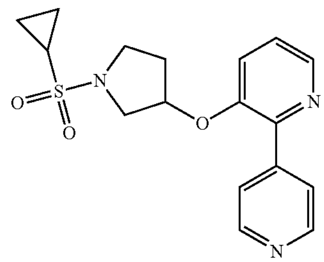 [SMILES: O=S(=O)(C1CC1)N1CCC(Oc2cccnc2-c2ccncc2)C1] | 346.1 |
| 99 | optically active 3-((1-(cyclopropylsulfonyl)pyrrolidin-3-yl)oxy)-2,4'-bipyridine | 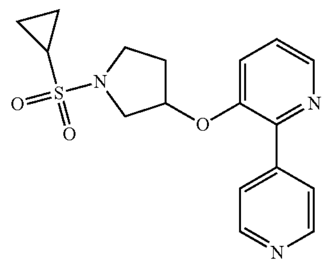 [SMILES: O=S(=O)(C1CC1)N1CCC(Oc2cccnc2-c2ccncc2)C1] | 346.1 |
| 100 | 4-(2-((1-(cyclopropylsulfonyl)pyrrolidin-3-yl)oxy)phenyl)pyrimidine | 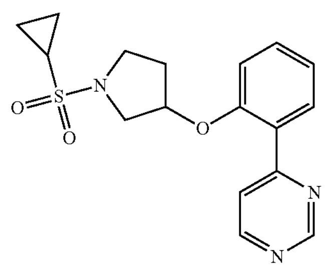 [SMILES: O=S(=O)(C1CC1)N1CCC(Oc2ccccc2-c2ccncn2)C1] | 346.1 |

TABLE 1-11

| Example No. | IUPAC Name | Structure | MS |
|---|---|---|---|
| 101 | 4-(2-((1-(ethylsulfonyl)pyrrolidin-3-yl)oxy)phenyl)pyrimidine | 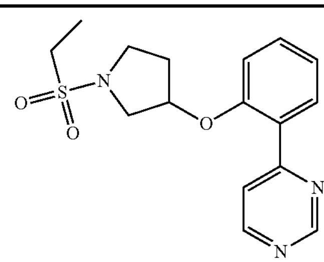 | 334.1 |
| 102 | 4-(2-((1-((1-methyl-1H-pyrazol-4-yl)sulfonyl)pyrrolidin-3-yl)oxy)phenyl)pyrimidine | 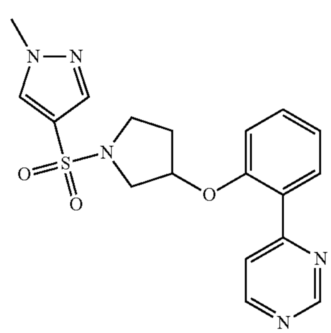 [SMILES: Cn1cc(S(=O)(=O)N2CCC(Oc3ccccc3-c3ccncn3)C2)cn1] | 386.0 |

TABLE 1-11-continued

| Example No. | IUPAC Name | Structure | MS |
|---|---|---|---|
| 103 | 4-(3-((1-((4-fluorophenyl)sulfonyl)pyrrolidin-3-yl)oxy)pyridin-2-yl)pyrimidine | 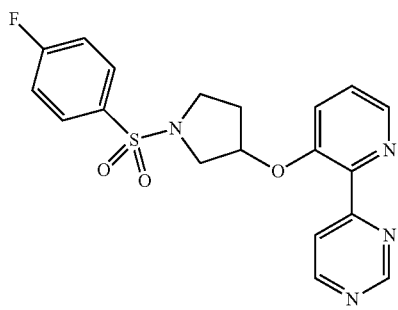 [SMILES: O=S(=O)(c1ccc(F)cc1)N1CCC(Oc2cccnc2-c2ccncn2)C1] | 401.0 |
| 104 | 4-(3-((1-(cyclopropylsulfonyl)pyrrolidin-3-yl)oxy)pyridin-2-yl)pyrimidine | 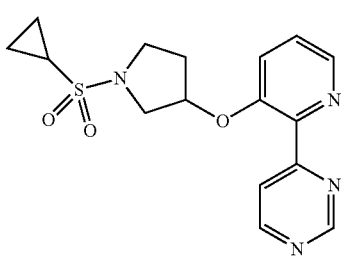 [SMILES: O=S(=O)(C1CC1)N1CCC(Oc2cccnc2-c2ccncn2)C1] | 347.1 |
| 105 | 4-(3-((1-(phenylsulfonyl)pyrrolidin-3-yl)oxy)pyridin-2-yl)pyrimidine | 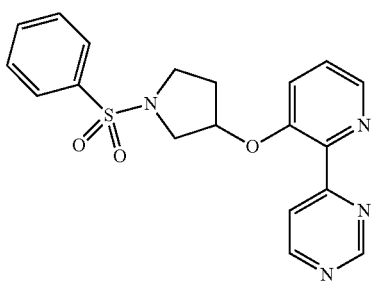 [SMILES: O=S(=O)(c1ccccc1)N1CCC(Oc2cccnc2-c2ccncn2)C1] | 383.1 |
| 106 | 3-((1-(isopropylsulfonyl)pyrrolidin-3-yl)oxy)-2,4'-bipyridine | 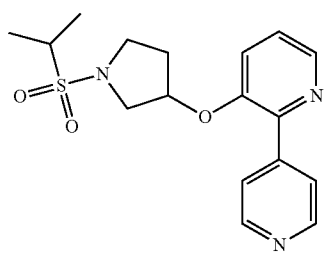 [SMILES: CC(C)S(=O)(=O)N1CCC(Oc2cccnc2-c2ccncc2)C1] | 348.2 |
| 107 | 2-((1-((1-methyl-1H-pyrazol-4-yl)sulfonyl)pyrrolidin-3-yl)oxy)-3-(pyridin-4-yl)benzonitrile | 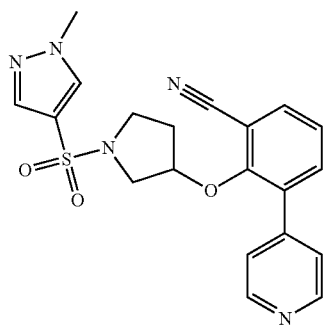 [SMILES: Cn1cc(S(=O)(=O)N2CCC(Oc3c(C#N)cccc3-c3ccncc3)C2)cn1] | 410.1 |

TABLE 1-11-continued

| Example No. | IUPAC Name | Structure | MS |
|---|---|---|---|
| 108 | 3-((1-(pyridin-3-ylsulfonyl)pyrrolidin-3-yl)oxy)-2,4'-bipyridine | 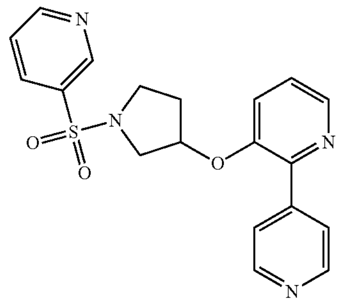 [SMILES: O=S(=O)(c1cccnc1)N1CCC(Oc2cccnc2-c2ccncc2)C1] | 383.1 |
| 109 | 2-((1-(ethylsulfonyl)pyrrolidin-3-yl)oxy)-3-(pyridin-4-yl)benzonitrile | 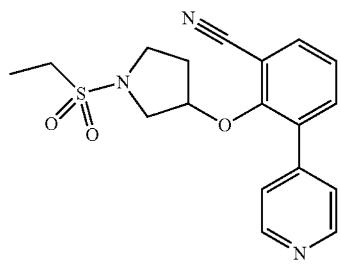 [SMILES: CCS(=O)(=O)N1CCC(Oc2c(C#N)cccc2-c2ccncc2)C1] | 358.0 |
| 110 | 2-((1-((4-fluorophenyl)sulfonyl)pyrrolidin-3-yl)oxy)-3-(pyridin-4-yl)pyrazine | 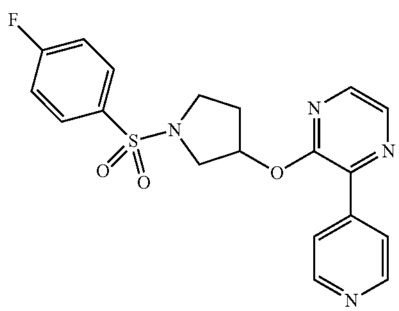 [SMILES: O=S(=O)(c1ccc(F)cc1)N1CCC(Oc2nccnc2-c2ccncc2)C1] | 401.0 |

TABLE 1-12

| Example No. | IUPAC Name | Structure | MS |
|---|---|---|---|
| 111 | 2-((1-((2,4-difluorophenyl)sulfonyl)pyrrolidin-3-yl)oxy)-3-(pyridin-4-yl)pyrazine | 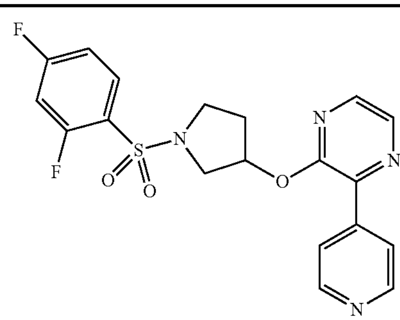 | 419.1 |

TABLE 1-12-continued
| Example No. | IUPAC Name | Structure | MS |
|---|---|---|---|
| 112 | 4-((1-(cyclopropylsulfonyl)pyrrolidin-3-yl)oxy)-5-(pyridin-4-yl)pyrimidine | 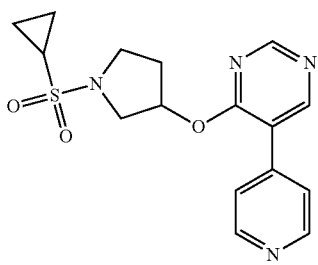 [SMILES: O=S(=O)(C1CC1)N1CCC(Oc2ncncc2-c2ccncc2)C1] | 347.1 |
| 113 | 4-((1-((4-fluorophenyl)sulfonyl)pyrrolidin-3-yl)oxy)-5-(pyridin-4-yl)pyrimidine | 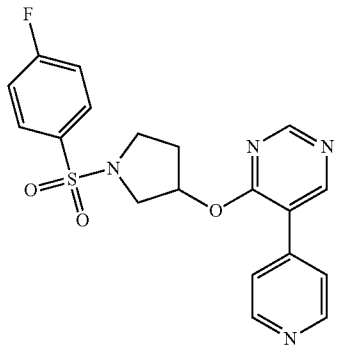 [SMILES: O=S(=O)(c1ccc(F)cc1)N1CCC(Oc2ncncc2-c2ccncc2)C1] | 401.0 |
| 114 | 4-((1-((4-methoxyphenyl)sulfonyl)pyrrolidin-3-yl)oxy)-5-(pyridin-4-yl)pyrimidine | 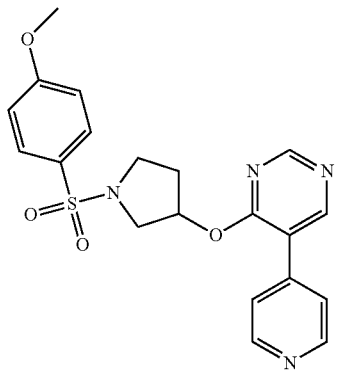 [SMILES: COc1ccc(S(=O)(=O)N2CCC(Oc3ncncc3-c3ccncc3)C2)cc1] | 413.1 |
| 115 | 2-((1-((4-methoxyphenyl)sulfonyl)pyrrolidin-3-yl)oxy)-3-(pyridin-4-yl)pyrazine | 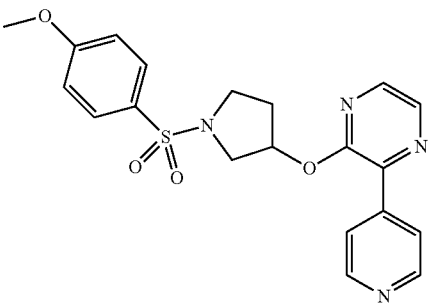 [SMILES: COc1ccc(S(=O)(=O)N2CCC(Oc3nccnc3-c3ccncc3)C2)cc1] | 413,1 |

TABLE 1-12-continued
| Example No. | IUPAC Name | Structure | MS |
|---|---|---|---|
| 116 | 4-(2-((1-((4-methoxyphenyl)sulfonyl)pyrrolidin-3-yl)oxy)-4-(trifluoromethyl)phenyl)pyrimidine | 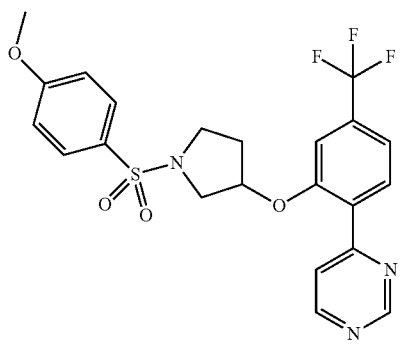 [SMILES: COc1ccc(S(=O)(=O)N2CCC(Oc3cc(C(F)(F)F)ccc3-c3ccncn3)C2)cc1] | 480.1 |
| 117 | 4-(2-((1-(cyclopropylsulfonyl)pyrrolidin-3-yl)oxy)-4-(trifluoromethyl)phenyl)pyrimidine | 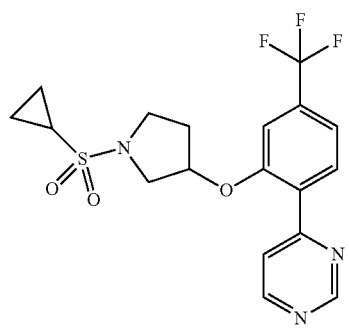 [SMILES: O=S(=O)(C1CC1)N1CCC(Oc2cc(C(F)(F)F)ccc2-c2ccncn2)C1] | 414.1 |
| 118 | (4-benzoylpiperazin-1-yl)(5-methyl-2-(pyridin-4-yl)phenyl)methanone | 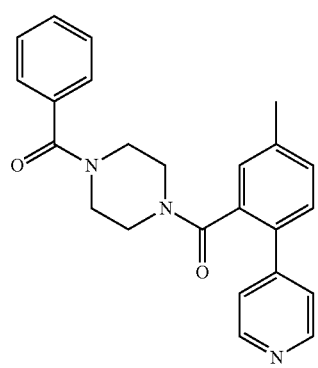 [SMILES: Cc1ccc(-c2ccncc2)c(C(=O)N2CCN(C(=O)c3ccccc3)CC2)c1] | 386.2 |
| 119 | (4-benzylpiperazin-1-yl)(5-methyl-2-(pyridin-4-yl)phenyl)methanone | 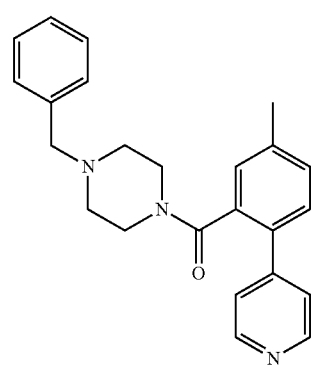 [SMILES: Cc1ccc(-c2ccncc2)c(C(=O)N2CCN(Cc3ccccc3)CC2)c1] | 372.2 |

TABLE 1-12-continued

| Example No. | IUPAC Name | Structure | MS |
|---|---|---|---|
| 120 | 3-((1-(phenylsulfonyl)pyrrolidin-3-yl)oxy)-2,4'-bipyridine | 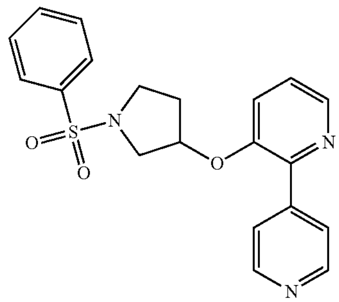 [SMILES: O=S(=O)(c1ccccc1)N1CCC(Oc2cccnc2-c2ccncc2)C1] | 382.0 |

TABLE 1-13

| Example No. | IUPAC Name | Structure | MS |
|---|---|---|---|
| 121 | (3-(2,4'-bipyridin-3-yloxy)pyrrolidin-1-yl)(phenyl)methanone | 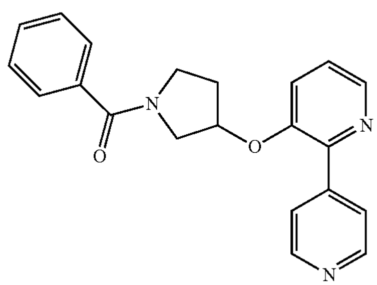 [SMILES: O=C(c1ccccc1)N1CCC(Oc2cccnc2-c2ccncc2)C1] | 346.2 |
| 122 | 3-((1-(phenylsulfonyl)piperidin-4-yl)oxy)-2,4'-bipyridine | 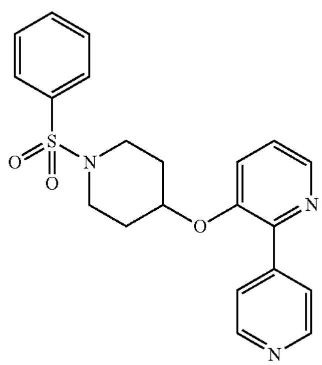 [SMILES: O=S(=O)(c1ccccc1)N1CCC(Oc2cccnc2-c2ccncc2)CC1] | 396.1 |
| 123 | (4-(2,4'-bipyridin-3-yloxy)piperidin-1-yl)(phenyl)methanone | 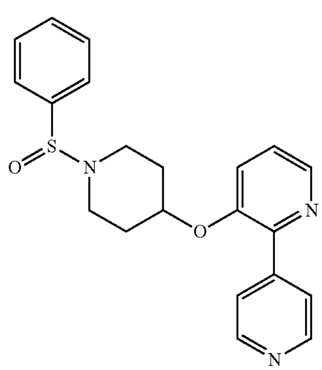 [SMILES: O=S(c1ccccc1)N1CCC(Oc2cccnc2-c2ccncc2)CC1] | 360.1 |

TABLE 1-13-continued

| Example No. | IUPAC Name | Structure | MS |
|---|---|---|---|
| 124 | 3-((1-(pyridin-2-ylmethyl)piperidin-4-yl)oxy)-2,4'-bipyridine | 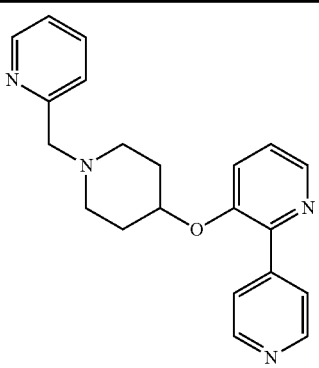 | 347.2 |
| 125 | 3-((1-(pyridin-3-ylmethyl)piperidin-4-yl)oxy)-2,4'-bipyridine | 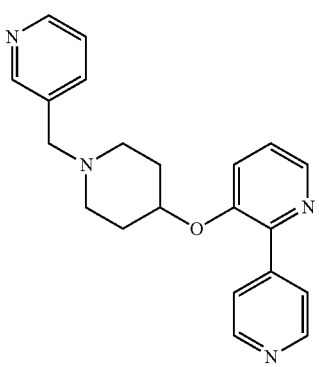 [SMILES: c1cncc(CN2CCC(Oc3cccnc3-c3ccncc3)CC2)c1] | 347.2 |
| 126 | 3-((1-(cyclopropylmethyl)piperidin-4-yl)oxy)-2,4'-bipyridine | 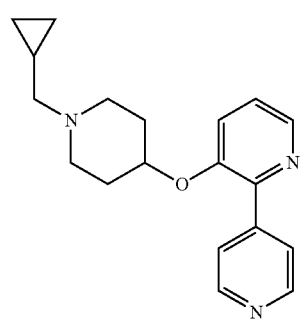 [SMILES: c1cnc(-c2ccncc2)c(OC2CCN(CC3CC3)CC2)c1] | 310.2 |

Formulation Example 1

Production of Capsule

| | |
|---|---|
| 1) compound of Example 1 | 30 mg |
| 2) fine powder cellulose | 10 mg |
| 3) lactose | 19 mg |
| 4) magnesium stearate | 1 mg |
| Total | 60 mg |

1), 2), 3) and 4) are mixed and filled in a gelatin capsule.

Formulation Example 2

Production of Tablet

| | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

Experimental Example 1

Construction of Human CH24H (CYP46) Expression Vector

A plasmid DNA for expressing human CH24H in a FreeStyle 293 cell was produced as follows. Using Full-Length Mammalian Gene Collection No. 4819975 (Invitrogen) as a template, and the following two kinds of synthesized DNAs:

```
                                         (SEQ ID NO: 1)
5'-GCCCCGGAGCCATGAGCCCCGGGCTG-3'
and (SEQ ID NO: 2)
5'-GTCCTGCCTGGAGGCCCCCTCAGCAG-3',
```

PCR was performed to amplify 91-1625 bp region of human CH24H (BCO22539). The obtained fragment was cloned using TOPO TA Cloning Kit (Invitrogen). The obtained fragment was subcloned to pcDNA3.1(+) digested with BamHI and XhoI to give a plasmid DNA for human CH24H expression (pcDNA3.1(+)/hCH24H).

Experimental Example 2

Expression of Human CH24H and Preparation of Human CH24H Lysate

The expression of human CH24H was performed using FreeStyle 293 Expression System (Invitrogen). According to the manual attached to FreeStyle 293 Expression System and using the plasmid DNA for human CH24H expression (pcDNA3.1(+)/hCH24H) constructed in Experimental Example 1, a transient expression using FreeStyle 293-F cell was performed. After transfection, the cells were cultured at 37° C., 8% $CO_2$ with shaking at 125 rpm for 2 days. The cells were collected by centrifugation, and suspended in a suspension buffer (100 mM potassium phosphate (pH 7.4), 0.1 mM EDTA, 1 mM DTT, 20% Glycerol). The suspended product was disrupted by a polytron homogenizer (manufactured by Kinematica), and centrifuged at 9000×g for 10 min, and the supernatant was collected. The collected supernatant was cryopreserved (−80° C.) as a human CH24H lysate standard product.

Experimental Example 3

Measurement of CH24H Inhibitory Activity

For the measurement of CH24H inhibitory activity, using the human CH24H lysate prepared in Experimental Example 2, the amount of 24-HC produced from cholesterol by catalytic activity of CH24H was measured in the presence of a test compound, and compared with that measured in the absence of the test compound. That is, a test compound solution at various concentrations was mixed with a reaction buffer (50 mM potassium phosphate containing 0.1% BSA and Complete, EDTA-free, pH 7.4) and human CH24H lysate. Then, [$^{14}$C] cholesterol (53 mCi/mmol specific activity, 15 μM) was added, and CH24H reaction was performed at 37° C. for 5 hr. After completion of the reaction, a quenching solution consisting of chloroform/methanol/distilled water (2:2:1 v/v) was added, and the resulting 24-HC was extracted by shaking. The extract was applied to silica gel thin layer chromatography (ethyl acetate:toluene=4:6), and the obtained $^{14}$C-24HC fraction was measured with BAS2500 (Fujifilm Corporation).

The inhibitory rate (%) was calculated from the ratio of radioactivity in the presence of a test compound relative to the radioactivity in the absence of the test compound. The results are shown in the following Table 2.

TABLE 2

| Test Compound | Inhibitory Rate in 1 μM (%) |
| --- | --- |
| Example 3 | 87 |
| Example 4 | 86 |
| Example 5 | 92 |
| Example 15 | 94 |
| Example 16 | 93 |
| Example 20 | 83 |
| Example 22 | 89 |
| Example 29 | 59 |
| Example 34 | 91 |
| Example 38 | 84 |
| Example 40 | 88 |
| Example 47 | 90 |
| Example 49 | 85 |
| Example 54 | 79 |
| Example 55 | 53 |
| Example 61 | 89 |
| Example 64 | 92 |
| Example 67 | 80 |
| Example 71 | 89 |
| Example 74 | 88 |
| Example 84 | 87 |
| Example 85 | 84 |
| Example 88 | 82 |
| Example 110 | 89 |
| Example 120 | 94 |
| Example 124 | 95 |

Experimental Example 4

Quantification Test of 24-HC

Animals used were 6-week-old female C57BL/6N mice (3 mice/group). A test compound was suspended in a 0.5% aqueous methylcellulose [133-14255 WAKO] solution (1 mg/mL). The body weight of the mice was measured, and the solution was forcibly administered orally and repeatedly once a day for 3 days. At 16 hours after the third administration, half of the brain was harvested, and the amount of 24-HC was measured.

The wet weight of the brain was measured, and the brain was homogenized with 4-fold amount of saline. This solution was used as a brain extract. The 24-HC in the brain extract was extracted with an acetonitrile solution (98% acetonitrile, 1.98% methanol, 0.02% formic acid), and quantified by HPLC. The average value of 24-HC amount was calculated and the results are shown in relative values with the control group as 100%. The results are shown in the following Table 3.

TABLE 3

| Test Compound | Decreasing Rate in 10 mg/kg (%) | Decreasing Rate in 30 mg/kg (%) |
| --- | --- | --- |
| Example 22 |  | 77 |
| Example 40 | 84 |  |
| Example 47 | 75 |  |
| Example 54 | 73 |  |

TABLE 3-continued

| Test Compound | Decreasing Rate in 10 mg/kg (%) | Decreasing Rate in 30 mg/kg (%) |
|---|---|---|
| Example 71 | | 86 |

INDUSTRIAL APPLICABILITY

The compound of the present invention has a superior CH24H inhibitory action, which is useful as an agent for the prophylaxis or treatment of epilepsy, neurodegenerative disease (e.g., Alzheimer's disease, mild cognitive disorder, Huntington's disease, Parkinson's disease, multiple sclerosis, amyotrophic lateral sclerosis, traumatic brain injury, cerebral infarction, glaucoma and the like), schizophrenia and the like.

This application is based on patent application No. 2013-079023 filed on Apr. 4, 2013 in Japan, the contents of which are encompassed in full herein.

The invention claimed is:

1. A compound represented by the formula (I):

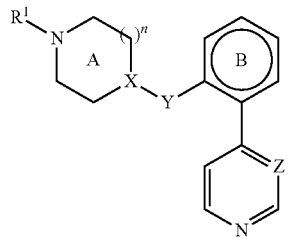

(I)

wherein
X is a carbon atom or a nitrogen atom;
Y is —O—, —S—, —NH—, —CH$_2$—, —CO—, —SO— or —SO$_2$—;
Z is CR$^4$ or N;
R$^1$ is an optionally substituted C$_{1-6}$ alkyl group, —CO—R$^2$, or —SO$_2$—R$^3$;
R$^2$ is an optionally substituted C$_{1-6}$ alkyl group, an optionally substituted C$_{1-6}$ alkoxy group, an optionally substituted C$_{6-14}$ aryl group, or an optionally substituted C$_{3-8}$ cycloalkyl group;
R$^3$ is a substituent;
R$^4$ is a hydrogen atom or a substituent;
n is 0 or 1;
Ring A is a 5- or 6-membered nitrogen-containing heterocycle optionally further substituted by 1 to 3 substituents selected from a halogen atom, an acyl group, an optionally substituted C$_{1-6}$ alkyl group, an optionally substituted hydroxy group, an optionally substituted sulfanyl group, an optionally substituted amino group and an oxo group; and
Ring B is a 6-membered aromatic ring optionally further substituted by 1 to 3 substituents selected from a halogen atom, a cyano group, an acyl group, an optionally substituted C$_{1-6}$ alkyl group, an optionally substituted hydroxy group, an optionally substituted sulfanyl group, and an optionally substituted amino group,
provided that (4-ethylpiperazin-1-yl)(2-(pyrimidin-4-yl)phenyl)methanone, and (4-methylpiperazin-1-yl)(2-(pyrimidin-4-yl)phenyl)methanone are excluded, or a salt thereof.

2. The compound or salt of claim 1, wherein
X is a carbon atom or a nitrogen atom;
Y is —O—, —CH$_2$—, —CO— or —SO$_2$—;
Z is CH or N;
R$^1$ is
(1) a C$_{1-6}$ alkyl group optionally substituted by 1 to 3 substituents selected from
   (i) a C$_{6-14}$ aryl group optionally substituted by 1 to 3 substituents selected from
      (a) a C$_{1-6}$ alkoxy group,
      (b) a cyano group, and
      (c) a halogen atom,
   (ii) a pyridyl group, an imidazolyl group, an oxazolyl group, a pyrazolyl group, a tetrahydrofuryl group, an isoxazolyl group, a pyrimidinyl group, a pyrazinyl group and a thiazolyl group, each optionally substituted by 1 to 3 $C_{1-6}$ alkyl groups,
(iii) a $C_{3-8}$ cycloalkyl group,
(iv) a mono- or di-$C_{1-6}$ alkyl-carbamoyl group, and
(v) a pyrrolidinylcarbonyl group, a morpholinylcarbonyl group and an azetidinylcarbonyl group,
(2) —CO—$R^2$ wherein $R^2$ is
  (i) a $C_{1-6}$ alkyl group optionally substituted by 1 to 3 substituents selected from
    (a) a $C_{6-14}$ aryl group optionally substituted by 1 to 3 $C_{1-6}$ alkoxy groups, and
    (b) a $C_{3-8}$ cycloalkyl group,
  (ii) a $C_{1-6}$ alkoxy group,
  (iii) a $C_{6-14}$ aryl group, or
  (iv) a $C_{3-8}$ cycloalkyl group, or
(3) —$SO_2$—$R^3$ wherein $R^3$ is
  (i) a $C_{1-6}$ alkyl group optionally substituted by 1 to 3 halogen atoms,
  (ii) a $C_{3-8}$ cycloalkyl group,
  (iii) a $C_{6-14}$ aryl group optionally substituted by 1 to 3 substituents selected from
    (a) a $C_{1-6}$ alkoxy group, and
    (b) a halogen atom,
  (iv) a pyrazolyl group, a morpholinyl group or a pyridyl group, each optionally substituted by 1 to 3 $C_{1-6}$ alkyl groups, or
  (v) a mono- or di-$C_{1-6}$ alkyl-amino group;
n is 0 or 1;
Ring A is a pyrrolidine ring, a piperidine ring or a piperazine ring, each optionally further substituted by 1 to 3 substituents selected from
  (1) a halogen atom, and
  (2) an oxo group; and
Ring B is a benzene ring, a pyridine ring, a pyrimidine ring or a pyrazine ring, each optionally further substituted by 1 to 3 substituents selected from
  (1) a halogen atom,
  (2) a cyano group, and
  (3) a $C_{1-6}$ alkyl group optionally substituted by 1 to 3 halogen atoms.
3. The compound or salt of claim 1, wherein
X is a carbon atom or a nitrogen atom;
Y is —O—, —$CH_2$—, —CO— or —$SO_2$—;
Z is CH or N;
$R^1$ is
(1) a $C_{1-6}$ alkyl group substituted by 1 to 3 substituents selected from
  (i) a phenyl group optionally substituted by 1 to 3 substituents selected from
    (a) a $C_{1-6}$ alkoxy group,
    (b) a cyano group, and
    (c) a halogen atom,
  (ii) a pyridyl group, an imidazolyl group, an oxazolyl group, a pyrazolyl group, a tetrahydrofuryl group, an isoxazolyl group, a pyrimidinyl group, a pyrazinyl group and a thiazolyl group, each optionally substituted by 1 to 3 $C_{1-6}$ alkyl groups,
  (iii) a cyclopropyl group,
  (iv) a mono- or di-$C_{1-6}$ alkyl-carbamoyl group, and
  (v) a pyrrolidinylcarbonyl group, a morpholinylcarbonyl group and an azetidinylcarbonyl group,
(2) —CO—$R^2$ wherein $R^2$ is
  (i) a $C_{1-6}$ alkyl group optionally substituted by 1 to 3 substituents selected from
    (a) a phenyl group optionally substituted by 1 to 3 $C_{1-6}$ alkoxy groups, and
    (b) a cyclopropyl group,
  (ii) a $C_{1-6}$ alkoxy group,
  (iii) a phenyl group, or
  (iv) a cyclopropyl group, or
(3) —$SO_2$—$R^3$ wherein $R^3$ is
  (i) a $C_{1-6}$ alkyl group optionally substituted by 1 to 3 halogen atoms,
  (ii) a cyclopropyl group,
  (iii) a phenyl group optionally substituted by 1 to 3 substituents selected from
    (a) a $C_{1-6}$ alkoxy group, and
    (b) a halogen atom,
  (iv) a pyrazolyl group, a morpholinyl group or a pyridyl group, each optionally substituted by 1 to 3 $C_{1-6}$ alkyl groups, or
  (v) a mono- or di-$C_{1-6}$ alkyl-amino group;
n is 0 or 1;
Ring A is a pyrrolidine ring, a piperidine ring or a piperazine ring, each optionally further substituted by 1 to 3 substituents selected from
  (1) a halogen atom, and
  (2) an oxo group; and
Ring B is a benzene ring, a pyridine ring, a pyrimidine ring or a pyrazine ring, each optionally further substituted by 1 to 3 substituents selected from
  (1) a halogen atom,
  (2) a cyano group, and
  (3) a $C_{1-6}$ alkyl group optionally substituted by 1 to 3 halogen atoms.
4. The compound or salt of claim 1, wherein
X is a carbon atom;
Y is —O—;
Z is CH;
$R^1$ is
(1) a $C_{1-6}$ alkyl group optionally substituted by 1 to 3 substituents selected from
  (i) a pyrazolyl group and a thiazolyl group, each optionally substituted by 1 to 3 $C_{1-6}$ alkyl groups, and
  (ii) a mono- or di-$C_{1-6}$ alkyl-carbamoyl group, or
(2) —$SO_2$—$R^3$ wherein $R^3$ is a phenyl group optionally substituted by 1 to 3 $C_{1-6}$ alkoxy groups;
n is 0 or 1;
Ring A is a pyrrolidine ring or a piperidine ring, each optionally further substituted by 1 to 3 halogen atoms; and
Ring B is a pyridine ring or a pyrazine ring.
5. 3-((1-(1-Methyl-1H-pyrazol-4-yl)methyl)piperidin-4-yl)oxy)-2,4'-bipyridine or a salt thereof.
6. 2-(3,3-Difluoro-4-((3-(pyridin-4-yl)pyrazin-2-yl)oxy)piperidin-1-yl)-N,N-dimethylacetamide or a salt thereof.
7. 3-((1-((4-Methoxyphenyl)sulfonyl)pyrrolidin-3-yl)oxy)-2,4'-bipyridine or a salt thereof.
8. A medicament comprising the compound or salt of claim 1.
9. The medicament of claim 8, which is a cholesterol 24 hydroxylase inhibitor.
10. The medicament of claim 8, which is an agent for the treatment of epilepsy or neurodegenerative disease.
11. The medicament of claim 10, wherein the neurodegenerative disease is Alzheimer's disease, mild cognitive disorder, Huntington's disease, Parkinson's disease or multiple sclerosis.
12. A method of inhibiting cholesterol 24-hydroxylase in a mammal, which comprises administering an effective amount of the compound or salt of claim 1 to the mammal.

13. A method for the treatment of epilepsy or neurodegenerative disease in a mammal, which comprises administering an effective amount of the compound or salt of claim 1 to the mammal.

14. The method of claim 13, wherein the neurodegenerative disease is Alzheimer's disease, mild cognitive disorder, Huntington's disease, Parkinson's disease or multiple sclerosis.

* * * * *